(12) United States Patent
Magnussen et al.

(10) Patent No.: US 11,085,876 B2
(45) Date of Patent: Aug. 10, 2021

(54) DEVICE AND METHOD FOR DETERMINING A CONCENTRATION IN A SAMPLE

(71) Applicant: Opsolution GMBH, Kassel (DE)

(72) Inventors: Bjoern Magnussen, Kassel (DE); Claudius Stern, Ahnatal (DE); Wolfgang Koecher, Kassel (DE)

(73) Assignee: Opsolution GMBH

( * ) Notice: Subject to any disclaimer, the term of this patent is extended or adjusted under 35 U.S.C. 154(b) by 0 days.

(21) Appl. No.: 16/570,615

(22) Filed: Sep. 13, 2019

(65) Prior Publication Data

US 2020/0217792 A1  Jul. 9, 2020

Related U.S. Application Data

(63) Continuation of application No. 15/109,658, filed as application No. PCT/EP2014/078466 on Dec. 18, 2014, now Pat. No. 10,416,079.

(30) Foreign Application Priority Data

Jan. 7, 2014 (DE) ..................... 10 2014 100 112.5
Feb. 14, 2014 (DE) ..................... 10 2014 101 918.0

(51) Int. Cl.
*G01N 21/49* (2006.01)
*A61B 5/1455* (2006.01)
(Continued)

(52) U.S. Cl.
CPC ........... *G01N 21/49* (2013.01); *A61B 5/1455* (2013.01); *A61B 5/14546* (2013.01);
(Continued)

(58) Field of Classification Search
CPC .......... G01N 21/49; G01N 2201/06153; A61B 5/14546; A61B 5/1455; G01J 2003/102
See application file for complete search history.

(56) References Cited

U.S. PATENT DOCUMENTS 5,057,695 A   10/1991  Hirao et al.
5,267,152 A * 11/1993  Yang .................... A61B 5/1455
                                                       250/339.09
(Continued)

FOREIGN PATENT DOCUMENTS

DE    44 27 101     2/1996
DE    101 63 972    7/2003
(Continued)

OTHER PUBLICATIONS

Alaluf, S., U. Heinrich, W. Stahl, H. Tronnier, and S. Wiseman. "Dietary Cartoenoids Contribute to Normal Human Skin Color and UV Photosensitivity." The Journal of Nutrition 2002, vol. 132, pp. 399-403.

(Continued)

*Primary Examiner* — Maurice C Smith
(74) *Attorney, Agent, or Firm* — Knobbe, Martens, Olson & Bear, LLP

(57) ABSTRACT

A device for optical detection of analytes in a sample includes at least two optoelectronic components. The optoelectronic components include at least one optical detector configured to receive a photon and at least one optical emitter configured to emit a photon. The at least one optical emitter includes at least three optical emitters disposed in a flat, non-linear arrangement, and the at least one optical detector includes at least three optical detectors disposed in a flat, non-linear arrangement. The at least three optical emitters and the at least three optical detectors include at least three different wavelength characteristics.

43 Claims, 29 Drawing Sheets

(51) Int. Cl.
*G01N 21/47* (2006.01)
*A61B 5/145* (2006.01)
*G01N 21/17* (2006.01)

(52) U.S. Cl.
CPC ....... *G01N 21/474* (2013.01); *G01N 21/4795* (2013.01); *A61B 5/14532* (2013.01); *A61B 2560/0223* (2013.01); *A61B 2562/046* (2013.01); *G01N 2021/1782* (2013.01); *G01N 2021/4752* (2013.01); *G01N 2201/066* (2013.01); *G01N 2201/0621* (2013.01); *G01N 2201/0626* (2013.01); *G01N 2201/0633* (2013.01); *G01N 2201/06153* (2013.01); *G01N 2201/1211* (2013.01); *G01N 2201/1214* (2013.01)

(56) References Cited

U.S. PATENT DOCUMENTS

| | | | |
|---|---|---|---|
| 5,551,422 | A | 9/1996 | Simonsen et al. |
| 5,873,831 | A | 2/1999 | Bernstein et al. |
| 5,986,770 | A | 11/1999 | Hein et al. |
| 6,150,823 | A | 11/2000 | Takashi |
| 6,167,290 | A | 12/2000 | Yang et al. |
| 6,205,354 | B1 | 3/2001 | Gellermann et al. |
| 6,223,063 | B1 | 4/2001 | Chaiken et al. |
| 6,289,230 | B1 | 9/2001 | Chaiken et al. |
| 6,315,412 | B1 | 11/2001 | Snodderly et al. |
| 6,526,299 | B2 | 2/2003 | Pickard |
| 7,139,076 | B1 | 11/2006 | Marbach |
| 7,593,763 | B2 | 9/2009 | Lambert et al. |
| 7,647,092 | B2 | 1/2010 | Motz et al. |
| 8,055,321 | B2 | 11/2011 | Bernreuter |
| 8,260,402 | B2 | 9/2012 | Ermakov et al. |
| 8,938,279 | B1 | 1/2015 | Heaton, II |
| 10,416,079 | B2 | 9/2019 | Magnussen et al. |
| 2002/0024785 | A1 | 2/2002 | Yano |
| 2002/0058865 | A1 | 5/2002 | Cheng et al. |
| 2003/0050541 | A1* | 3/2003 | Wuori ............ A61B 5/14532 600/316 |
| 2003/0130579 | A1 | 7/2003 | McClane et al. |
| 2004/0254479 | A1 | 12/2004 | Fralick et al. |
| 2005/0002031 | A1 | 1/2005 | Kraemer et al. |
| 2005/0020892 | A1 | 1/2005 | Acosta et al. |
| 2005/0197581 | A1 | 9/2005 | Ferguson et al. |
| 2005/0240090 | A1 | 10/2005 | Ruchti et al. |
| 2005/0037505 | A1 | 12/2005 | Samsoondar |
| 2006/0244947 | A1 | 11/2006 | Rowe |
| 2007/0078349 | A1 | 4/2007 | Ferguson et al. |
| 2007/0166354 | A1 | 7/2007 | Barrett-Reis |
| 2008/0232653 | A1 | 9/2008 | Rowe |
| 2009/0326393 | A1 | 12/2009 | Sethi |
| 2010/0130840 | A1 | 5/2010 | Isaacson |
| 2010/0217098 | A1 | 8/2010 | LeBoeuf |
| 2012/0071739 | A1 | 3/2012 | Chen |
| 2012/0253149 | A1 | 10/2012 | Steuer |
| 2013/0289414 | A1 | 10/2013 | Adibnazari et al. |
| 2014/0058224 | A1* | 2/2014 | Gellermann ........... G01N 21/65 600/314 |
| 2014/0200419 | A1 | 7/2014 | Ermakov et al. |
| 2014/0378797 | A1 | 12/2014 | Hendriks et al. |
| 2015/0011850 | A1 | 1/2015 | Ruchti |
| 2015/0363631 | A1 | 12/2015 | Holz |
| 2020/0300754 | A1 | 9/2020 | Bock et al. |

FOREIGN PATENT DOCUMENTS

| | | |
|---|---|---|
| DE | 102012005583 | 5/2013 |
| JP | H 10-314151 | 12/1998 |
| JP | 3798550 | 7/2006 |
| JP | 5574246 | 7/2014 |
| WO | WO 94/10901 | 5/1994 |
| WO | WO 00/78217 | 12/2000 |
| WO | WO 2009/149266 | 12/2009 |
| WO | WO 2010/056973 | 5/2010 |
| WO | WO 2013/134747 | 9/2013 |

OTHER PUBLICATIONS

Ermakov, I.V., M.R. Ermakov, R.W. McClane, and W. Gellermann. "Resonance Raman detection of carotenoid antioxidants in living human tissues." Optics Letters 2001, vol. 26, No. 15, pp. 1179-1181.

Ermakov, I.V., M.R. Ermakov, W. Gellermann. "Noninvasive selective detection of lycopene and β-carotene in human skin using Raman spectroscopy." Journal of Biomedical Optics 2004, vol. 9, No. 2, pp. 332-338.

Gellermann, W., J.A. Zidichouski, C.R. Smidt, and P.S. Bernstein. "Chapter 6: Raman Detection of Carotenoids in Human Tissue," in Carotenoids and Retinoids: Molecular Aspects and Health Issues, eds. L. Packer, U. Obermueller-Jevic, K. Kraemer, H. Sies. American Oil Chemists Society, 2004, pp. 86-114.

Hata, T.R., T.A. Scholz, I.V. Ermakov, R.W. McClane, F. Khachik, W. Gellerman, and L.K. Pershing. "Non-invasive Raman Spectroscopic Detection of Carotenoids in Human Skin." The Journal of Investigative Dermatology 2000, vol. 115, No. 3, pp. 441-448.

Kolonel, L.N., J.H. Hankin, A.S. Whittemore, A.H. Wu, R.P. Gallagher, L.R. Wilkens, E.M. John, G.R. Howe, D.M. Dreon, D.W. West, and R.S. Paffenbarger, Jr. "Vegetables, Fruits, Legumes and Prostate Cancer: A Multiethnic Case-Control Study." Cancer Epidemiology, Biomarkers & Prevention 2000, vol. 9, pp. 795-804.

Liu, S., J.E. Manson, I. Lee, S.R. Cole, C.H. Hennekens, W.C. Willett, and J.E. Buring. "Fruit and vegetable intake and risk of cardiovascular disease: the Women's Health Study." The American Journal of Clinical Nutrition 2000, vol. 72, pp. 922-928.

Michaud, D.S., D. Feskanich, E.B. Rimm, G.A. Colditz, F.E. Speizer, W.C. Willett, and E. Giovannucci. "Intake of specific carotenoids and risk of lung cancer in 2 prospective US cohorts." The American Journal of Clinical Nutrition 2000, vol. 72, pp. 990-997.

Niedorf, F., H. Jungmann, M. Kietzmann. "Noninvasive reflection spectra provide quantitative information about the spatial distribution of skin chromophores." Medical Physics 2005, vol. 32, No. 5, pp. 1297-1307.

Stahl, W. U. Heinrich, H. Jungmann, H. Tronnier, and H. Sies. "Carotenoids in Human Skin: Noninvasive Measurement and Identification of Dermal Carotenoids and Carotenol Esters." Methods in Enzymology 2000, vol. 319, pp. 494-502.

Stahl, W., U. Heinrich, H. Jungmann, J. von Laar, M. Schietzel, H. Sies, and H. Tronnier. "Increased Dermal Carotenoid Levels Assessed by Noninvasive Reflection Spectrophotometry Correlate with Serum Levels in Women Ingesting Betatene." The Journal of Nutrition 1998, vol. 128, pp. 903-907.

The Age-Related Eye Disease Study Research Group. "The Relationship of Dietary Carotenoid and Vitamin A,E, and C Intake With Age-Related Macular Degeneration in a Case-Control Study." Archives of Ophthalmology 2007, vol. 125, No. 9, pp. 1225-1232.

\* cited by examiner 16x 3.15

24x 3.10

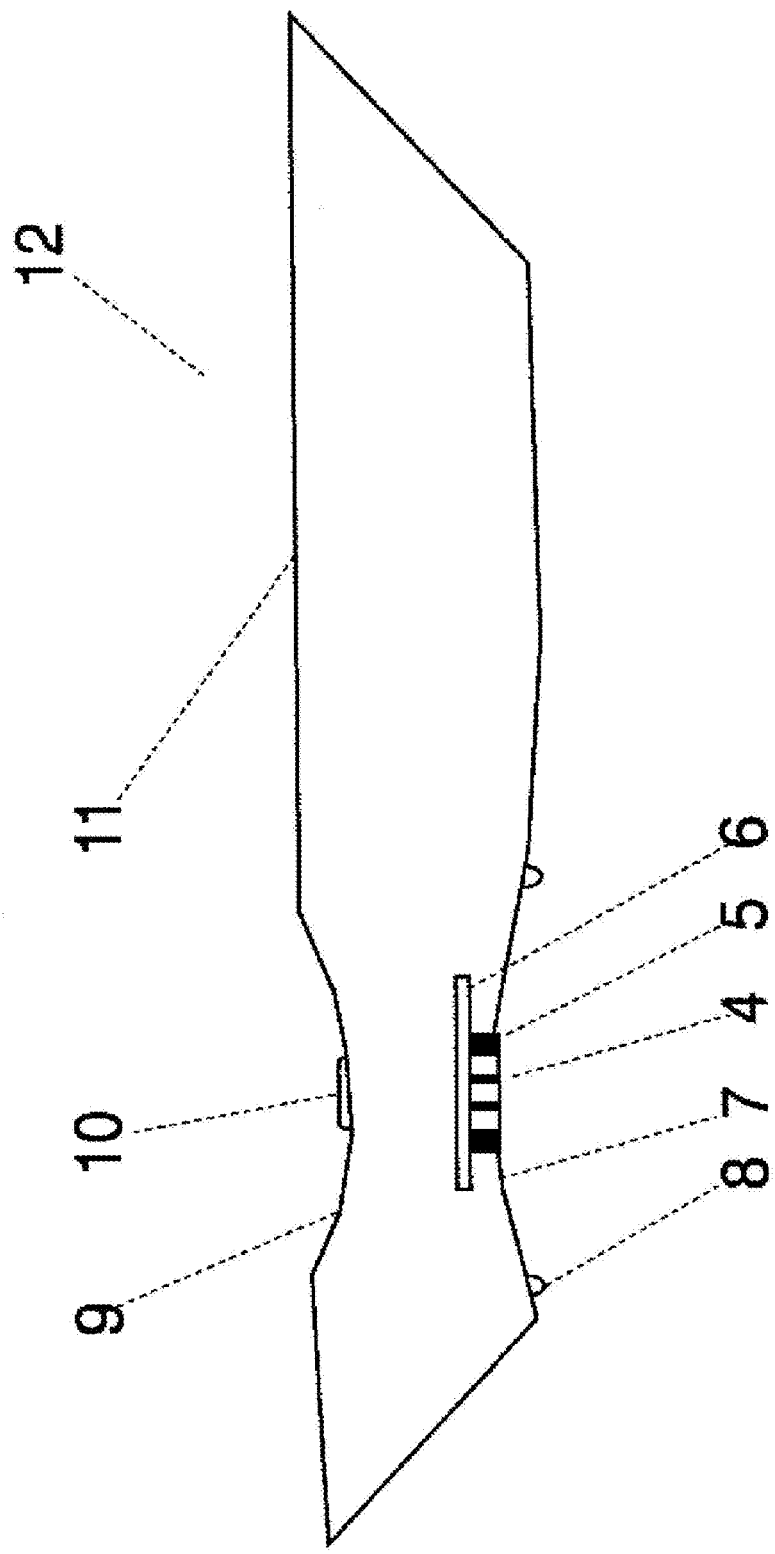

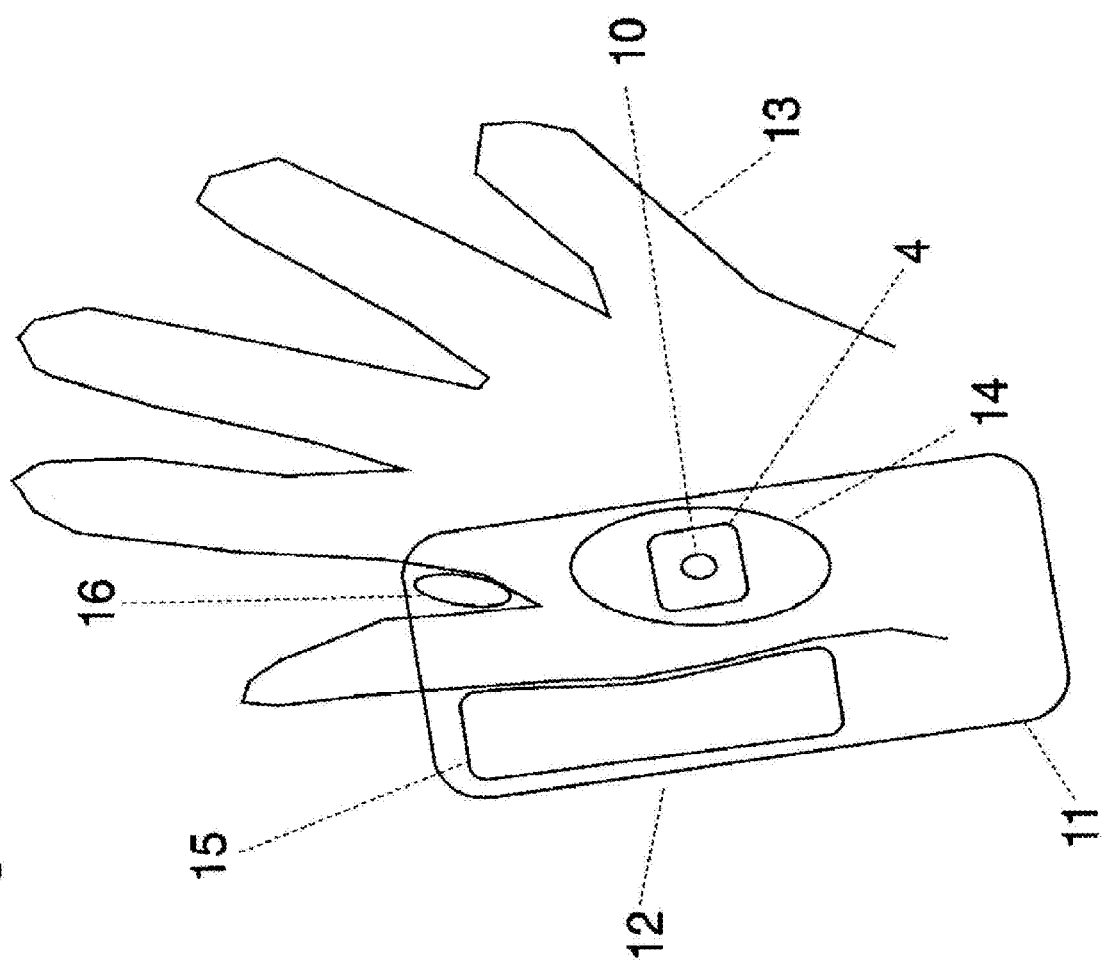

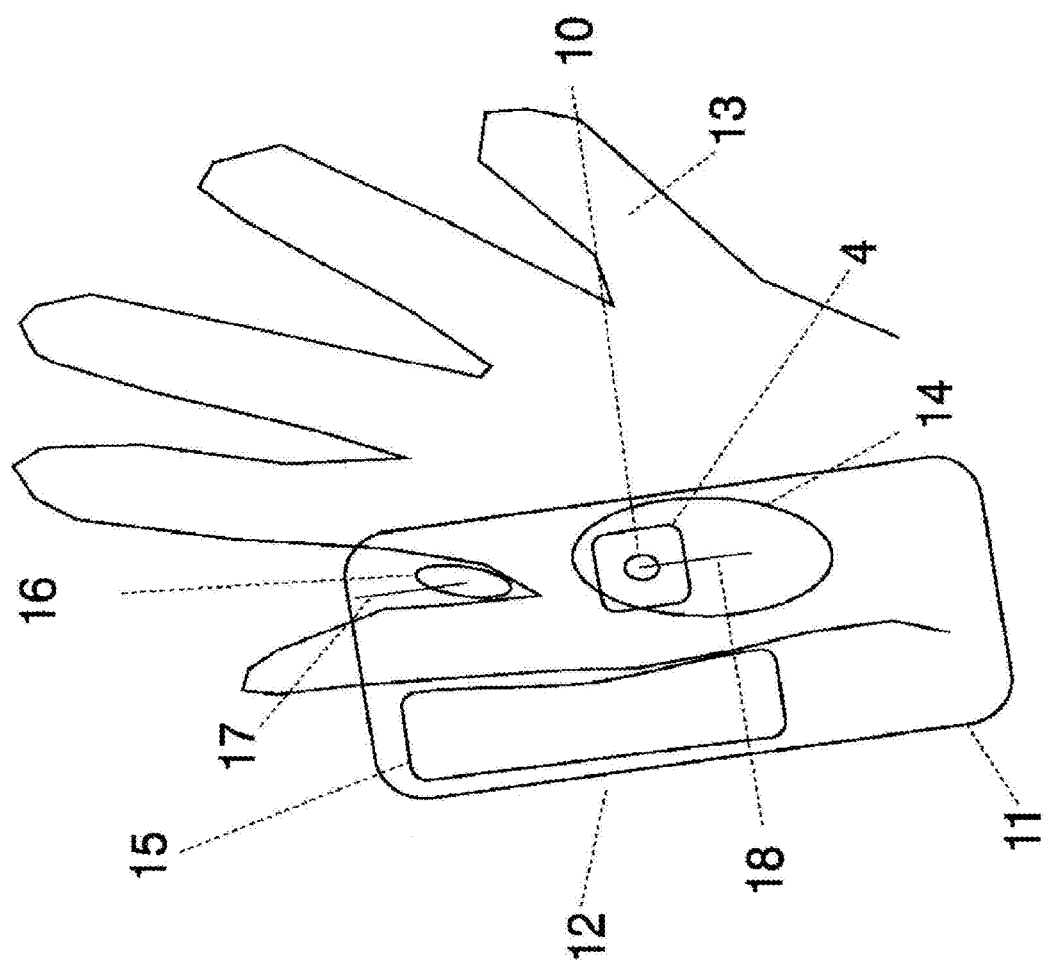

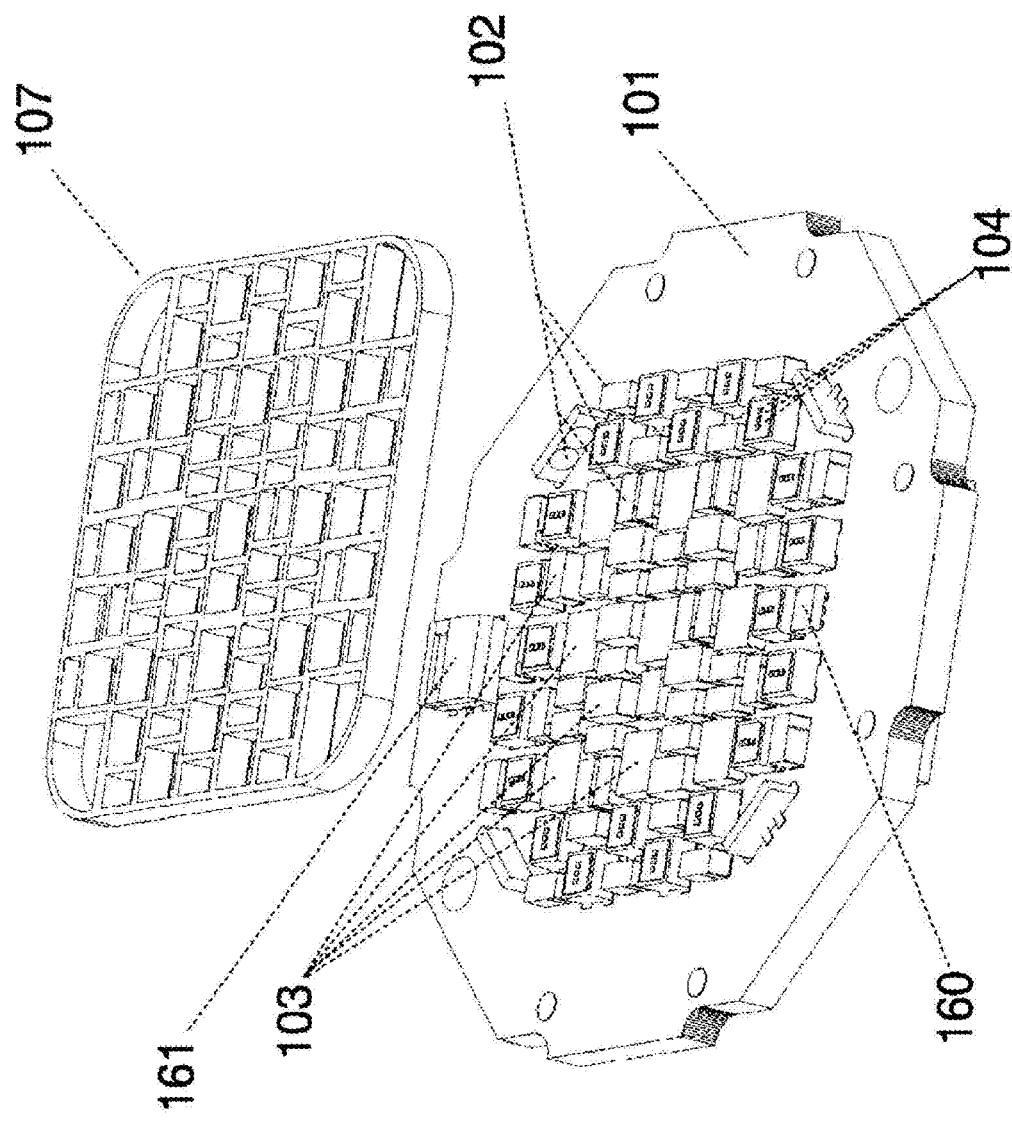

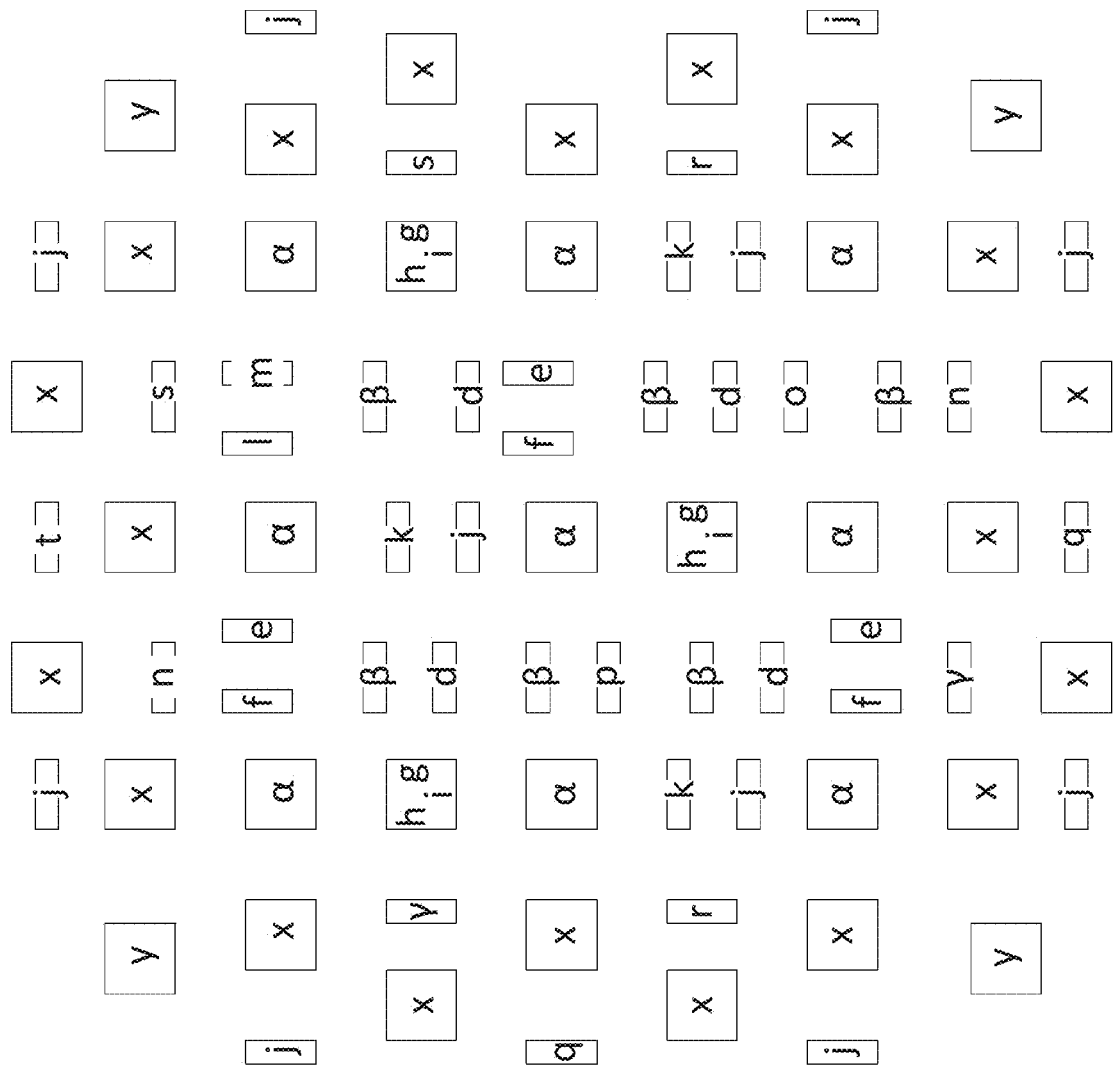

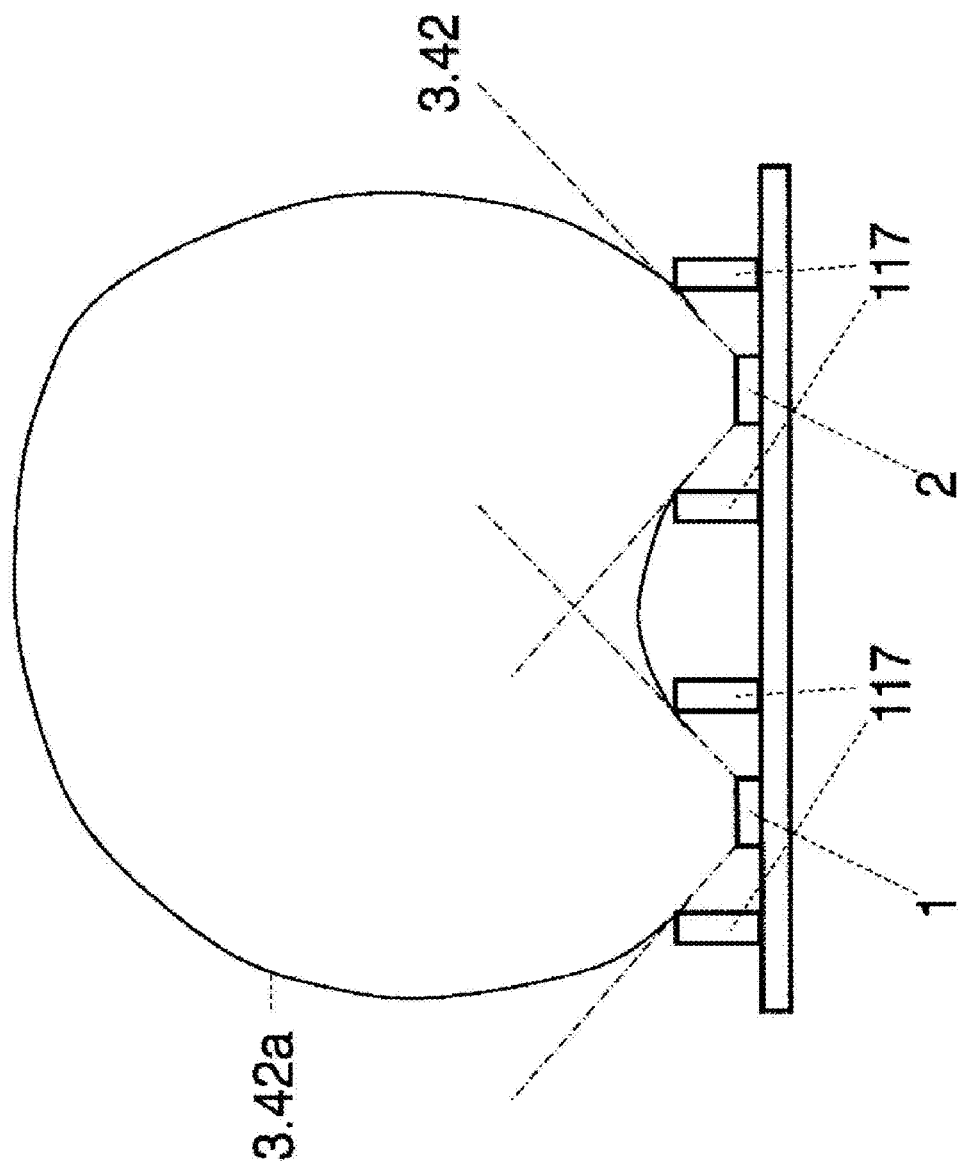

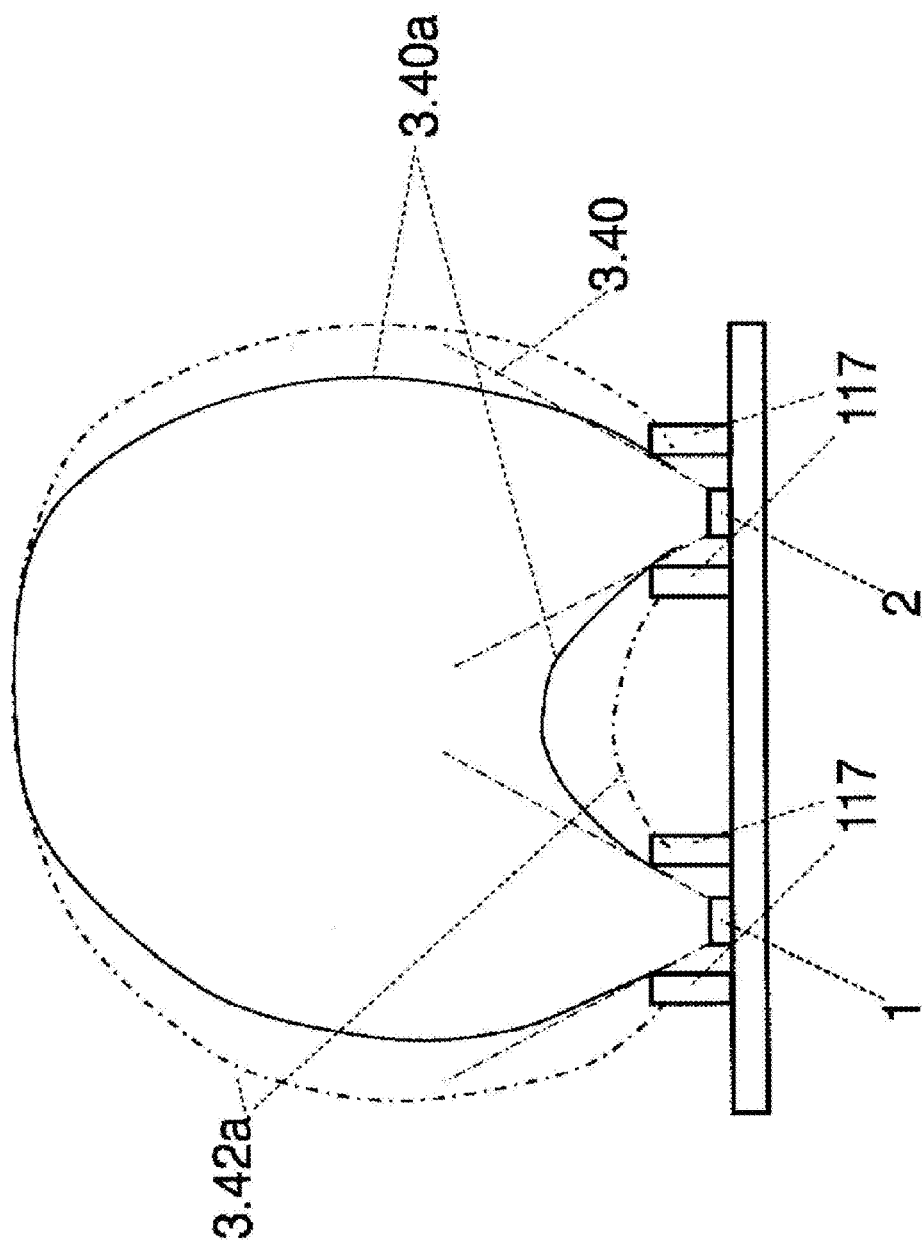

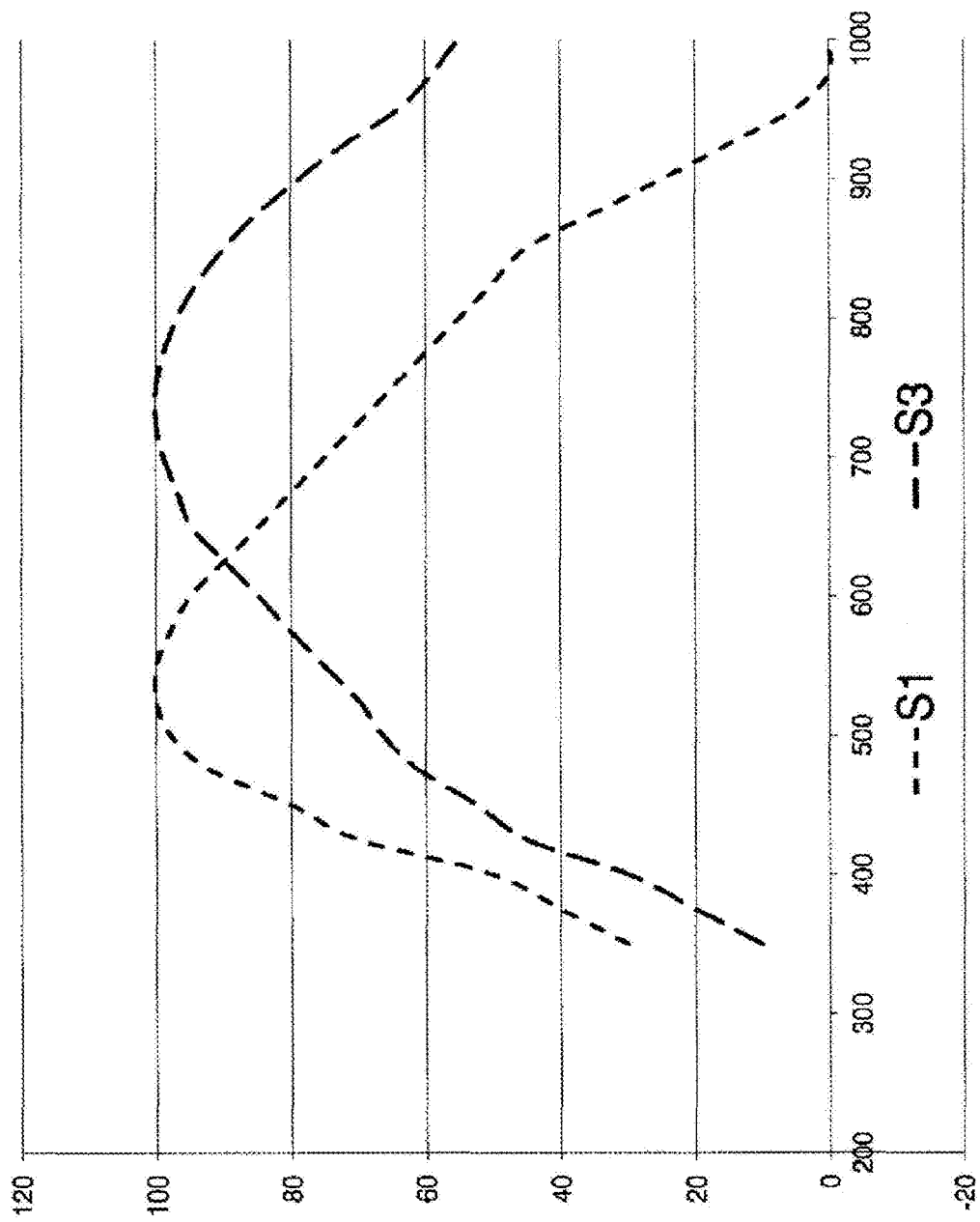

Fig. 19d 530 nm
565 nm
605 nm
684 nm
708 nm
796 nm

DEVICE AND METHOD FOR DETERMINING A CONCENTRATION IN A SAMPLE

CROSS-REFERENCE TO RELATED APPLICATIONS

This application is a continuation of U.S. patent application Ser. No. 15/109,658, filed Jul. 5, 2016, and titled "DEVICE AND METHOD FOR DETERMINING A CONCENTRATION IN A SAMPLE," which is a national stage application under 35 U.S.C. § 371 of International Patent Application No. PCT/EP2014/078466, filed on Dec. 18, 2014, and titled "DEVICE AND METHOD FOR DETERMINING A CONCENTRATION IN A SAMPLE," which claims priority to German Patent Application No. 10 2014 100 112.5, filed on Jan. 7, 2014, and German Patent Application No. 10 2014 101 918.0, filed on Feb. 14, 2014. The International Patent Application was published in German on Jul. 16, 2015 as PCT Publication No. WO 2015/104158. The entirety contents of each of the above-identified applications are hereby incorporated by reference herein and made part of this specification for all that they disclose.

BACKGROUND

There are known arrangements and apparatuses for optical in vivo measurement of analytes in samples, such as biological tissue. They are based on spectroscopic procedures in which light is radiated into the sample, passes through it and emerges from the sample at a different location. The attenuation of light resulting from absorption and dispersion is measured at the point of exit by a detector. Using appropriate reference measurements, the concentration of analytes can be determined from this measurement.

Since the detected signal is dominated by the dispersion, particularly in biological tissue, procedures are used to separate absorption and dispersion. They have spatially separated detectors to which each is assigned at least two emitters at different distances, which creates multiple emitter-detector pairs which can be compared with each other in regard to their distances. If this takes place for one or multiple wavelengths, the concentration of the analytes can be determined with a special computation of the measurements. An example of such an arrangement is described in DE 4427101 (Hein).

Different optical path lengths are often measured. The properties in a location in the sample to be examined can be concluded based on shorter and longer optical path lengths from the comparison of measurement results.

This procedure is known and disclosed under the SRR Method.

The preliminary processing of measurements is a common practice, e.g. with differential measurements between light and dark measurements with pulsed lighting or with the averaging of multiple measurements.

Procedures that weight the measured light intensities with $1/r^2$ (r=distance between LED and optical receiver) or logarithmically weight the light intensity are also common practices.

A comparison of different wavelengths by subtraction or formation of quotients is also common.

The weighted summation of processed measurements obtained in this manner in order to be able to deduce the concentrations of specific substances in the sample to be examined is also common practice.

The determination of weighting factors of the evaluation algorithm in order to adapt the output values of an evaluation algorithm with measured raw data to measured reference data is also common practice.

It is also common that such reference data can originate from test subjects and from artificial phantoms.

The transfer of calibration data of a measuring system using skin phantoms to a second measuring system is also common practice.

The indicated procedures have not been suitable for far-reaching commercial application, e.g. for measurement on human skin tissue. This is due to the fact that the quality of the measuring method is inadequate. Some approaches have already been proposed as a solution. An attempt was made to eliminate the surface inhomogeneity of the tissue with a specific computation, e.g. U.S. Pat. No. 7,139,076 (Marbach). In this approach, the assumption was that the irradiation of light on the tissue is rotationally symmetrical for all solid angles and can be received by the detector in the same manner.

With targeted irradiation of the light on the tissue with an angle of incidence of 5° to 85° to the surface of the tissue, DE 10163972 achieves better homogeneity conditions for the measurement and thus a more precise measurement result. Whereas WO 94/10901 (Simonson page 19) assumes that the detection angle for measurement has no significance, DE 10163972 describes that the result improves when the detection also takes place at an appropriate exit angle from the tissue.

Particularly with respect to the repeat accuracy of successive measurements, the inhomogeneity of tissue and surface structure and the inhomogeneous distribution of analytes in the sample pose a problem that cannot be solved with the known procedures and apparatuses. With repeated application of the device on the region of the tissue to be measured, a variation of the measuring location takes place automatically, which results in measurement deviations. Elaborate measurement location determination and relocation techniques that enable positioning of the device on an early measuring position are technically complicated and expensive. Therefore, the use of such techniques is only beneficial and possible in laboratory conditions. They are not an option for real-life use. Tissue areas with a different concentration of the analyte and changed dispersion centres are also analysed in real-life use with repeated measurement. This variation also unavoidably leads to a changed measurement result even with exact determination of the concentration. A measurement result owing to the inhomogeneity of the distribution of analyte cannot be compared with earlier measurement results. Therefore, there is no clear answer to the question of whether the concentration of analyte has increased, decreased or remained constant. Consequently, no diagnosis can be derived from the result of such series of measurements for medical applications. As a result, monitoring of concentration values is not beneficial with such a device.

There are additional problems with the anisotropy of the examined sample. The surface structure, cell structure and, for instance, blood vessels, are causes for the anisotropy of the sample. The majority of the known devices provide measurement values that depend on the angle of application of the device on the sample. This also leads to measurement deviations under real-life conditions.

There are additional problems with the detection of a specific substance, for instance, human tissue, in which a considerable number of substances that also have an effect on the optical signals used for the detection must also be taken into consideration. These substances also contribute to falsification of the measurement result. The quantity of these substances in the sample can vary greatly and also very rapidly. For instance, with heavy or light application pressure of the sample on the device, there is more or less blood in the tissue, which clearly makes the measurement pressure-dependent with known analytical processes.

Therefore, a device and method that determine a correct and stable measurement result for the concentration of the relevant analyte or analytes are needed. In the process, boundary conditions such as the inhomogeneity of the sample, the anisotropy of the sample, the presence of a multitude of substances in the sample and varying conditions in the measurement environment must be tolerated. The differences between repeated measurements must be so slight that they do not significantly affect the measurement result.

SUMMARY

An aspect of the present invention is to determine the concentration of an analyte in conditions that can be obtained in real life which do not lose their representative nature for the sample even with repeated application of the device on the sample and with which the concentration can be determined with good reproducibility using the inventive method and device. The system should also be technically unelaborate, portable and affordable to produce.

In an embodiment of the present invention, a device for optical detection of analytes in a sample includes at least two optoelectronic components. The optoelectronic components include at least one optical detector configured to receive a photon and at least one optical emitter configured to emit a photon. The at least one optical emitter includes at least three optical emitters disposed in a flat, non-linear arrangement, and the at least one optical detector includes at least three optical detectors disposed in a flat, non-linear arrangement. The at least three optical emitters and the at least three optical detectors include at least three different wavelength characteristics.

BRIEF DESCRIPTION OF THE DRAWINGS

The present invention is described in greater detail below on the basis of embodiments and of the drawings in which:

FIG. 7 shows an example cross-section of a device housing;

FIG. 8 shows a housing with positioning aids for measurement on the ball of the thumb of the hand;

FIG. 9 shows a housing with positioning aids for targeted movement of the device on the surface of the measurement object;

FIG. 10 shows an example configuration of the device;

FIG. 10a shows an example arrangement of emitters and detectors;

FIG. 18d shows a directional characteristic implemented by using a rectangular shape;

FIG. 18e shows a directional characteristic implemented by using a rectangular shape;

FIG. 19b shows an increase of spectral resolution by using combinations of different optical emitters with different optical detectors;

FIG. 19d shows an increase of spectral resolution by using combinations of different optical emitters with different optical detectors.

DETAILED DESCRIPTION OF CERTAIN EMBODIMENTS

Figure 2:
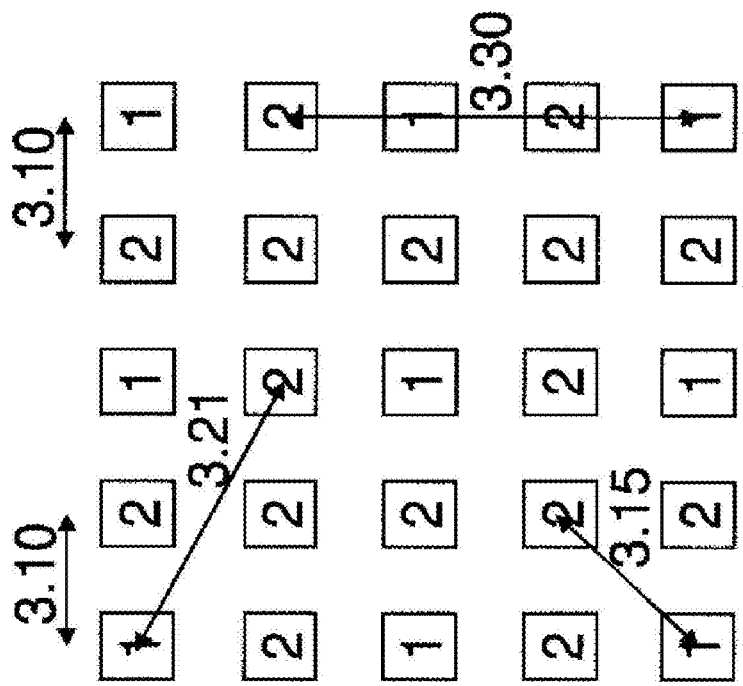
FIG. 2 shows an emitter-detector arrangement in the form of a matrix.

If the inhomogeneity of a sample is a problem, the person skilled in the art often solves this by conducting multiple measurements at different locations on the samples. This can take place with successive measurements, which often makes the measurement time-intensive, making it unbearable for economic or comfort reasons. One approach is to integrate several emitters and detectors that are arranged side by side in one measuring device. Corresponding publications can also be found for the indicated application case.

For consideration of the inhomogeneity in the depth of the sample, there are approaches that work with different distances between light emitters and light detectors, but must be greatly improved in order to be useful.

For the approach to the problem of anisotropy, several measurements at different angles would be a possible solution.

For detection of interfering substances, lighting with a larger number of monochromatic light wavelengths is known. A spectroscopic examination of the light exiting the sample is also a known solution for determining the influence of interfering substances.

However, it is not possible to combine these techniques, because a multitude of measuring lengths would be required. Since the device for analysis of the sample cannot be larger than the sample itself, and because detectors and emitters must have certain areas in order to function, there is, despite advancements in miniaturisation of microelectronics, no known solution for integrating a sufficient number of measuring path lengths, light emitters having different wavelengths and different orientations of measuring paths in the device required for the measurement.

The invention explained here describes how the problem can be solved and which method can be used for operation of the device.

The inventive approach for optical detection of analytes in a sample is characterised in that the device has three emitters for emission of photons in a planar arrangement, not in a line, and at least three detectors for receiving photons in a planar arrangement, not in a line, and that the emitters and/or detectors have at least three different wavelength characteristics.

The terms 'photons' and 'light' are used synonymously in the scope of this document.

With a suitable planar arrangement of light emitters and detectors, multiple use of components is made possible. This multiple use makes it possible to succeed with a lower total number of emitters and detectors.

According to the invention, with the arrangement of components on the plane, a large number of different distances between emitters and detectors can be achieved with a relatively low number of components. The optical properties at multiple, significantly different points can be determined as a result. Measurements with different orientations can also be carried out as a result. In addition, a high spectral resolution can be achieved with a reduced number of components.

With use of a measuring circuit according to the invention, an additional increase in the amount of information is achieved without the need to increase the number of optical components. The circuit has a very high dynamic range that permits use of longer and shorter optical path lengths than is possible with circuits having comparable technical difficulty, causing the number of usable light emitters and light detector pairs to increase while the number of light emitters and light remains the same.

With beneficial optical geometry, the amount of information is further increased and the measurement result becomes more precise. With a direction-dependent variable emission characteristic, a determination of the analyte can also take place with a concentration that varies in the depth of the sample. As a result, the measurement result can be further improved.

With a method for combining emitters having different wavelength characteristics with detectors having different wavelength characteristics, a high spectral resolution of the measurement is achieved with a low number of components. Therefore, it is possible to reduce the influence of substances in the sample that manipulate the measurement value.

Furthermore, a method is explained with which the evaluation of the indicated multitude of information is implemented in an advantageous manner.

With a combination of the evaluation process with the inventive arrangement of the measuring device, a usable measuring system can also be practically implemented in real-life environments. With a combination of the indicated method, it is surprisingly possible to incorporate all components required for a repeatable precision of the measurement on the available surface limited by the sample. The inventive measuring system is even small and compact enough that it can be integrated in real-life objects or also be used as a portable pocket-sized device.

In an advantageous version, the system can be arranged as an electronic printed circuit board and does not require any optical fibres. Therefore, it can be realised affordably in a small format.

It is surprising for the person skilled in the art that a symbiosis between the two approaches is created, which still does not have a significant influence on the overall system with a slight increase in the number of components. However, if a system is designed according to the rules below, the symbiosis for larger numbers of components increases disproportionately and the demands explained at the outset can thus be resolved on the surface available for the optoelectronics.

The intended generation of this symbiosis and the resulting possibility of generating a basis of information increasing disproportionately in quantity and quality in relation to the number of emitters and detectors that are used together with the method of this basis of information to be evaluated are the most important basic ideas of the present invention. In order to achieve the desired symbiosis, it is advantageous to exceed a number of components specified further below in the text and to follow the specified geometric arrangement rules.

The solutions addressed in the preceding text are explained in detail below.

According to the invention, the device consists of at least three emitters in a planar arrangement that are not in a line and at least three detectors in a planar arrangement that are not in a line and the emitters and/or the detectors have at least three different wavelength characteristics.

In a preferred variant, there are at least six emitters in a planar arrangement that are not in a line and, additionally preferred, at least six detectors in a planar arrangement that are not in a line and the emitters and/or the detectors preferably have at least three different wavelength characteristics.

In an alternative variant, there are at least 50 or 100 emitters in a planar arrangement that are not in a line and preferably at least four or eight detectors in a planar arrangement that are not in a line and the emitters and/or the detectors preferably have at least three or five different wavelength characteristics.

The device preferably comprises at least two or three detectors having different wavelength characteristics and at least two or three emitters having different wavelength characteristics. The wavelength characteristics are preferably wide-band, such that more different wavelength characteristics can be created by combining different emitters with different detectors than the larger number of detectors or emitters of different wavelength characteristics.

The device preferably consists of pairs that each have an emitter and a detector that have an approximately equal distance between emitter and detector and approximately equal wavelength characteristic. In the scope of this document, the term 'equal emitter detector pair' or 'equal pair' or 'group of equal pairs' preferably refers to multiple emitter-detector pairs that each have exactly one emitter and exactly one detector and having an emitter-detector distance that is approximately the same and that have approximately the same wavelength characteristic.

The terms 'equal pairs' and 'comparable pairs' are used synonymously in the scope of this document.

It is preferred that the emitters and/or detectors are members in at least two, preferably at least six such pairs.

At least one emitter and/or detector or multiple emitters and/or detectors or all emitters and/or detectors are members in at least two or at least six different groups of equal pairs.

The device preferably comprises equal emitter-detector pairs having connecting lines that do not exclusively run in parallel.

The device preferably comprises equal emitter-detector pairs—preferably also at least equal emitter-detector pairs—in which the orientation of connecting lines with a virtual intersection on a two-dimensional plane results in an acute angle of 30° to 45° or preferably an angle of >45° and especially preferably an angle of 90°.

The emitters and detectors are preferably arranged such that sufficient coverage of all necessary orientations of the connecting line between emitter and detector and/or between detector and emitter is provided for the relevant values of distance and wavelength characteristic. It is especially preferred if the orientations do not differ for any angle by more than 180 degrees, preferably 120 degrees and ideally 70 degrees. It is especially preferred if between 3 and 5 orientations are created, preferably between 4 and 8 orientations, that are distributed approximately equally on the angle scale. Since this cannot always be achieved due to additional boundary conditions according to the invention, in a preferred arrangement, at least one arrangement is selected for at least one part of the groups of comparable optical paths in which there is at least one connecting line within each angle range of a defined angle sector width, wherein the orientation of said connecting line falls within the angle range. The width of such an angle sector is no higher than 180 degrees, preferably 120, 70, 50, 20 or even 10 degrees.

The device preferably consists of emitter-detector pairs—preferably also equal emitter-detector pairs—that satisfy a surface-based distance criterion and/or a volume-based distance criterion and/or an orientation-based distance criterion. Preferably, multiple or all equal emitter-detector pairs satisfy one or multiple of these distance criteria.

The device preferably comprises a device for influencing the emission direction of the photons emitted by the emitters.

The device preferably comprises a device with which the influence of reception directional characteristics of the detectors takes place.

The device preferably comprises means that produce the effect that the photons emitted by the emitters and/or the photons detected by the detectors are not emitted and/or detected rotationally symmetrically.

The device is preferably configured such that the photons emitted by the emitters are essentially emitted at an angle between 5° and 90° to the plane on which the emitters and detectors are located and are essentially received at an angle between 5° and 90° to the aforementioned plane of the detectors.

The device preferably comprises emission and detection angles that are produced by a rectangular geometry of emitters, detectors and/or photon guide elements.

The device is preferably configured such that different directional characteristics in the sense of a far field radiation/receiving pattern are achieved through different orientations of the components and/or chips of the emitters and/or detectors to the plane spanned by the emitters and detectors.

The device is preferably configured such that different directional characteristics are achieved by refracting and/or diffracting and/or reflecting and/or shadowing the emitted and/or detected photons.

The device is preferably configured such that, for at least one wavelength the distances between the detectors and emitters provided for said wavelength in the range of distances between detectors and emitters that are short enough for use are arranged in a finer gradation than for a different wavelength, wherein the distances are shorter than the other wavelength by a factor of 0.9 or 0.8 or 0.6 or 0.3.

The device preferably comprises optoelectronic components arranged in a manner such that length differences for a wavelength arise which are smaller than the detector size, the emitter size or the distance from detector to emitter, and particularly such that the optical path length differences are only 50% or 20% or 10% or even 5% of these sizes.

The device preferably comprises optoelectronic components that are arranged such that distances between detectors and emitters arise, said distances having length differences that are less than twice the detector distance, less than the single detector distance or less than 55% of the detector distance.

The device preferably comprises optoelectronic components that are arranged such that the number of significantly different distances between detectors and emitters is greater than the number of detectors or the number of emitters or the sum of both. 'Significantly different' means that the optical paths differ by at least an amount that is greater than the closest distance between two detectors or the closest distance between emitters or the larger of these two values or the sum of these two distances. In an advantageous variant, said distance between components is defined by the distance between the areas associated with these components where the light enters or exits the sample. In an advantageous variant there is opaque material in the region of this distance.

The device is preferably configured such that the surface of the arrangement is not planar or is comprised of multiple detector elements having different orientations.

The device preferably comprises some optical components that are arranged such that they can be moved with respect to other optical components.

The device is preferably configured such that the device has a contact surface that can be brought into direct contact with the sample to be measured.

The device is preferably configured such that it is suitable for coming into contact with biological material, particularly human or animal tissue. In an advantageous variant it consists of material that is easy to clean. In an advantageous variant it consists of material that is highly resistant to chemicals.

The device is preferably configured such that the control electronics of at least a part of the emitters has a matrix structure.

The device is preferably configured such that the control electronics of at least a part of the detectors has a matrix structure.

The device is preferably configured such that the detectors have a dynamic range of at least 1:100, a particularly preferable range of at least 1:50,000, additionally preferable range of at least 1:1,000,000 and further preferable range of at least 1:10,000,000.

The device preferably comprises evaluation electronics that enable the aforementioned dynamics.

The device is preferably configured such that the emitters and/or detectors comprise semiconductor elements.

The device is preferably configured such that the semiconductor elements are positioned no further than 50 mm, preferably no further than 6 mm and particularly preferably positioned at a distance of less than 1.5 mm from the sample when the device is in its measuring position.

The device preferably comprises sensors and/or data interfaces for additional environmental conditions and/or physical or chemical parameters and/or living circumstances of the sample belonging to the organism.

The device preferably comprises means for influencing the measurement and/or environmental conditions, particularly heating, drying and/or contact pressure application devices.

The device is preferably configured such that it can be integrated into devices that have different functionalities and belong to the following group of devices: smart phone, household appliance, personal scale, vehicle steering wheel, article of clothing, jewelry, tool, handle, furniture, toilet seat, input device.

In a preferred variant, the device is integrated in an object with which the user regularly comes into contact.

The device preferably comprises means for positioning relative to a sample.

The device is preferably configured such that it enables the detection of carotenoids and/or antioxidants and/or blood constituents and/or substances appearing in human or animal tissue and/or physiological relationships and/or liquid and/or solid and/or gaseous substances.

With the inventive method for optical detection of analytes in a sample, particularly consisting of animal or human tissue, photons are radiated into the sample by at least three emitters arranged on a plane and not in a line. A portion of these photons exiting the sample is detected by at least three detectors arranged on a plane and not in a line, wherein the pairs of emitters and detectors that are used have at least three different wavelength characteristics and the concentration of analyte is determined from the analysis of measurement values of the detectors using mathematical methods.

With the method for optical detection of analytes in a sample, preferably at least three emitters preferably arranged on a plane radiate into the sample. The emitters preferably have different wavelength characteristics and are preferably not arranged in a line. The photons exiting the sample are preferably detected by at least three detectors which preferably have different wavelength characteristics. The concentration of analyte is preferably determined from the analysis of the photons exiting the sample using mathematical methods.

It is additionally preferred that a method in which the photons that are emitted by an emitter—preferably exactly one emitter—are detected by at least two detectors having different wavelength characteristics and/or the photons emitted by at least two emitters having different wavelength characteristics are received by exactly one same detector.

Preference is furthermore given to a method that uses a mathematical result calculated from the detected photons of various emitter-detector pairs that have an approximately equal distance and approximately equal wavelength characteristics to determine the concentration of analyte.

Preference is furthermore given to a method that uses a mathematical result calculated from the detected photons of various emitter-detector pairs that have an approximately equal distance and approximately equal wavelength characteristics and radiation/receiving patterns with comparable effect to determine the concentration of analyte.

Preference is furthermore given to a method with which representative values are determined for emitter-detector pairs having approximately equal distances and equal wavelength characteristics and, in an advantageous variant, additionally with directional characteristics having a comparable effect—preferably for at least almost all emitter-detector pairs having approximately equal distances and approximately equal wavelength characteristics and/or comparable directional characteristics—and the concentration of an analyte in the sample is determined and from these values.

Preference is furthermore given to a method that determines the concentration of the analyte in the sample at different points using the amount of received photons at different wavelength characteristics and/or various optical path lengths detected by the detectors. The total concentration of the analyte is then determined in consideration of the measurement values for the various locations.

Preference is furthermore given to a method with which the photons emitted by at least two emitters having different wavelength characteristics are detected by at least two detectors having different wavelength characteristics, so that measurement values are produced which have a number of wavelength characteristics that is greater than the larger number or the sum of the different wavelength characteristics of the emitters and the detectors.

Preference is furthermore given to a method with which emitter-detector pairs having approximately equal distances and approximately equal wavelength characteristics are averaged or mathematically combined with each other in other ways, wherein said pairs satisfy a planar and/or spatial and/or orientation-based criterion.

Preference is furthermore given to a method with which values are recorded multiple times in succession in order to detect and/or eliminate changes and/or fluctuations in the sample.

Preference is furthermore given to a method with which optical paths having different lengths between the emitters and detectors and/or different locations and/or different emission characteristics are used and for which the respective optical path measurement values are recorded. It is preferable that the properties of the sample can be concluded depending on the depth below a point on the surface by using mathematical operations on the measurement values of these optical paths.

Preference is furthermore given to a method that compares the individual measurement values of a group of equal pairs or combines them with each other with mathematical operations and determines a value characterizing the fluctuation range of said pairs.

Preference is furthermore given to a method with which at least some of the emitters and/or detectors are used to determine measurement values at more than one measurement location.

Preference is furthermore given to a method with which the groups of pairs having approximately equal distances and approximately equal wavelength characteristics are formed in which the emission and detection angle of the emitter-detector pairs also have equal characteristics.

Preference is furthermore given to a method with which the exposure time of the detectors corresponds to a multiple of the half periods of the mains frequency.

Preference is furthermore given to a method with which the quantity of photons detected by a detector is measured, wherein the current through the optical detector is measured by discharging a capacitor and measuring the degree of discharge and/or the number of discharging cycles within a short time and/or combining this with the measuring the current directly.

Preference is furthermore given to a method with which at least two of the aforementioned methods for measurement of current are used.

Preference is furthermore given to a method with which the selection of the measuring methods which is used to measure the current through the detector takes place automatically during the measurement. The selection of measuring methods preferably takes place without the amount of the measurement value to be expected being known before the beginning of the measurement.

Preference is furthermore given to a method with which the measurement in each measuring mode takes place over a predefined time period independently of the measurement value.

Preference is furthermore given to a method with which the fluctuation range of measurement values is determined by a sequence of measurements in order to determine the minimum number of measurements necessary for the respective sample, which minimises the deviations of measurement results with successively conducted measuring cycles.

Preference is furthermore given to a method with which additional information, such as temperature and air humidity of the environment, temperature of the sensor and/or the sample, is factored into the evaluation.

Preference is furthermore given to a method with which information pertaining to the sample and the organism belonging to the sample is also processed with the further processing of values obtained in the measurement process. In particular, history of feed and/or nutrition compositions, the quantity and history of stress situations, illnesses or environmental conditions are taken into consideration.

Preference is furthermore given to a method with which the individual belonging to a sample can be differentiated with a certain probably from another individual by comparing the measurement results obtained from the sample of another individual.

Preference is furthermore given to a method with which the measurement results are determined with an algorithm and algorithmic elements and/or constants of the algorithm are determined with iterative calculations, preferably using a data processing system.

The arrangement can have various light emitters in an advantageous manner, e.g. with various spectral characteristics.

The arrangement can have various detectors in an advantageous manner, e.g. with various spectral characteristics.

Preference is given to a rule for selection of positions of emitters and detectors specified below, according to which it can be determined how closely the illuminated regions of different pairs of emitters and detectors may be arranged in order to maintain a high increase of obtained information with an increase of the number of such pairs. The purpose of the rule is, among other things, to spare the pairings that are not necessary according to the rule in order to utilise installation space for, e.g. an improved spectral resolution. The methods explained here have a very close mutual interaction and cannot always be applied individually, as they need to be applied to the same geometric arrangement. However, in order to make the description clearer, the aspects must first be explained individually.

In an advantageous approach to the representative detection of the inhomogeneity of a sample, the arrangement and distribution of emitter-detector pairs on a two-dimensional surface is configured such that there are emitter-detector pairs in which the path corresponding to a directly connecting line between emitter and detector are also approximately equal. As already mentioned, such emitter-detector pairs are preferably identified as equal emitter-detector pairs. An approximately equal wavelength characteristic, for instance, is provided when the differences between two emitters are no greater than the production-related variation for each emitter. In the scope of this document the distances of two pairs is called an approximately equal distance between emitter and receiver, when the difference from the average path length of the two distances is a maximum of 30%, preferably a maximum of 20%, more preferably a maximum of 10% and ideally 5% or less. A group of pairs of approximately equal wavelength characteristics and approximately equal distance consists of two or more emitter-detector pairs. The more groups there are and the more emitter-detector pairs that belong to a group, the better the inhomogeneity of the sample can be detected.

Preference is given to a variant in which the definition of which emitter-detector pairs are to be considered as sufficiently equal for membership in a group of equal pairs is expanded with aspects of orientation of the emitter/detector connection line and/or the preferable orientation of the paths of movement of photons and/or aspects of the directional characteristics of emitters and detectors. For the sake of linguistic simplicity, the explanation below usually only addresses an approximately equal distance and wavelength characteristic, because it is clear to a person skilled in the art after mentioning the other criteria indicated above how to apply them analogously.

Photons that wander from the emitter towards the detector pass through a three dimensional space in the sample. The probability of presence in a location in this space is related to the distance of this location from the direct connecting line between the two. At a large distance from this line, there are fewer photons than at a small distance.

With the examinations for representative consideration of the inhomogeneity of a sample, it could be determined in a surprising way that with the distribution of emitters and detectors having approximately equal emitted wavelength characteristics on a two-dimensional surface, the space through which photons wander can be taken into consideration in addition to the distance of emitters and detectors in order to optimise the measurement result.

Preference is given to an approach with which the spaces through which photons wander at least 5%, preferably at least 20%, more preferably at least 50% and even more preferably at least 80% and ideally at least 95% should not overlap.

Preference is given to a configuration of the invention in which the installation spaces that arise with the use of the distance criterion for components are used in order to position components having different wavelength characteristics.

The degree of overlapping of the spaces can be determined as follows:

Initially, the probability of the presence of a proton for each optical path to be considered between emitter and detector is determined for each spatial element of the sample. In an advantageous variant, this value is then based on a reference variable. This can, for instance, be the average probability of residence of an equal-size volume element of the overall sample belonging to the same optical path, or also the maximum probability of residence of a photon on a volume element of the central plane between emitter and detector or also a constant. A characteristic is determined from the characteristics obtained for each volume element from the probability of residence, on the basis of which it is determined whether the volume element belongs to the optical path or not. This decision can be binary, but also analogue. With volume integration over the sample volume, the volume of the optical path can be calculated. For a comparison of two emitter-detector pairs, the volume of the optical path is calculated separately for each pair. Then the volume of the overlapping region is determined. This can, for instance, take place with product formation of the membership characteristics of the volume elements for the individual pairs. Alternatively, a table that defines the membership to the overlapping region depending on the two membership characteristics with respect to the two emitter-detector pairs in consideration. Volume integration yields the size of the overlapping region between two pairs.

If the volume of the overlapping region is compared in relation to the volume of the optical path of one of the two pairs, the overlap is represented as a percentage. The overlapping limit values specified above can be applied for this.

It is still important that the specified overlapping limit values cannot only be applied for each individual optical path pair, but can instead be applied in an averaged consideration of all optical paths of a comparable group.

The overlap of a volume element can be defined in an advantageous variant for the pairings of each pair with every other pair and then be used to calculate an overlapping overall characteristic of the volume element. This can, for instance, take place with formation of the maximum value or summation of the analyses in pairs. With volume integration of the overall characteristic, the size of the overall overlapping region can be determined. With volume integration of the volumes belonging to an optical path, an overall characteristic is obtained for the volume of the optical paths. These can be compared in relation to each other in order to obtain an overlapping limit value to which the criterion mentioned above can be applied.

In an advantageous variant the criterion for selected groups with comparable emitter-detector pairs is carried out individually.

In an alternative advantageous variant the criterion for selected groups with comparable emitter-detector pairs is carried out for groups.

The method describe above for determining the overlapping characteristic is identified as a volume-oriented distance criterion.

In an advantageous variant, the movement directions of photons are also taken into consideration. If they are significantly different, a reduced overlapping characteristic is calculated despite a high probability of residence of photons. As a result, better consideration of the anisotropy of the sample is achieved, as explained in another part of this document. This method is identified as an orientation-based distance criterion.

In a simplified process for determining and checking the overlap, the three-dimensional space through which the photons wander from the location of radiation to the location of their detection, projected on the plane on which the emitters and detectors are located. A surface on this plane is determined for each emitter-detector pair on which all points of the surface have a distance of at least 0.2 mm, preferably 1 mm, more preferably 2 mm, even more preferably 3 mm and ideally 5 mm to each point on the direct connecting line. Two consecutive pairs are compared with each other with respect to the overlap. The limit values mentioned above are applied to the overlapping surfaces.

In an alternative variant the spaces through which passage occurs in the surface of the emitters and detectors are represented by suitable ellipses.

The overlapping characteristic can also be applied in pairs for each two optical paths in this surface-based distance criterion. However, it is more advantageous to consider an average value for the entire group of equal pairs.

In an additional examination, it was determined in a surprising way that, with the distribution and assignment of emitters and detectors on a two-dimensional surface, the orientation of the direct connecting line between emitter and detector is important for detection of the inhomogeneity of a sample.

In an advantageous version, the distribution of emitters and detectors takes place on this surface in a manner such that emitter-detector pairs arise in which the wavelength characteristics are approximately the same, there is an approximately equal distance, the overlap of their spaces through which photons wander takes place in an inventive way and with which the orientation of their direct connecting line is approximately equal. An equal geometric orientation of emitter-detector pairs is provided when the paths of the direct connecting lines are virtually brought to an intersection while maintaining their orientation on a two-dimensional surface and the resulting acute angle is no wider than 30°. Special preference is given to a solution in which this angle is no wider than 10°.

In an additionally advantageous version, emitter-detector pairs having equal orientation are mathematically combined with emitter-detector pairs having a different orientation. The group of the other orientation includes emitter-detectors pairs that do not differ from the pairs having the same orientation with respect to their distance and emitted wavelength characteristics, but in that the virtual intersection of the connecting lines results in acute angles between 30° and 45°, or preferably over 45° and running ideally nearly perpendicular to each other. The comparison provides a representative mapping of the anisotropy of the sample. As the studies demonstrated in a surprising way, the comparison achieved a high repeat accuracy of the measurements without the necessity of positioning the device in the same location of the measuring area for the repeated measurement. This circumstance is the result of the following relationship: When the measuring device having the inventive distribution and orientation of emitters and detectors is applied, the light propagates along optical paths that run in different preferred directions corresponding to the emitter-detector orientation through the inhomogeneities (in the sense of inhomogeneous volume) of the sample. As a result of these orientations in biological tissue, the light passes blood vessels and skin grooves with different angles. Consequently, the orientation in which the light passes through the tissue does not change significantly even with repeated application of the device with a possible different angle. Therefore, with a suitable evaluation, a comparable measurement result is produced even with repeated measurement.

With the number of emitters and detectors, their packing density on a two-dimensional plane, their orientation and the radiation and detection characteristics of emitters and detectors, both the measurement precision and the repeat accuracy in determining the concentration increase according to the present invention.

In an advantageous version of the invention, the measurement with the described arrangement is repeated at least once, but preferably multiple times. Preference is given to a variant in which this takes place immediately after the first measurement without removing the sample. In a different preferred variant, the sample is removed and re-applied, or an additional sample is applied. A third advantageous variant is a combination of both methods.

With comparison or by mathematically combining the multiple conducted measurements, changing components can be recognised and purposefully evaluated. The suppression of changing signal components is also possible by averaging or mathematical operations. With this process, for instance, the recognition of the pulse frequency in a living sample is possible, as well as the suppression of the measuring error caused by the pulse. With re-application of the sample, operating errors or location dependencies can be recognised and compensated for. With measurement of different samples, sample errors can be recognised and compensated for.

The term wavelength characteristic in connection with this document is to be understood such that an optical transmitter or detector or a substance through which light passes will influence or process light having different wavelengths differently. The wavelength characteristic preferably describes which wavelength is influenced in which way, especially how strongly.

Based on the example of an LED, the wavelength characteristics preferably describe the intensity of the produced light depending on the wavelength. An LED with a specified emission wavelength of 700 nm typically also emits light at 705 nm or 710 nm; however, this typically occurs at a lower intensity. LEDs can, in particular, have the same specified emission wavelength but, for instance, differ in their wavelength characteristics such that they have narrower or wider wavelength characteristics. An example of this is a 700 nm LED that still has 50% of the maximum emission at 750 nm in comparison with an LED that only has 5% of the maximum emission at 750 nm. Examples for wavelength characteristics are illustrated and explained in FIG. 19. The same applies for detectors.

In this document, the wavelength characteristic of a component does not only refer to the characteristics of the actual chip. Filters, dyes, cast materials, assembly and installation situation, conditions of use such as temperature and age, as well as optically acting elements such as thin layers or light-refracting elements that also have an influence on the wavelength characteristics are also meant in this connection, insofar as it is logical.

The joint effect of the wave characteristics of the emitter and detector are to be understood in connection with the wavelength characteristics of an emitter-detector pair.

Some emitters can emit light varying in wavelength. For instance, LEDs containing multiple chips for different wavelengths are known. Such emitters are preferably treated as separate emitters in connection with this document. Preference is given to a variant in which only one emitter is activated in the process. In an alternative advantageous variant, multiple emitters are activated simultaneously. This is advantageous, for instance, when the simultaneous measurement of multiple emitter-detector pairs enables parallel and thus quicker measurement due to slight or easily calculable overlapping of wavelength regions.

Some emitters are capable of changing their wavelength characteristics. Examples of this are, for instance, LEDs that emit different wavelengths with different operating currents. There are similar detectors that are, for instance, available with tunable filters. Preference is given to a variant in which tunable components in connection with the present description are treated such that the wavelength characteristics of the emitter-detector pair is averaged or calculated during the time in which a partial measurement takes place for a fixed wavelength characteristic. The duration of a partial measurement is thus defined in that a time sequence of measurement values is not obtained from the detector during this time.

A tunable emitter or detector can thus be virtually deconstructed and traced back to the basic idea of this invention.

In connection with this document, the term directional characteristic should be understood, in particular, as which quantity of light is emitted or received in which direction. The relationships basically apply similarly for light emitters and light detectors, as a person skilled knows, which is why the side of the light emitter is explained as an example here for the sake of simplicity.

The light emitters described in this document emit the light with varying intensity depending on the exit angle. It is important that most of the inventive embodiments do not involve rotationally symmetric systems, like the light emitters that often known in the state of the art. Therefore, the directional characteristic preferably involves a value dependent on 2 angles that characterises the strength of the light emitted in the direction of this angle. For example, this can be a specified percentage depending on the orientation angle on the plane of the light emitters and light detectors and the angle to a line perpendicular to this plane, which runs through the emitters or detectors.

The term directional characteristic is often used in the text in the relationship between light emitters and light detectors. In this case, the angle on the plane is advantageously specified such that 0 degrees corresponds to orientation towards the other respective components and deviations from this direction are detected in the range of +/−180 degrees.

It can be beneficial for a simplified representation to specify the directional characteristic of a light emitter to a light detector or vice versa purely as a function of the angle to a line perpendicular to the emitter-detector plane through the component in the direction of the respective partner component. Simplified even more, this can be referred to as a steep or flat directional characteristic towards a corresponding partner component. Flat means, in particular, that a relatively large amount of light is emitted such that it reaches the partner component without passing through deeper layers of the sample. Steep means, in particular, that a relatively large amount of light is emitted such that it must pass through deeper layers of the sample in order to reach the detector. Emitters and detectors are preferably interchangeable in this description. In addition the directional characteristic of a pair of light emitter and light detector can be defined as the directional characteristics of emitter and detector.

Non-transparent elements that shade the light, such as plastic or metal, can be used as means for producing a directional characteristic. In particular, they can be black or contain black pigment in order to absorb the light. Furthermore, elements that reflect light can be used. They can be reflective or diffusely reflecting surfaces. In particular, they can be also be coloured in order to create different directional characteristics for different colours. The surfaces can also be curved. In addition, transparent materials can be used to conduct light. These can be transparent plastics or glasses, in particular. They can also include dyes or colour pigments. In particular, the directional characteristic can be influenced with the introduction of elements or powders that scatter the light. Such elements can, for instance, be glass spheres, colour pigments, white pigments, white or coloured powder or paste, or air bubbles. In addition, the directional characteristic can be influenced by the delimiting surfaces of various materials and particularly by the shape of such surfaces or the surface properties. Examples of feasible delimiting surfaces in this connection would be between gas and glass, gas and plastic or glass and plastic, as well as different glasses or plastics. In particular, the directional characteristic can be influenced by lenses, diffraction grating, Fresnel lenses, thin layers, prisms or diffusion panes. The directional characteristic can also be influenced by light conductors. In addition, the directional characteristic can be influenced by the shape, size and orientation of the emitter and/or detector. This is also possible with the shape and orientation of the semiconductor, in particular. This is also possible with a casting of the semiconductor, in particular. This is also possible with the positioning of the semiconductor relative to transparent and non-transparent material elements, in particular.

In an advantageous configuration, the non-transparent materials are also used to ensure that only light from the emitter that has passed through the sample reaches the detector. Preference is given to a variant in which the non-transparent material forms a blocking element for the light and thus blocks the path from the emitter to the detector. In an advantageous variant, at least 50%, preferably at least 95% and ideally every path is blocked, in which the light must at least not pass through the sample, preferably at least a defined minimum path must through the sample. In an advantageous configuration, this minimum path is at least 2% of the distance from emitter to detector, preferably at least 20%, more preferably at least 50% and ideally at least 80%. In an advantageous variant, this requirement is partly realised with the arrangement. In an advantageous variant, this requirement is partly realised with the evaluation process. In an advantageous variant, it is assumed for the calculation that the light that passes through the delimiting surface of the sample and device more than 2 times is not considered.

In an advantageous variant, there is at least one pairing of light emitter and light detectors in which light must not pass through the sample and is reflected at least partially on the sample surface on the path from the light emitter to the light detector.

A group of similar pairs or a group of equal pairs or group of equal optical paths between emitter and detector in connection with this document should be understood as follows. A measurement can be conducted for every possible combination of emitter and detector. This takes place with activation of the emitter and emission of radiation. Preference is given to a configuration in which only one emitter is activated at a time. Preference is given to variants in which different emitters are activated in succession. The emitted radiation runs through the sample and at least partly reaches a detector. Preference is given to a version in which multiple detectors are activated simultaneously. The signal detected by a detector is the measurement value of the emitter-detector pair from the activated emitter and the detector used of the measurement. By varying the emitters and detectors, a multitude of such measurement values is produced. These measurements preferably identified as a group under certain conditions. Different group formation rules depending on the configuration of the arrangement are also possible even if only an approximately equal wavelength characteristic and approximately equal distance are explicitly specified in the description.

For this purpose, for instance, the wavelength characteristic of the emitter of an emitter-detector pair must not match that of another for an equal wavelength characteristic. It is sufficient, preferably if the jointly created wavelength characteristic of the emitter and detector sufficiently matches that of the comparable emitter-detector pair. This match can also be limited to specific wavelength ranges that are relevant for the analysis.

The exact same distance must not be observed for an equal distance characteristic. It is important that the volume of the sample through which the photons arriving at the detector have passed is sufficiently similar between the pairs. The directional characteristic also has an influence on this. The emitter and detector distance essentially determine how deep the light that is measured in the means penetrates into the sample. The directional characteristic also has an influence on this. Pairs that are sorted into a group of comparable or equal pairs can have a sufficiently similar emitter-detector distance and sufficiently similar directional characteristic with respect to the emitter-detector pairing, or the differences in directional characteristic and distance can compensate each other such that a sufficient comparability arises as a result.

In some cases it is advantages to additionally require a comparable orientation for membership in a group of equal pairs.

Depending on the sample, analyte and measurement arrangement, one or multiple or combinations of the aforementioned conditions in combination with each other or with other conditions are advantageous.

The term sample in connection with this document should be generally understood as an object to be examined. This should, in particular, not preclude the sample involving a living being or human. In particular, both living and non-living or no longer living objects to be examined are meant by this term. Samples can have different states. In particular, solid, liquid and gaseous samples are possible. Examples for a sample would be: the ball of the thumb of a person, including the skin layer, a blood, urine or tissue sample. A piece of fruit, a piece of plastic, a pellet of powder (tablet), an exhaust gas sample or a pureed quantity of vegetable are also examples for a sample.

The concentration of an analyte in connection with this document should be understood as a property of the sample to be examined. An especially typical property can be characterised by the concentration of a substance in the sample. Examples of such substances include flavonoids, cytochrome C oxidase, glucose, HbA1c, fructose, advanced glycation end products (AGE), haemoglobin, carboxyhaemoglobin, methaemoglobin, synovitis, lactate, cholesterol. The analytes that are not recognised directly, but indirectly in relationships with other substances are also meant in the scope of the document. This includes, for instance, recognition with cleavage products, waste products, marker substances, in the creation or breakdown of involved products. This also applies to information that can be determined from combinations e.g. of different substances. In addition, the definition also comprises properties that go beyond the purely chemical concentration, such as microcirculation of the vessel, skin moisture, water content of skin/tissue, blood alcohol, drugs, tenderness of flesh, resistance of plants to frost, degree of ripeness of plants, NO2, pulse, oxygen saturation and heart frequency. Concentrations of an analyte are therefore also to be understood as concentrations of substances in a part of the sample, in particular. For instance, the sample can be the living hand of a living person. The interesting part of the sample in this example is the blood of the person. The interesting concentration is the alcohol in the blood. A local limitation is also meant. An example would be the concentration, e.g. moisture of specific substances in specific skin layers, such as the epidermis or a depth of 0-0.5 mm. In particular, concentration distribution features are also meant, which, for instance, can be gradients or graduations or oriented or non-oriented or isotropic or anisotropic. This also applies to the progression of concentrations over time that can be, for instance uniformly, periodically rising or falling. Therefore, the concentration of an analyte should also be understood as variables derived from one or multiple properties described above. An example of a period concentration progression and a variable derived thereof is the determination of the heart frequency that can be determined from the periodicity of the concentration distribution of specific blood substances in a body part, as well as the approximate value for the general condition of the health of the analysed person that can be deduced from this and other variables.

Emitters in the scope of this document should be understood, in particular, as elements that emit the light or electromagnetic radiation. This includes, in particular, ultraviolet radiation, infrared radiation, x-radiation and microwaves as well as radio waves and the frequency ranges in between.

Examples include, in particular, incandescent lamps, glow lamps, light emitting semiconductors, light emitting diodes (LEDs), light emitting conductors, lasers, laser diodes, fluorescent tubes, OLEDs, RGB LEDs, tubes, antennae, luminescent substances, flames, electric arc, sparks and additional sources of radiation known to a person skilled in the art.

Detectors should be understood, in particular, as elements that detect the radiation emitted by the emitters and can convert the radiation into a signal.

Examples include, in particular, phototransistors, photodiodes, photomultipliers, spectrometers, photoresistors, solar cells, tubes, camera chips, CCD cameras, semiconductors, LEDs, antennae, light field sensors, pyrometers and radiation sensors.

Transparent material should be understood, in particular, as materials through which at least part, preferably the majority, of the radiation emitted by the emitters can pass through.

Examples are clear plastic or glass, milky or cloudy plastic or glass, coloured plastic or glass, transparent materials, gas, and plastic through which radio waves can pass.

Non-transparent material should be understood, in particular, as materials which prevent, at least in part, the radiation generated by the emitters from passing through. This can, for instance, take place by means of absorption, reflection, interruption or dispersion.

Examples include plastic or glass with black or coloured pigments, metal, ceramic, wood, conductive plastic, e.g. with radio waves.

Elements with volume percentages or surfaces that can be transparent or non-transparent are also considered as a whole as transparent or non-transparent material. Examples are a glass element that has been covered by a non-transparent metal layer or lacquer layer or a metal element that has been provided with holes in order to allow light to pass through.

The definitions of transparent and non-transparent material can overlap. In such cases, the material that is rather permeable for the radiation for the considered wavelength characteristic applies as the transparent material and the material that is rather impermeable applies as the non-transparent. In particular, the classification of a material can depend on the wavelength of the radiation. Transitions between transparent and non-transparent material do not need to be severe. For the purpose of simplification, the facts are preferably explained for severe transitions without limitation on generality. However, the transparency of a material can be influenced, for instance, with incorporation of pigments or chemical or physical reactions in some locations. Examples are the development of photographic film, the incorporation of pigments on parts of an otherwise homogeneous plastic layer or the incorporation of light-dispersing bubbles in a homogeneous transparent member by a laser.

Figure 1:
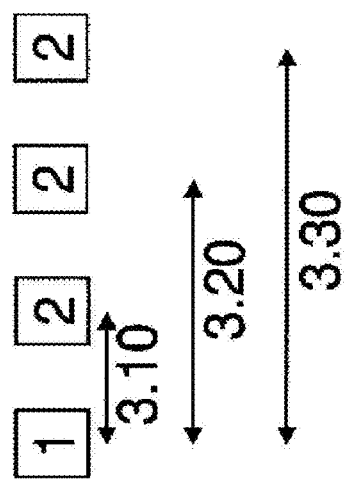
FIG. 1 shows a simple emitter-detector arrangement.

FIG. 1 Simple Emitter-Detector Arrangement

FIG. 1 shows a simple emitter-detector arrangement in which emitter 1 and multiple optical detectors 2 are arranged side-by-side and are arranged in a line.

With this arrangement, the light back-scattered from the sample is detected in three different locations. In the process, the distance to the emitter increases. Optical paths 3.10 to 3.30 differ considerably. 3.10 identifies a short optical path, 3.20 identifies a medium-length optical path and 3.30 identifies a long optical path.

In order to be able to detect the inhomogeneity of a biological sample, such as the skin, multiple measurements are necessary in different skin locations with this arrangement. This simple emitter-detector arrangement necessitates additional measuring processes that must be performed in succession and the measurement result can also be influenced by physiological changes between the measurements.

If the emitter-detector arrangement is arranged repeatedly in a device side-by-side as a solution to the problem, the effort is increased by the same factor that the number of measurement points is increased. It is a further disadvantage that the measurement points in the direction of their longest dimension cannot be positioned very closely to each other.

FIG. 2 Emitter-Detector Arrangement in the Form of a Matrix

The disadvantages of the arrangement shown in FIG. 1 are solved according to the invention with a two-dimensional emitter-detector arrangement. FIG. 2 shows an example of such an arrangement.

A larger number of different optical path lengths arises in an advantageous manner. Therefore, 3.10 shows a short optical path, 3.15 shows a short to medium-length optical path, 3.21 shows an additional medium-length optical path and 3.30 shows a long optical path. In the arrangement in the form of a matrix, it is possible to achieve the number of measuring paths necessary with a smaller number of Emitters 1 and optical Detectors 2 than a duplication of the arrangement from FIG. 1 would have produced.

Figures 3, 4:
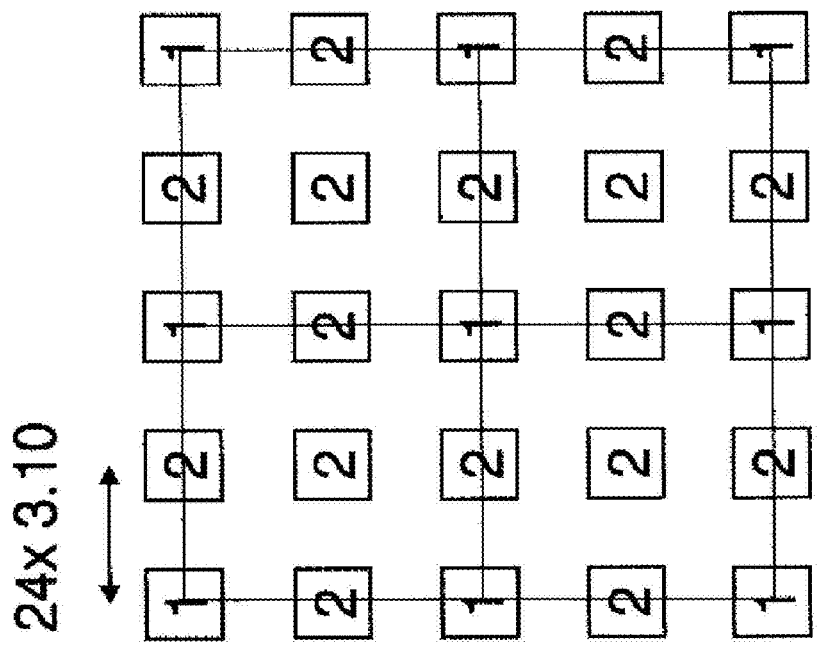
FIG. 3 shows an emitter-detector arrangement in the form of a matrix-representation of 24 short optical paths.
FIG. 4 shows an emitter-detector arrangement in the form of a matrix-representation of 16 short to medium-length optical paths.
Figure 6:
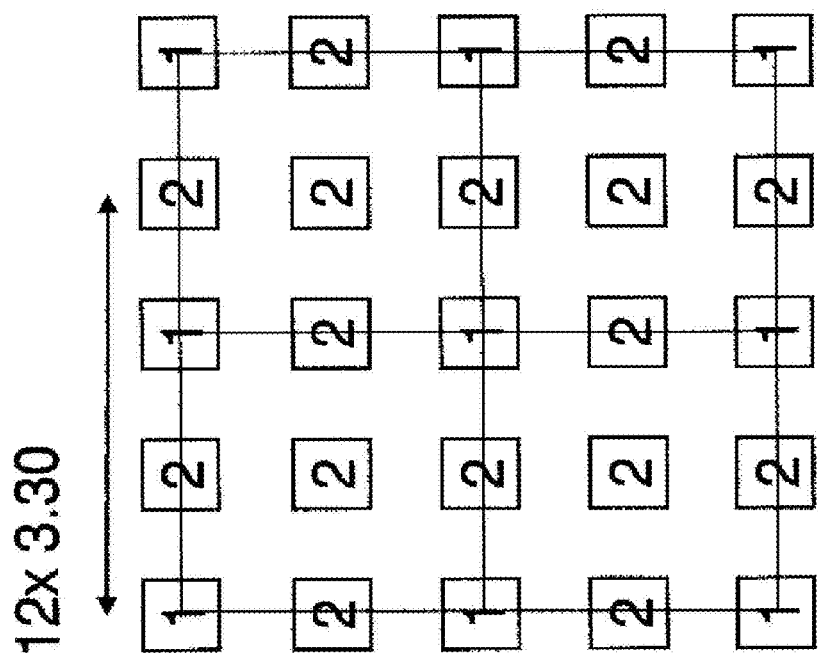
FIG. 6 shows an emitter-detector arrangement in the form of a matrix-representation of 12 long optical paths.
Figure 5:
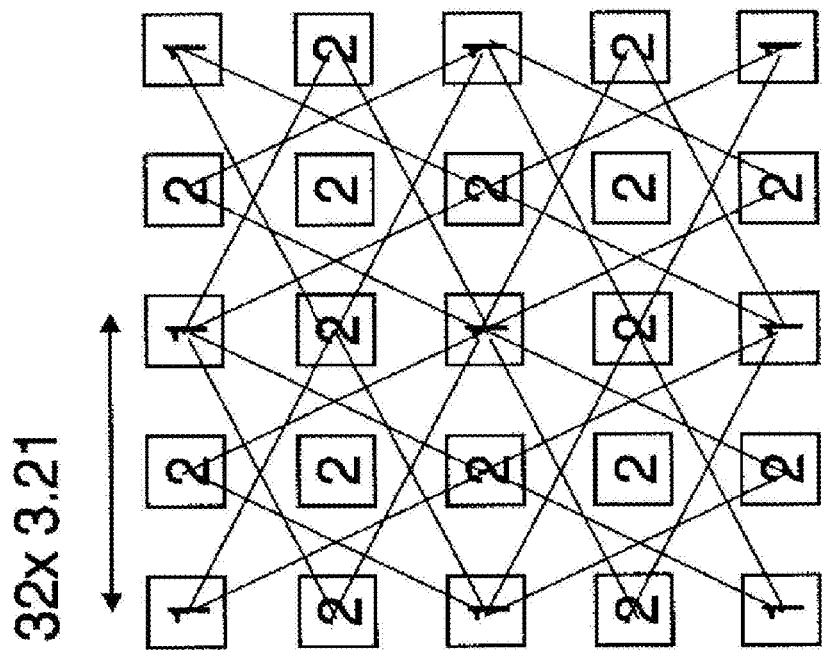
FIG. 5 shows an emitter-detector arrangement in the form of a matrix-representation of 32 different medium-length optical paths.

FIG. 3 Emitter-Detector Arrangement in the Form of a Matrix—Representation of 24 Short Optical Paths FIG. 4 Emitter-Detector Arrangement in the Form of a Matrix—Representation of 16 Short to Medium-Length Optical Paths FIG. 5 Emitter-detector arrangement in the form of a matrix—representation of 32 Different Medium-Length Optical Paths FIG. 6 Emitter-detector arrangement in the form of a matrix—representation of 12 Long Optical Paths FIGS. 3 to 6 show how the number of optical paths from Emitter 1 to optical Detector 2 multiply heavily in the example arrangement while the number of Emitters 1 and optical Detectors 2 required for this purpose increase less drastically. The various optical path lengths (3.10, 3.15, 3.21 and 3.30) are shown in FIGS. 3 to 6 together with their frequency of occurrence. The sum of at least the 84 optical paths shown in the figures is produced with only 9 emitters and 14 optical detectors.

FIG. 3 shows the number of short optical paths 3.10 that is provided 24 times with this arrangement. FIG. 4 shows the 16 short to medium-length optical paths 3.15. FIG. 5 shows the 32 other medium-length optical paths 3.21 and FIG. 6 shows the 12 long optical paths 3.30.

FIG. 7 Example Cross-Section of a Device Housing

FIG. 7 shows an example housing for a device for the measurement of analytes on the ball of the thumb of the hand. This can be preferably used for measurement of carotenoids. Housing 12 is shown conventionalised in a cross-section. To conduct the measurement, it is applied directly on the ball of the thumb (see FIG. 8). The housing has a curvature 7 with respect to the shape of the ball of the thumb.

Curvature 7 and bulge 8 contribute in an advantageous way to prevent scratching of the optoelectronics 4 if the measuring device is, for instance, placed on a table and moved back and forth between measurements. Curvature 7 and a surrounding or punctual bulge 8 simultaneously contribute to a shielding of the optoelectronics from external light during the measurement.

The optoelectronics 4 are preferably located in the centre of curvature 7. Depending on the implementation, there can be a lateral offset between housing 12 and optoelectronics 4. The optoelectronics are connected to printed circuit board 6, which can help to receive and process signals.

A casting compound 5 is integrated between housing 12 and optoelectronics 4 as a seal to prevent the penetration of moisture and dust. Preference is given to a housing design for a handheld measuring device that is chamfered over handle 11 and can be held during the measurement.

In an advantageous variant of the device, the start of the measurement is triggered by pressing activation button 10. Activation button 10 is advantageously arranged recessed in activation recess 9 such that undesired switching-on is prevented.

As FIG. 7 shows, the activation button is preferably arranged such it can suggest the position of the optoelectronics. A relatively precise application of the measuring device on the ball of the thumb of the hand is thus made easy as a result. In an advantageous variant, the optoelectronics are also used to check whether contact has been established with the test subject. A measurement is only triggered if this contact has been established.

In an advantageous variant, activation button 10 only reacts once a certain pressure has been applied. As a result, it can be ensured that the measurement is not started until the device is sufficiently pressed on the test subject.

FIG. 8 Housing with Positioning Aids for Measurement on the Ball of the Thumb of the Hand FIG. 8 shows an example of a device having housing 12 that is applied with handle 11 on the ball of the thumb 14 for the measurement. The measurement is started by pressing activation button 10. The device has positioning aids that support the repeat accuracy for application of the optoelectronics 4 on the ball of the thumb 14 of the hand 13. The lateral guide 15 ensures the reproducibility of the measurement position in one direction and guide 16 ensures the reproducibility in the other direction. In an advantageous variant of the invention the guides are adjustable such that they can be adapted to the user or the object to be measured.

In another advantageous variant, the stops are arranged such that they are well-suited for different measurement object sizes without adjustment.

In another variant the guides are exchangeable or can be attached on the housing of the device.

In an advantageous variant, tailored guide elements can also be used for the specific user. For instance, with an impression of a hand can be made in a curable plastic composition.

FIG. 9 Housing with Positioning Aids for Targeted Movement of the Device on the Surface of the Measurement Object The positioning aids 15 and 16 of the example housing 12 described in FIG. 9 can also be used to purposefully move the optoelectronics 4 over the surface of the ball of the thumb 14 of the hand 13 in order to detect the inhomogeneity of the measurement object as precisely as possible. In an advantageous variant of the invention, it enables reproducible movement along a track 18. In the process, either continuous measurement values can be taken after pressing activation button 10 or measurement values can be detected at specific points of the measuring track 18. For this purpose, for instance, the depth guide element 16 can slide continuously or incrementally along, for instance, a sliding path 17. The measuring track and sliding path can represent a straight line or a curve in the three-dimensional space.

In an advantageous variant it is also possible to use multiple measuring tracks. This can be achieved, for instance, with by adjusting additional guide elements.

The data recorded during the movement of the optoelectronics 4 can be offset with a rule such that a representative value of the inhomogeneity of the measurement object is determined.

FIG. 10 Example Configuration of the Device

FIG. 10 shows an example configuration of the inventive configuration of the device. The optoelectronic components can be arranged on a carrier material or a printed circuit board 101. Emitters 102 and optical emitter chips 104, as well as the optical detectors 103 are distributed on the carrier material 101 according to the inventive configuration. Detector chips are not shown in the simplified representation. Similarly, not all emitter chips are identified. Moreover, only some optical emitters and detectors are explicitly identified as such with numbers. The components that are not identified are also emitters or detectors. For measurement of additional parameters, the arrangement has a temperature sensor 160 and a moisture sensor 161 such that the measuring conditions are detected very well and can be taken into consideration in determining the concentration of the analyte. The light barrier 107 consists of a material that is impermeable to light and is shown in the form of an exploded drawing at a distance from the device for better clarity. In the version of the device that is ready for operation, the light barrier 107 is arranged on a printed circuit board 101. The size and shape of the individual cavities have been selected in consideration of the component volume and the orientation of the emitters and detectors, such that desired radiation and detection characteristics are achieved and the light is preferably propagated to appropriate optical paths. If the light barrier, which is not shown in this example, is produced as a separate component, it can be retrofitted on the arrangement of the optoelectronics and the cavities are cast with a material that is permeable to light. The transparent material is not represented in the drawing. Partially there are cavities that have emitters or detectors have one wavelength characteristic. Partially there are cavities that have emitters or detectors having more than one wavelength characteristic, such as RGB emitters or RGB detectors or multiple single emitters and/or detectors.

FIG. 10a shows an example arrangement of emitters and detectors that can be selected for the mechanical arrangement from FIG. 10.

Emitters are identified with the letters a to y. Emitters having the same letters have the same wavelength characteristic.

Emitters h, g and i are not separated by non-transparent material.

Emitters x and y are example emitters that can have multiple wavelength characteristics. They can emit light varying in wavelength.

Emitters y radiate light having a different directional characteristic that emitters x.

The detectors are identified with the Greek letters α, β and γ.

Detector α has, for example, five different wavelength characteristics.

Detectors β and γ have different wavelength characteristics. With the rectangular geometry, the directional characteristic is not rotationally symmetrical.

Figure 10B:
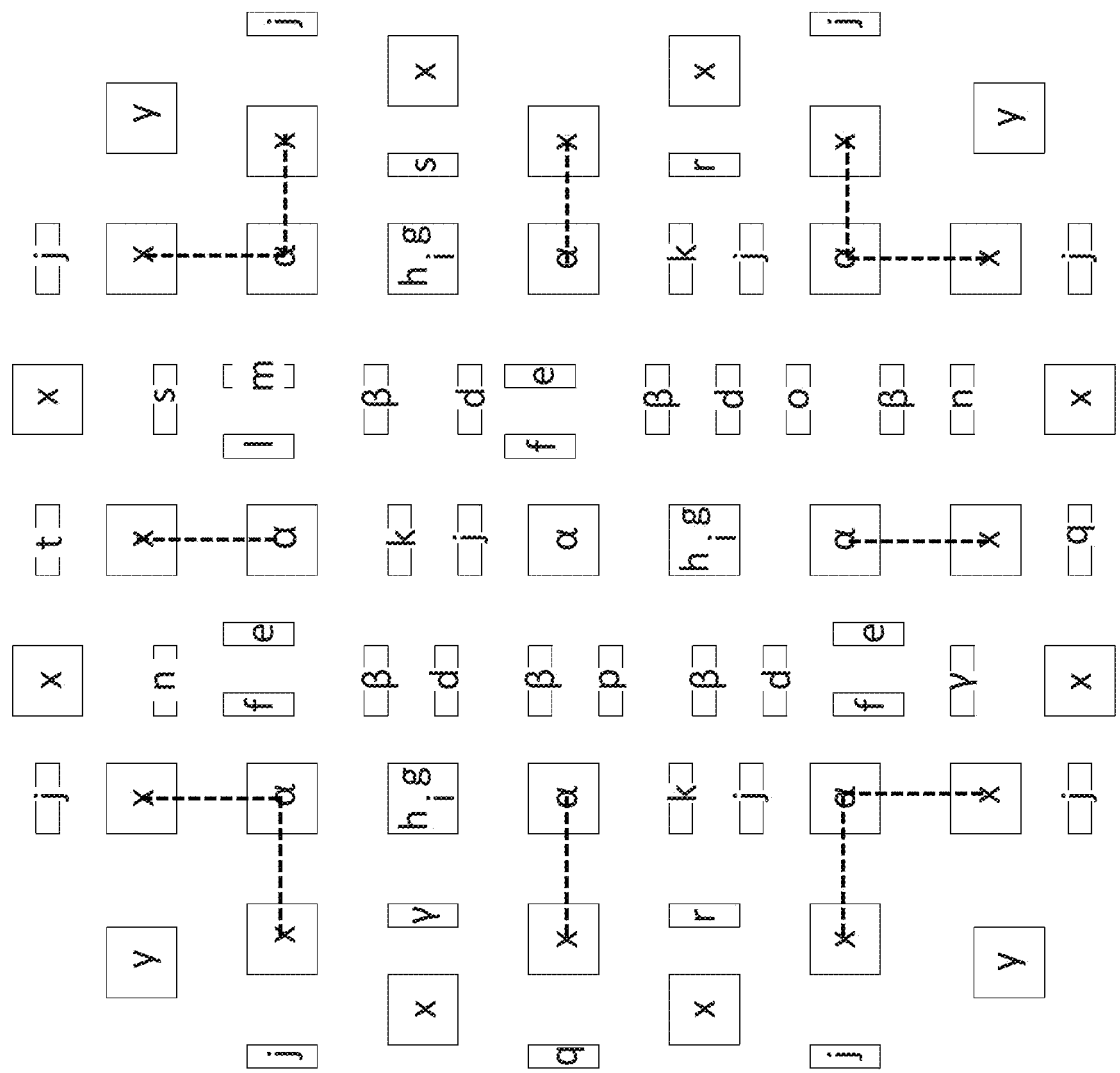
FIG. 10b shows an example of equal emitter-detector pairs.

FIG. 10b shows an example group of equal emitter-detector pairs. In this example, an approximately equal wavelength, approximately equal optical paths and comparable directional characteristics were selected as a feature for group membership. Four different orientations of the connecting line from the emitter to the detector are recognisable, such that one optical path is realised in each 90 degree angle range.

Figure 10C:
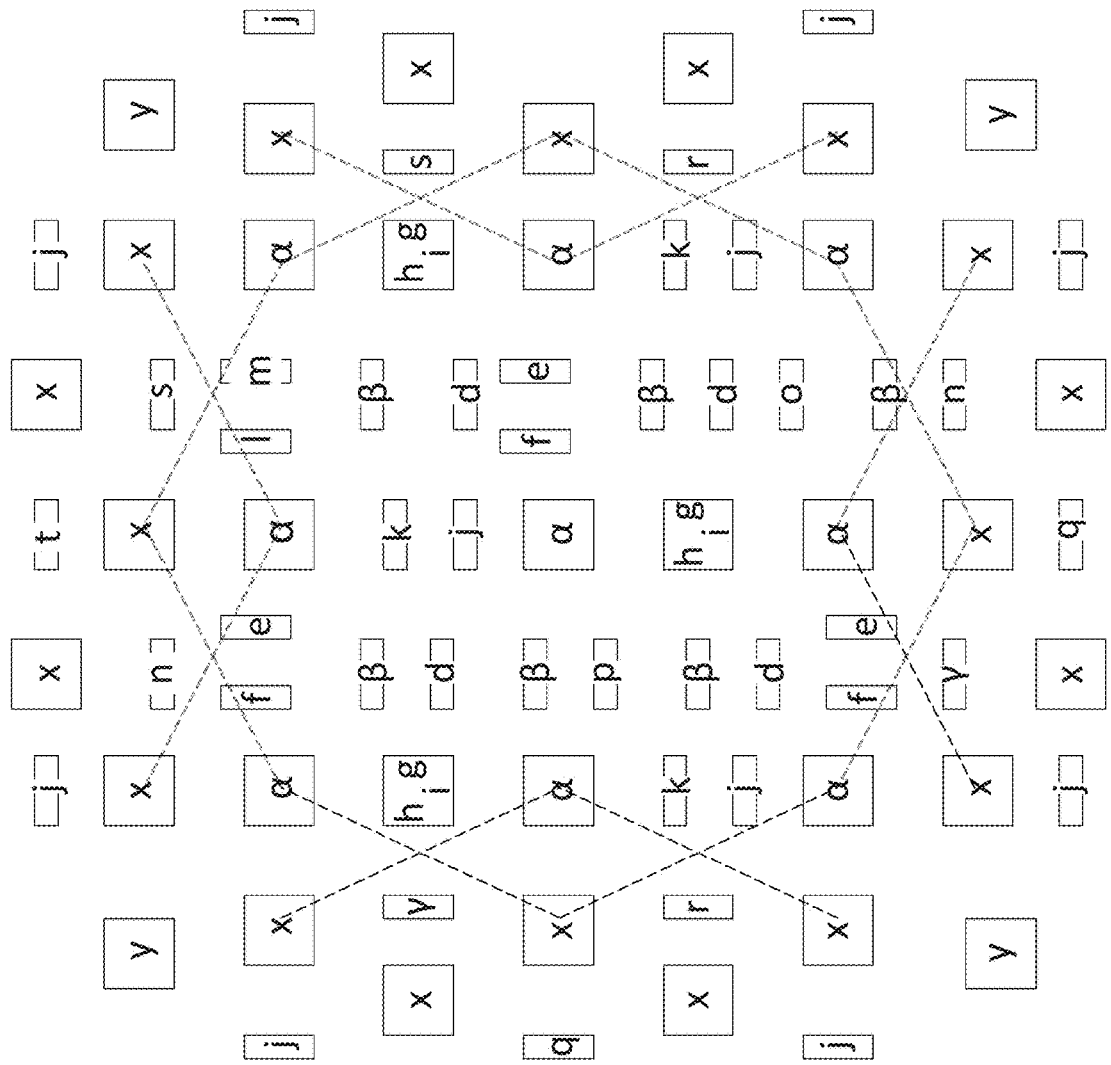
FIG. 10c shows an example of equal emitter-detector pairs.

FIG. 10c shows an example group of equal emitter-detector pairs. In this example, an approximately equal wavelength, approximately equal optical paths and comparable directional characteristics were selected as a feature for group membership. Eight different orientations of the connecting line from the emitter to the detector are recognisable. It is recognisable that a finer gradation of orientations take place in comparison with FIG. 10b.

Figure 10D:
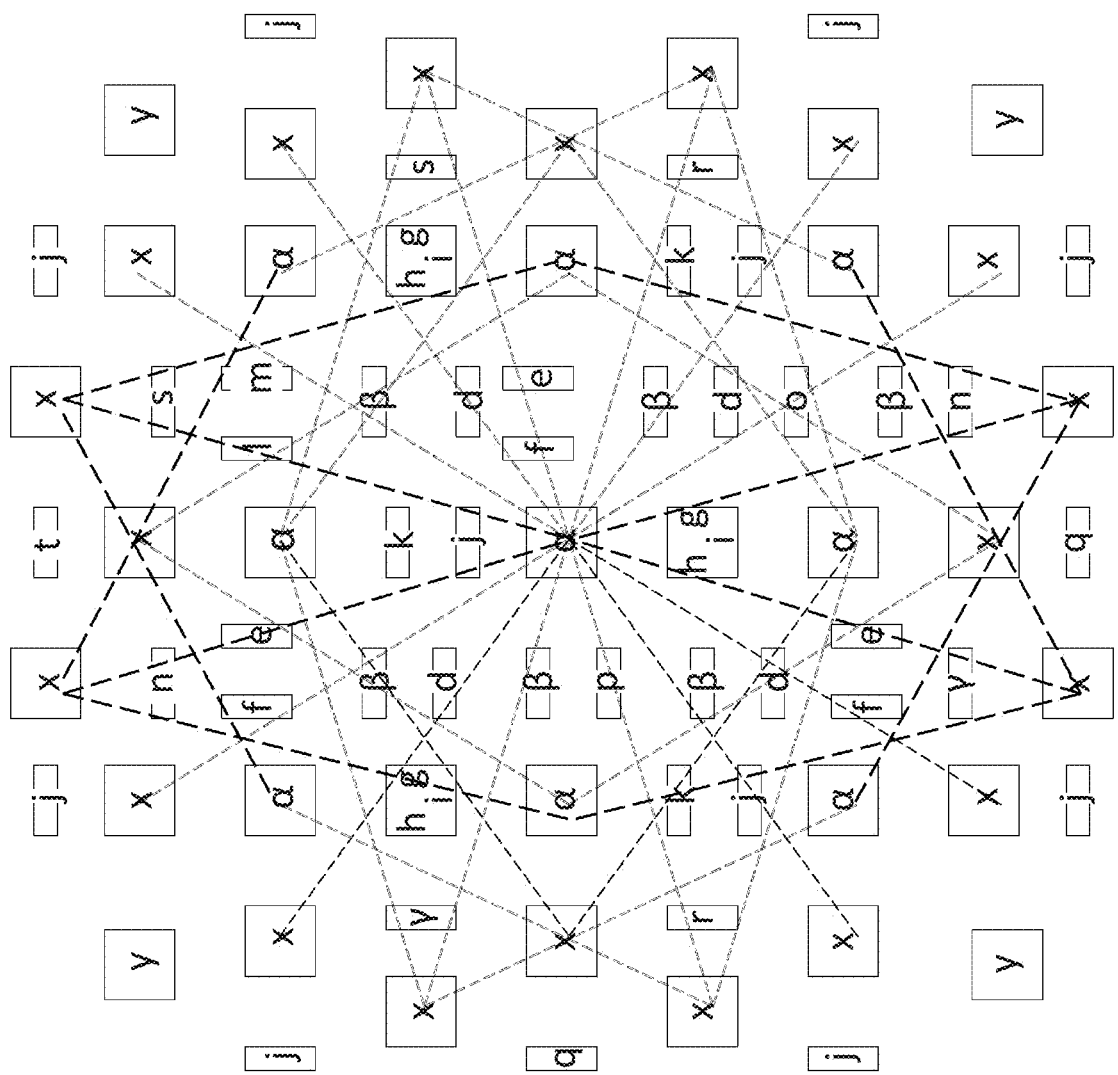
FIG. 10d shows an example of equal emitter-detector pairs.

FIG. 10d shows an example group of equal emitter-detector pairs. In this example, an approximately equal wavelength and approximately equal optical paths were selected as a feature for group membership. Forty optical paths from the emitter to the detector are recognisable. It is recognisable that, in consideration of the orientation, the arrangement was selected such that little overlap could be achieved. The 16 emitter-detector pairings with the middle detector analyse an annular area around the central point of the device, wherein the orientation of the measurement is oriented towards this centre in each case. The remaining 24 pairings that are shown also cover this annular area, but have an orientation that essentially runs transversely to the 16 initially mentioned pairs. The multiple use of emitters and detectors is also easily recognisable in this example. A sharp increase in the number of possible emitter-detector pairing is achieved specifically with the use of longer distances, which are made possible with an evaluation circuit having higher dynamics. The connecting lines of emitter-detector pairs are shown with different broken lines in FIG. 10d. This should provide an example that groups of equal emitter-detector pairs can also be divided into sub-groups. In general, the measurements of an emitter-detector pair can, of course, also be included in more than one group.

Figure 10E:
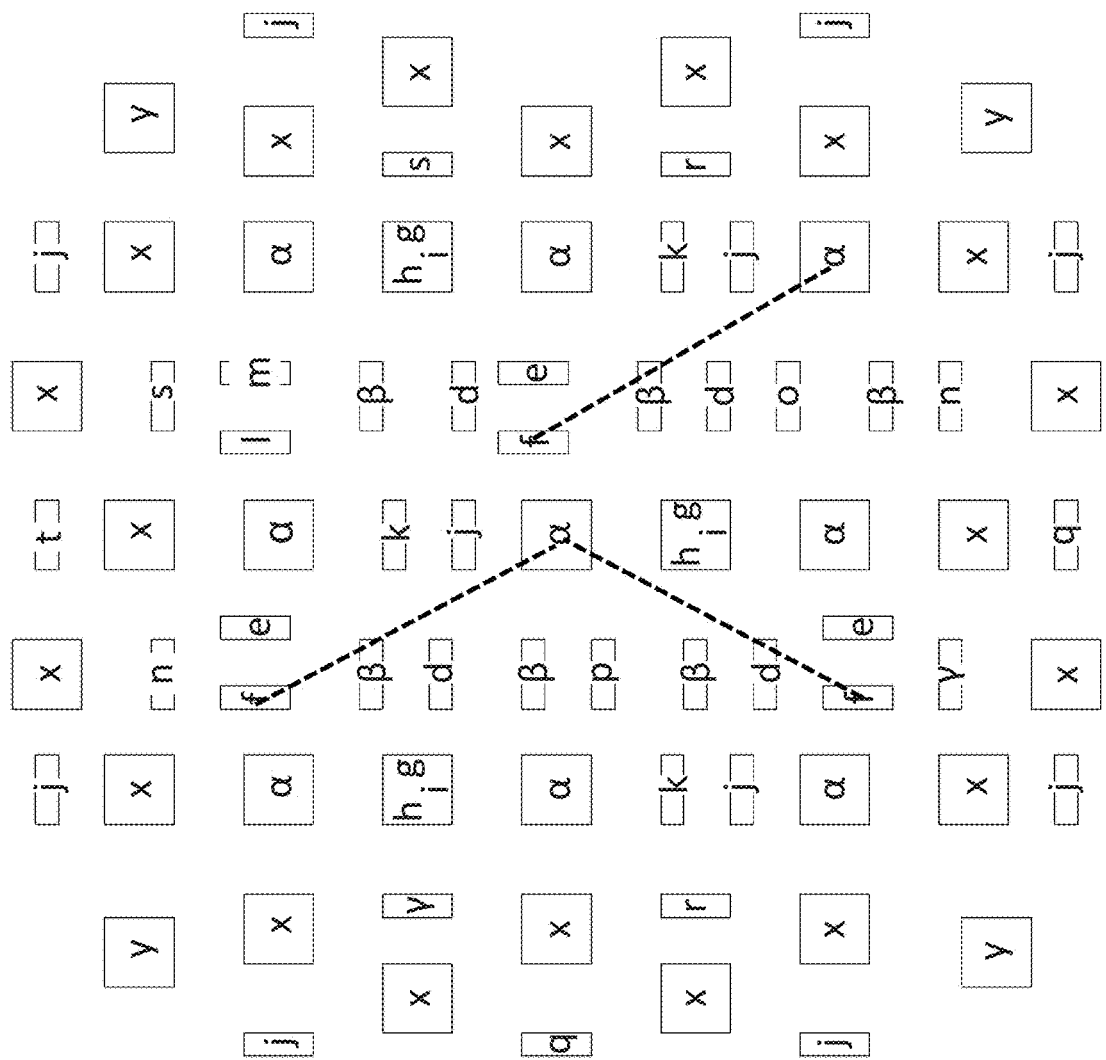
FIG. 10e shows an example of equal emitter-detector pairs.

FIG. 10e shows an example group of equal emitter-detector pairs. In this example, an approximately equal wavelength, approximately equal optical paths and comparable directional characteristics were selected as a feature for group membership. Three different orientations of the connecting line from the emitter to the detector are recognisable. Three different measurement locations are recognisable. This is an example demonstrating that the arrangements do not have to be symmetrical.

Figure 10F:
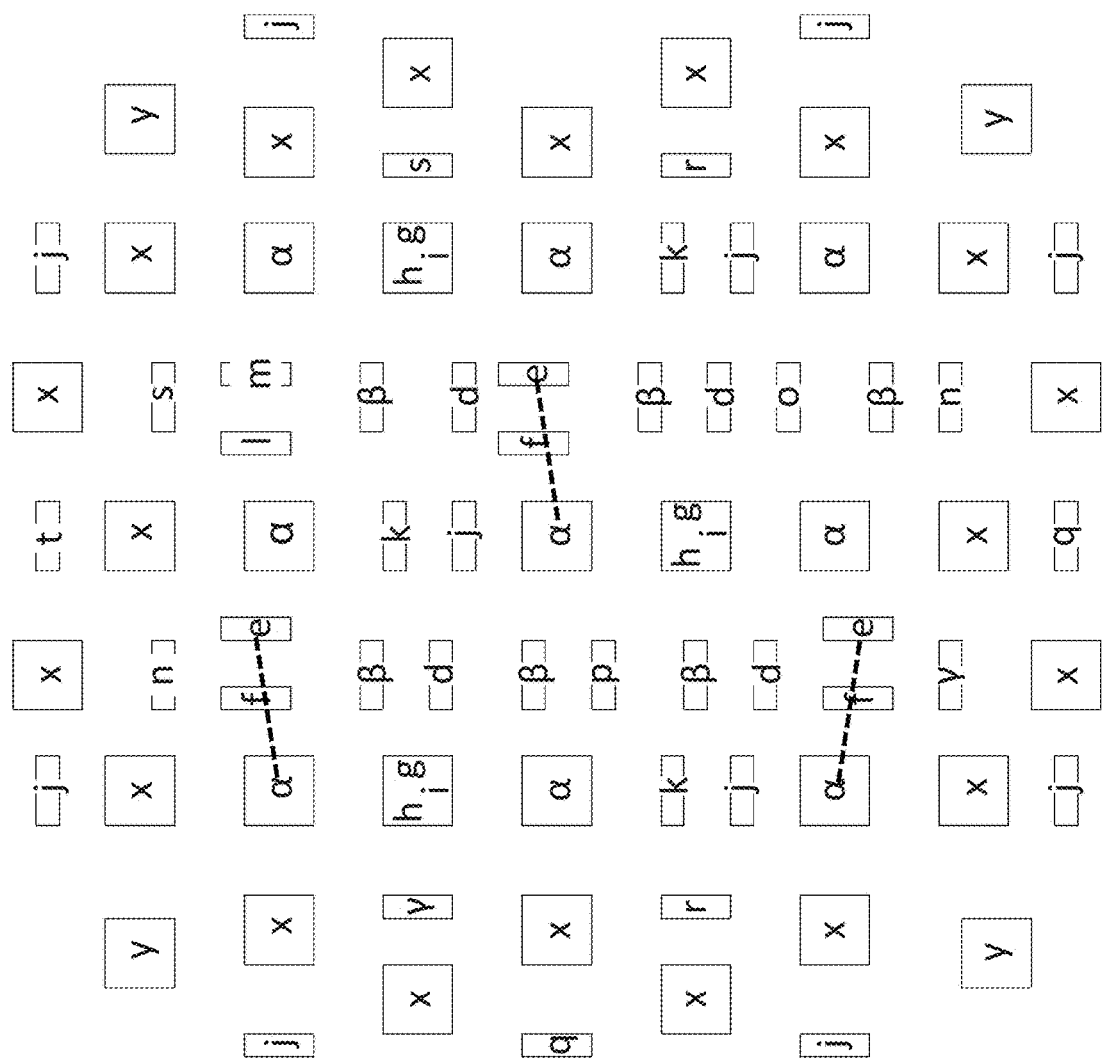
FIG. 10f shows an example of equal emitter-detector pairs.

FIG. 10f shows an example group of equal emitter-detector pairs. In this example, an approximately equal wavelength, approximately equal optical paths and comparable orientation were selected as a feature for group membership.

Figure 11:
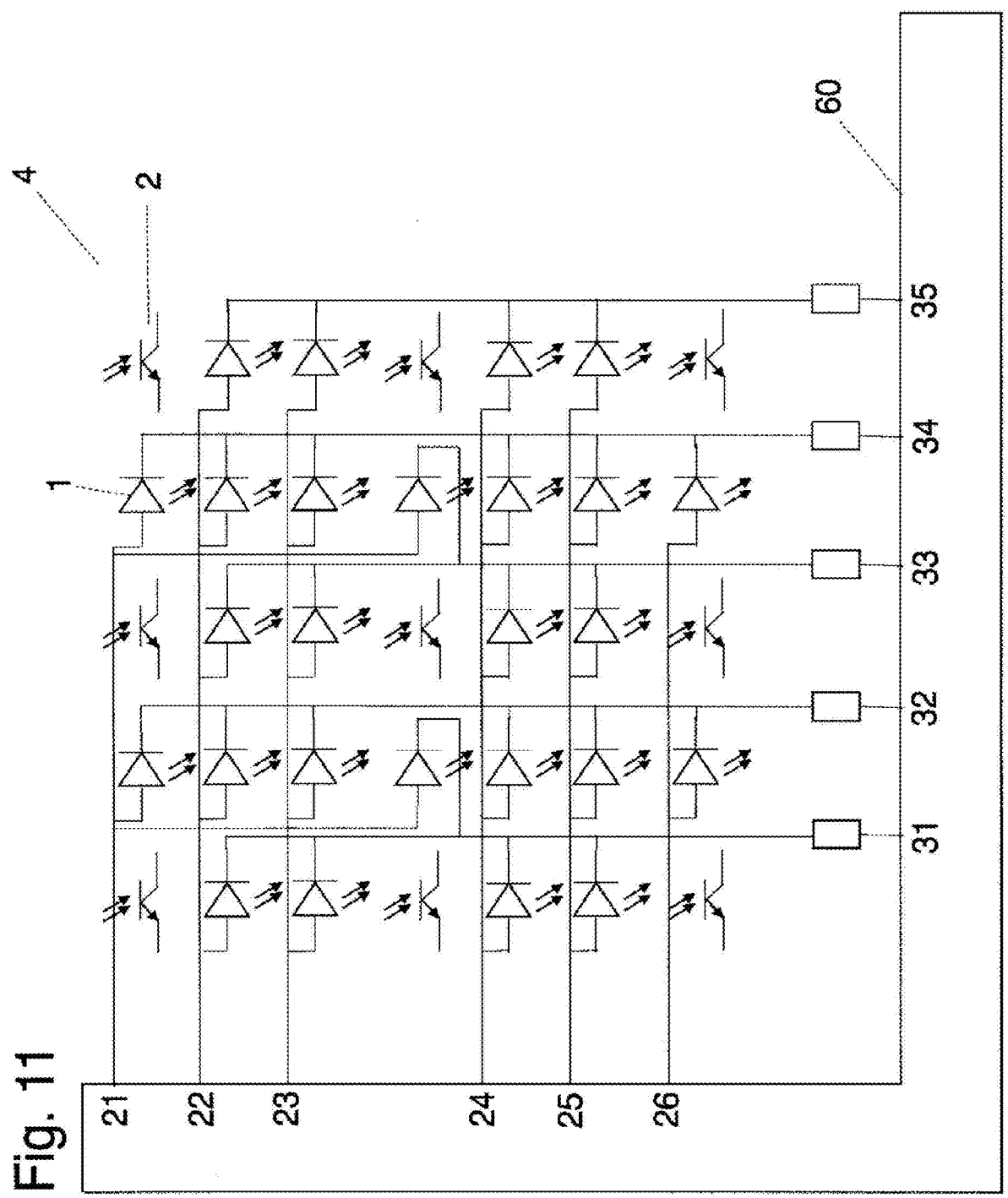
FIG. 11 shows a description of electronic components—optical emitters.

FIG. 11 Description of Electronic Components—Optical Emitters

For the evaluation of the measurement conducted with optoelectronic device 4, the emitter side of which is shown in this figure, it is advantageous to activate the various optical emitters 1 in succession in order to be able to detect the measurement data of the various optical paths. In particular, if only one light source is simultaneously activated, a matrix arrangement such as the arrangement shown in FIG. 11 offers unexpected advantages in the control. It is known from matrix arrangements that fewer control lines from control electronics 60 are required.

In the case of the described arrangement of optoelectronics, however, there is an unexpected advantage with the wiring, because the arrangement in the form of a matrix requires less conductor track space and optical elements 1 and 2 can thus be packed together more densely and provide better measurement results.

The example shown in FIG. 11 is arranged such that 0V are emitted at each of LED line signals 21 to 26 with the exception of one line signal which is on a positive level. The column signals 31 to 35 are all on a positive level, with the exception of one signal which is at 0V.

The light source at the point of intersection of the line signal on a positive level and the column signal at 0V illuminates.

Figure 12:
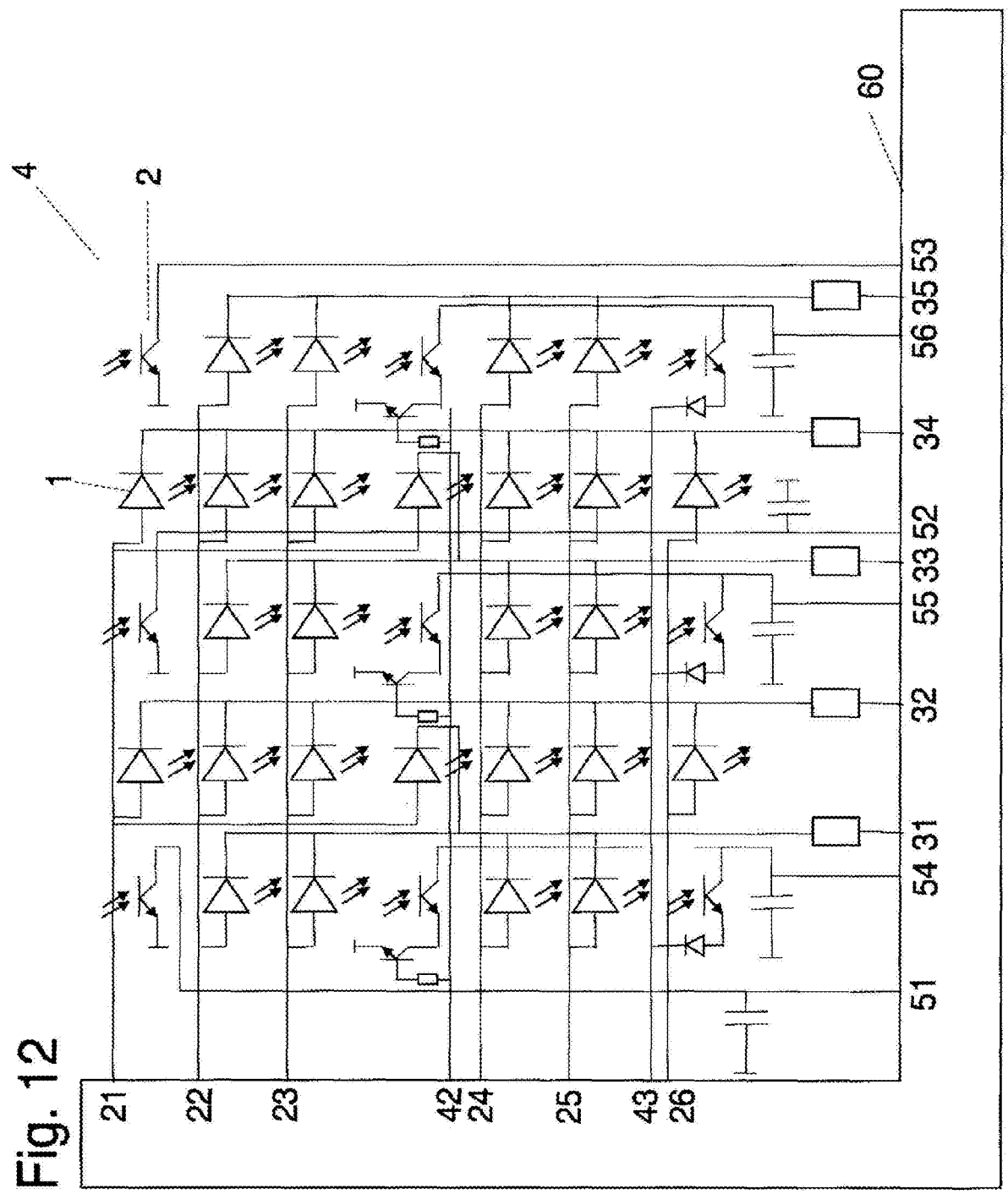
FIG. 12 shows a description of electronic components—optical detector evaluation circuit.

FIG. 12 Description of Electronic Components—Optical Detector Evaluation Circuit FIG. 12 shows an evaluation circuit of optoelectronic device 4 with different circuit variants.

In an advantageous variant, the evaluation of the light-sensitive detectors 2 or other optical emitters 1 used in the system are organised in the form of a matrix. In the process, multiple optical detectors can be connected to a selection line 42 or 43.

In an advantageous variant, the transistors connected to selection line 42 are spatially integrated in the matrix. In an especially advantageous variant, they are arranged on the back side of the printed circuit board (on the side on which there are not optical components).

In an alternative variant, diodes are used instead of transistors, as shown by conductor 43.

The analogue signals of multiple optical detectors can be collected and measured on a common conductor 54, 55 and 56. In an advantageous variant, the measurement can be carried out by measuring the duration of time of the charge- or discharge-process of a capacity.

In an especially advantageous variant, the charge/discharge time is configured for a plurality of half of the mains frequency period. Most light-emitting means generate light in a frequency that corresponds to double the mains frequency. If the measurement with a mains frequency of 50 Hz is a multiple of 10 ms, interfering influences by a flickering mains-operated light are minimised.

In an advantageous variant, the discharge takes place over a time span that is at least approximately balanced with the periodicity of possibly existing artificial light. Therefore, in locations with 50 HZ AC current, for instance, the time span can be a multiple of 10 ms, because both half waves of the mains voltage typically generate a light pulse. The same applies for locations with 60 Hz. With selection of the time span near a suitable multiple of both frequencies, a system that can be used worldwide is provided.

In an especially advantageous variant, the described circuit can be connected directly to a microcontroller. It can carry out the complete function of the control electronics 60 in an especially advantageous variant.

For this purpose, the LED line signals 21 to 26 and LED column signals 31 to 35 are connected to digital IO ports of the controller. The same applies for the detector line signals.

The controller now generates these signals such that exactly one LED is activated and one group of optical detectors is activated.

Then lines 51 to 56 can be connected to, for instance, positive potential via an activatable resistor in the controller. With an AD converter integrated in the controller, a rough value of the current can be determined by the optical detector.

By setting conductors 51 to 56 to positive potential without resistance, the capacitor can be set to a defined potential.

Alternatively or additionally, the potential on the capacitor can be measured with via AD converter or DA converter and comparators.

If conductors 51 to 56 are then switched to high-resistance potential, the change in voltage at the capacitor can be determined by means of an AD converter or comparator or when a threshold of a digital input is crossed. The current through the detector can be concluded with measurement of the time required for this process.

By setting the threshold for the comparator, the time can be adjusted to the beneficial charge times described above. If the charge time is shorter, one or multiple additional measurements can be conducted, wherein the results of the measurements can then be averaged in order to obtain a result that is not significantly influenced by flickering artificial light.

In an advantageous artificial variant, each detector is evaluated individually, which provides the advantage of a quicker measurement. This is shown with detector inputs 51, 52 and 53.

Figure 13:
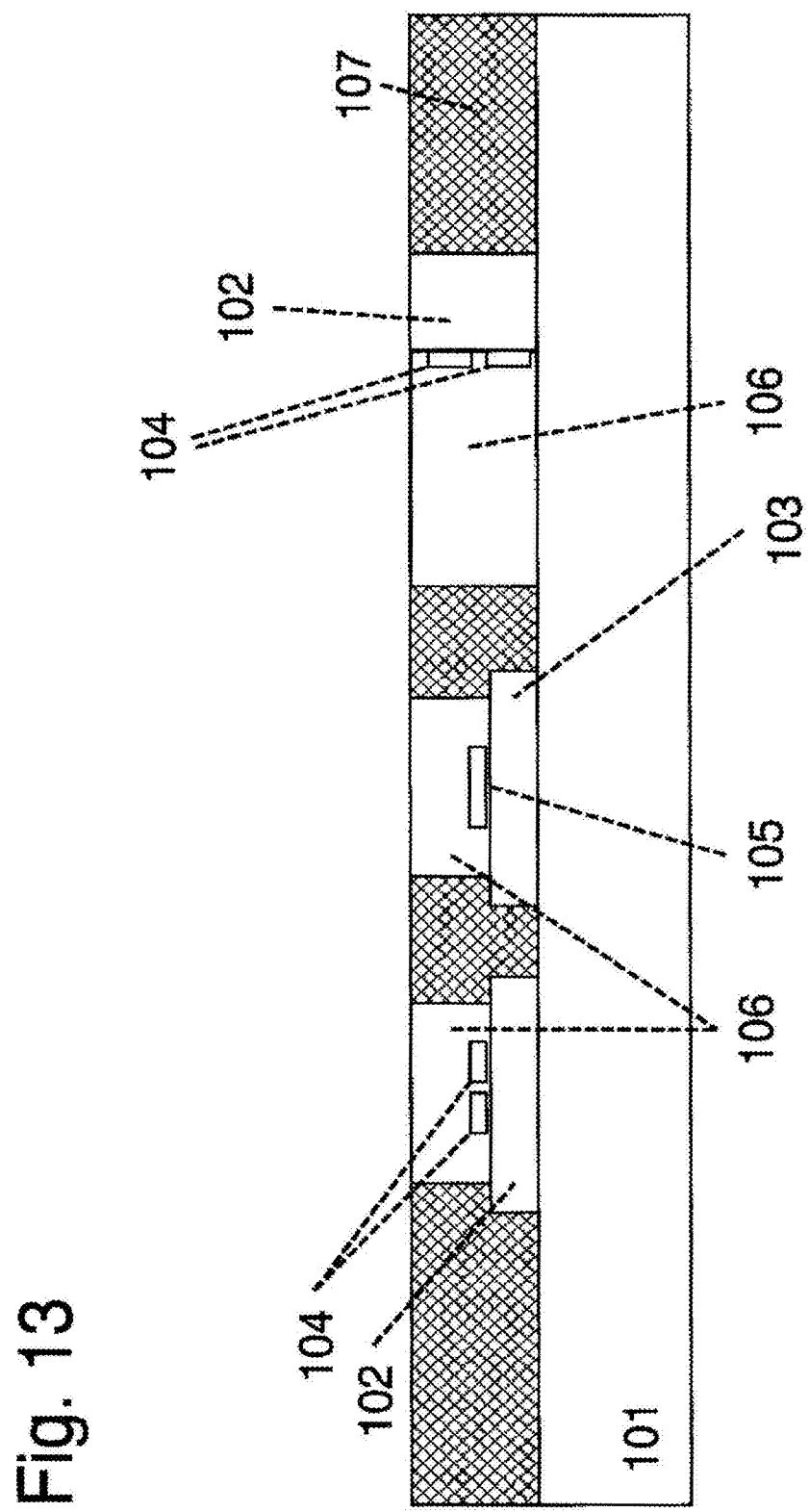
FIG. 13 shows a description of a device 1.

FIG. 13 Description of a Device 1

FIG. 13 shows a part of a cross section of the device.

Optoelectronic components are installed on the carrier material 101, such as FR4 or ceramics, e.g. in the form of soldered SMD components. These components include optical emitters 102 (e.g. LEDs) and optical detectors 103.

The optical emitters 102 have one or multiple chips 104 that emit the light. This light is received by the optical detector chip 105.

Transparent material 106 is used in order for the light to be able to reach the detectors from the emitters. This material may be plastic, for example.

In order to ensure that the light cannot reach the detector directly from the emitter and must pass through the sample to be measured, non-transparent material 107 can be used.

However, it may be advantageous if detectors and emitters are not separated by a non-transparent material. For example, light reflected on the surface of the sample can be analysed in this manner.

In many cases, it is important to influence the paths the light passes through the sample to be analysed. For this purpose, for instance, the orientation of the emitter chips 104 or detector chips 105 can be adjusted. The figure, for example, shows a vertical orientation of the emitter chip 104 to the right.

Figure 14:
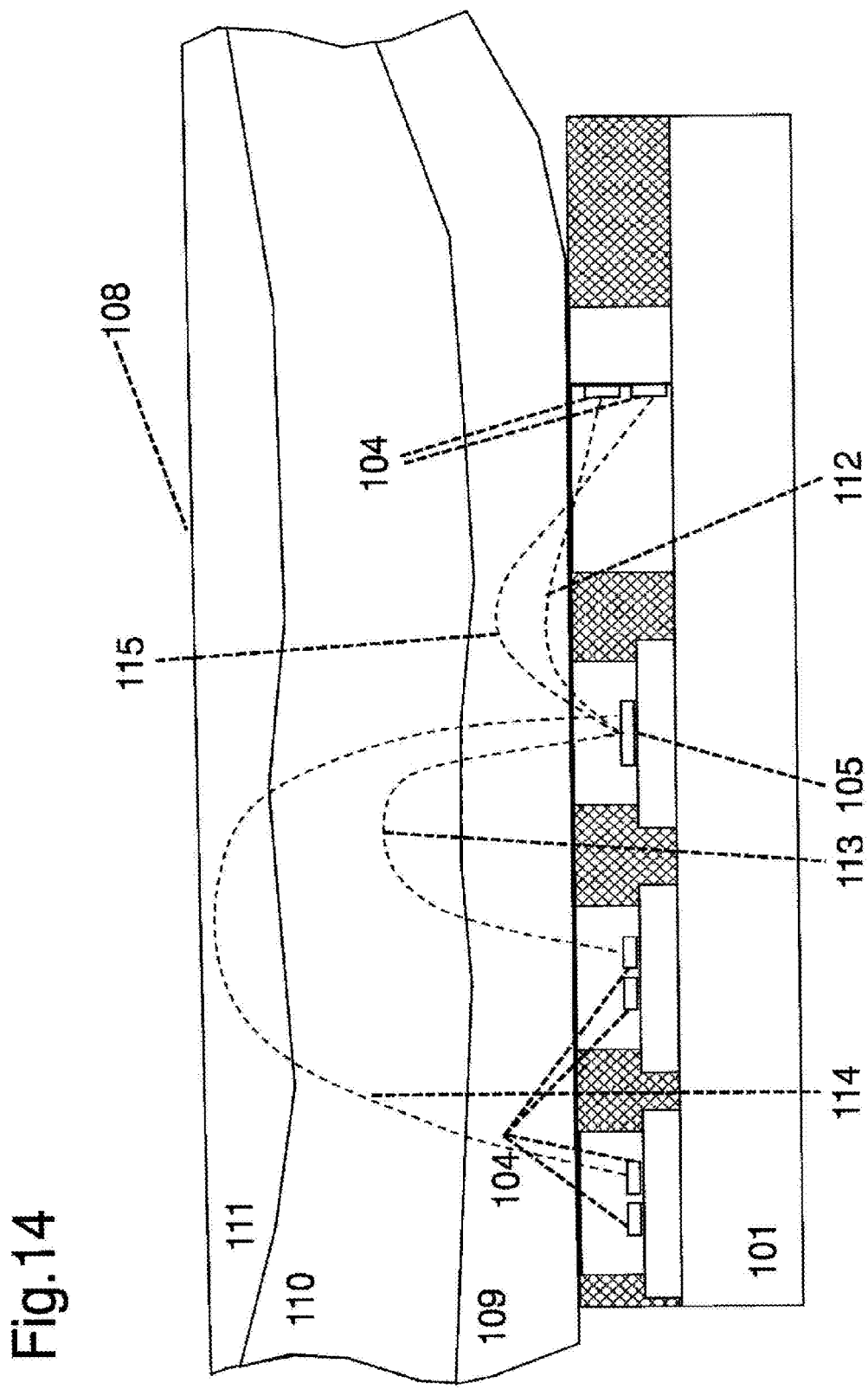
FIG. 14 shows a description of a device 2.

FIG. 14 Description of a Device 2

FIG. 14 shows an example implementation of the device with application of a sample 108 to be measured.

The sample to be measured in this example is a piece of human skin. It has 3 layers. The external layer 109, a middle layer 110 further towards the interior of the body and an even deeper layer 111.

These layers have different properties. With an optical measurement, the concentrations of analytes in the various layers should be measured or estimated.

With the various distances of emitter chips 104 to the detector chip 105, different optical paths arise, as is shown with optical paths 113 and 114.

The optical paths shown in the image each represent only one type of optical path. In reality, the stream of light arriving at the detector is comprised of a plurality of different paths having different lengths and occurring with different probability. The paths are shaped by refraction, diffusion, absorption and reflection of the light in the tissue.

The quantity of light for the relevant optical paths is detected, that reaches the detector from the emitter. The properties of the sample at different depths can be concluded by comparing the measurement results of different optical paths. In this manner, properties of different layers, e.g. different skin layers, can also be concluded.

The measurements can be repeated at the same or different locations in order to increase measurement accuracy.

For calculation of the concentrations of analytes at a specific location in the sample, the measurement results are, for instance, weighted linearly or non-linearly and then added together or linked in a different manner. The result is then weighted linearly or non-linearly. The weighting factors or weighting functions are selected appropriately in order to determine the desired concentration value in the desired sample location.

It may be the case that the distances between detectors and emitters cannot be made short enough in order to generate optical paths from which only a small part leaves the outer-most layer.

In other measurement situations, it is also desirable to influence the optical paths such that a light path that is beneficial for the result is provided. The example of a measurement for the exterior layer 109 should not limit the general case in this here.

The invention shows multiple ways of solving this problem.

In FIG. 14, light radiated from the emitter 104 furthest to the right passes especially flatly through the sample. This is marked as optical path 112. The flat optical path is achieved with the orientation of the emitter chip.

The position of the emitter chip also plays an important role. Optical path 115 shows an alternative position that produces a different optical path.

Of course, the orientation of the detector chip can additionally or alternatively be changed.

Figure 15:
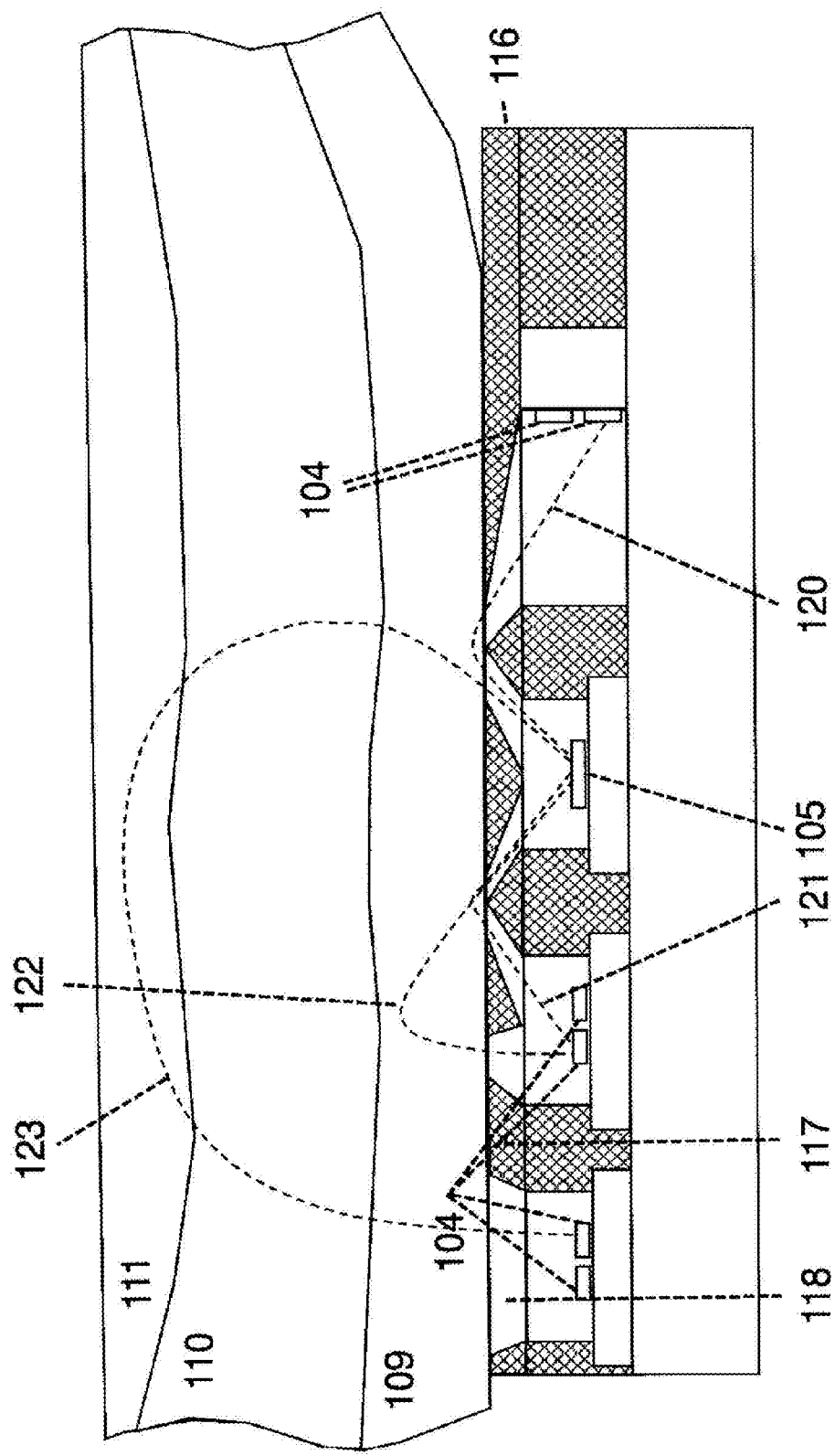
FIG. 15 shows a description of a device 3.

FIG. 15 Description of a Device 3

FIG. 15 shows a different device. With this device elements 116 are used, which can purposefully influence the reception and/or emission characteristic and/or directional characteristic of emitter chip 104 and detector chip 105.

These elements can, for instance, consist of materials that are permeable 118 and impermeable 117 to light. When the materials that are impermeable to light act as a diaphragm, they can influence the directional characteristic.

In addition, the directional characteristic can be influenced when the light is interrupted, reflected or refracted.

The surface of the element for optimisation of the directional characteristic does not necessarily have to be level. In particular, the directional characteristic can also be influenced by lenses, grids or curved surfaces or mirrors.

Optical paths 121 and 122 show that light can also reach the detector 105 from the emitter 104 along multiple paths.

Optical path 123 shows that especially deep measuring paths can be achieved with purposeful orientation of the light beam away from the optical partner and thus enabling passage through the layers 109, 110, 111 of the sample. An orientation of the light beam vertically into sample also results in deep optical paths.

Optical path 120 shows that especially flat optical paths can be achieved with a suitable orientation of the directional characteristic towards the optical partner and that the light only passes through a smaller part of the layer 109.

Figure 16:
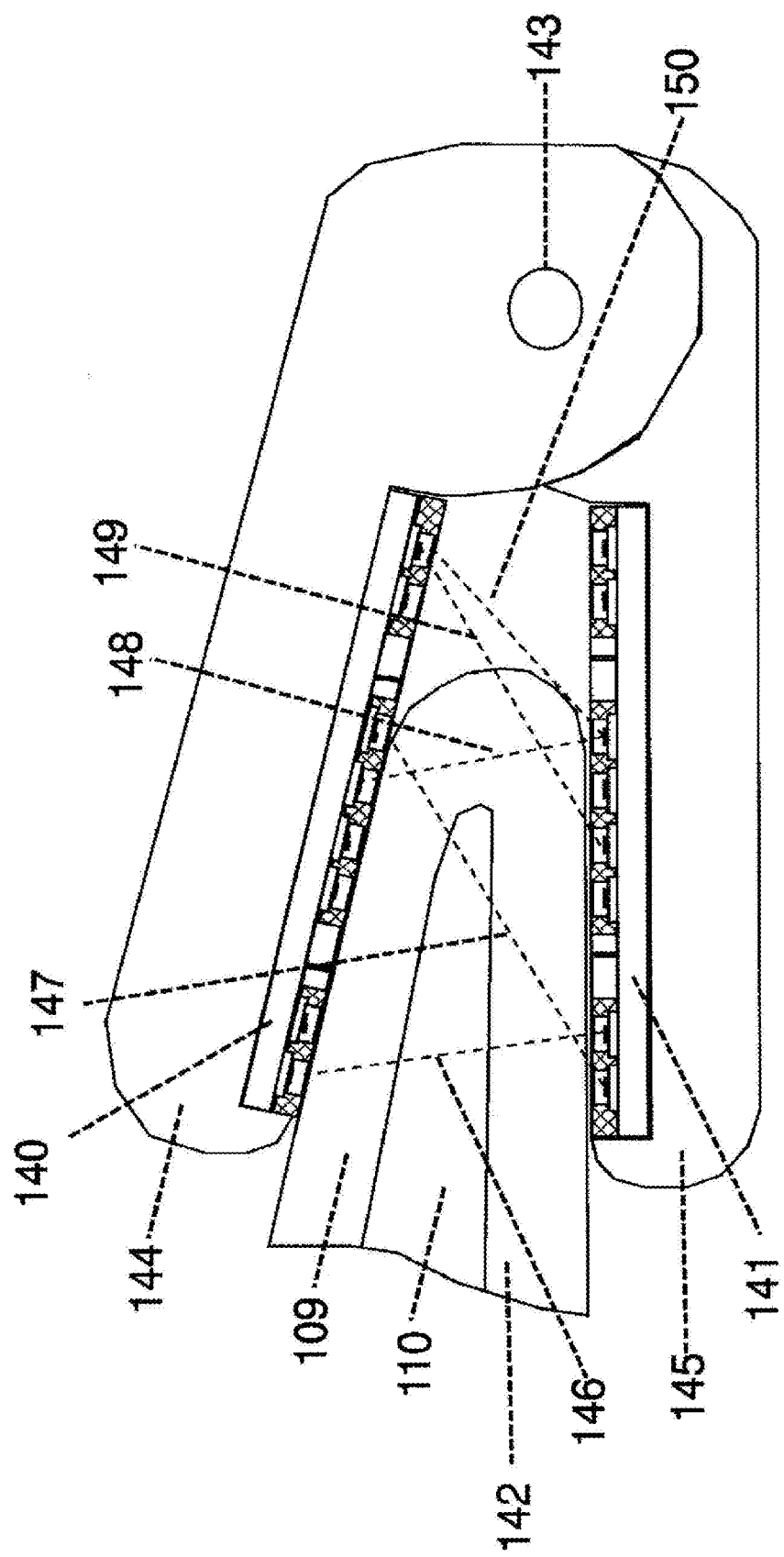
FIG. 16 shows a device with multiple arrays.

FIG. 16 Device with Multiple Arrays

FIG. 16 shows an advantageous variant of the device.

In this variant, multiple emitter-detector arrays are used. Arrays 140 and 141 are shown as an example.

The depicted arrangement is an example. Generally, more than 2 emitter-detectors could also be used. The arrays do not necessarily have to be flat and can also be curved. The array may also be a single curved array.

The arrangement can also be designed as variable, moving or adaptable to the measurement. The example shows a simple linkage 143 with which the two housing parts 144 and 145 have a pivoting connection. However, the movement can also be achieved differently. In particular, the sample to be measured 142 can be clamped or gripped with the movement. The relative position of the housing parts 144 and 145 in relation to each other can be detected by means of sensors, which facilitates the evaluation.

Optical paths that do not pass through the sample, such as 150, can be used to determine how the sample 142 is gripped.

Optical path 146 detects both parts of the tissue of the external layer 109 and significant parts of the middle layer 110.

On the other hand, optical path 148 hardly detects any portions of the middle layer 110. The properties of the middle layer can be determined well with a comparison of the two optical paths.

Optical path 147 shows a diagonal progression through the measurement object. As a result, a longer optical path through the external layers can be achieved.

The straight lines shown in FIG. 16 should not belie the fact that a major portion of the light does not take the direct path, but follows the directional characteristic of emitter and detector and a curve. The directional characteristic in this arrangement can also be appropriately selected.

Optical path 149 shows that optical paths that do not run completely in the sample to be measured can also be used.

Figure 17:
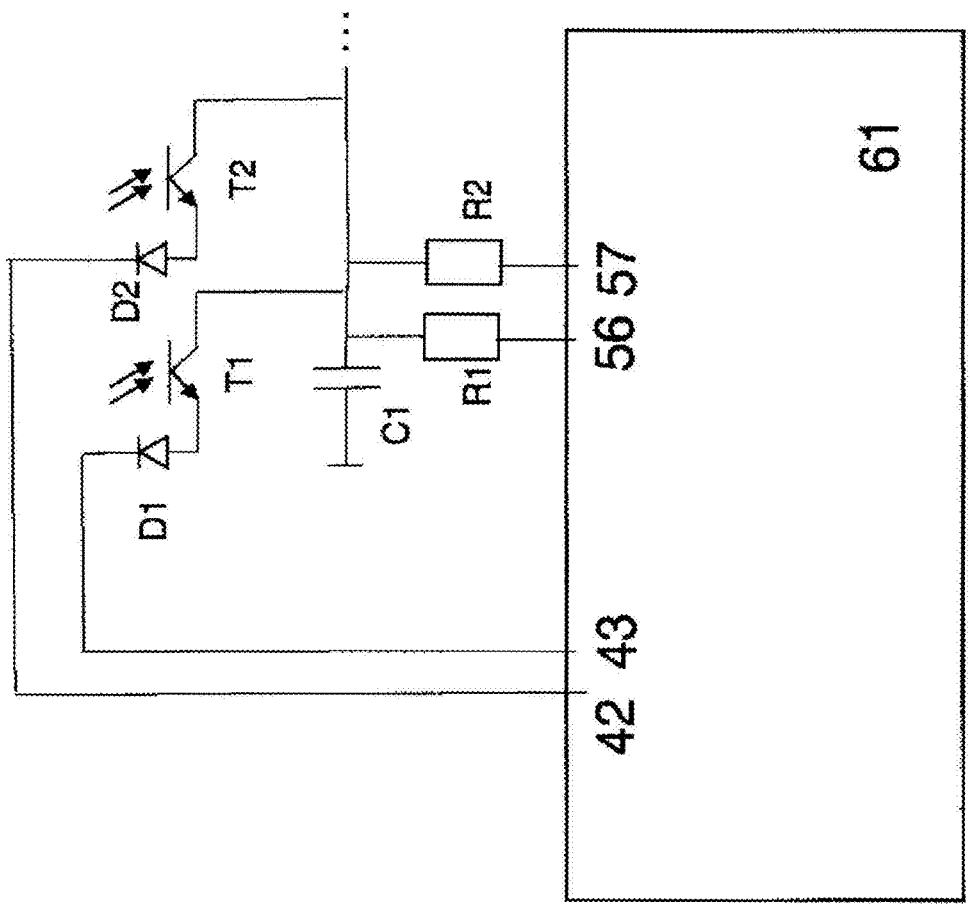
FIG. 17 shows a variant of a measuring circuit.

FIG. 17 Especially Advantageous Variant of a Measuring Circuit

FIG. 17 shows an especially advantageous variant of the measuring circuit.

This can be used for one or multiple phototransistors. For the purpose of simplification, it is only shown here with T1 and T2. The selection takes place again with selection signals 42 and 43. It is assured with these signals that no current flows through the optical detector if it is not selected. Signals 42 and 43 can be switched to high resistance directly by the microcontroller 61 or they can also prevent the current flow using additional components. For instance, this can take place via diodes D1 and D2, which block the current flow with a suitable level at 42, 43. Alternatively, other components can be used instead of the diodes, such as transistors. In addition, with the use of only one detector per measuring input 56, the detector component can also be connected directly to operating voltage such that D1 and D2 are omitted.

C1 is provided in an advantageous variant, which increases the natural capacity of detector and circuit. This capacity is charged and discharged during the measurement.

In principle, the circuit can also be achieved with a reversed current profile. Charging and discharging are then interchanged. For the sake of simplicity, only one variant is described here.

The measuring cycle begins with the charging of C1 via output 56 or 57 via R1 or R2.

In an advantageous variant, charging takes place via 57 and the voltage level is measured at C1 via 56. Especially high brightness can be detected well in this step. This is identified below as Mode D. In the process R2 forms a voltage divider with T1, for example, such that the level of the current flow through T1 can be detected with measurement at 56.

In an advantageous variant, 57 can be omitted, wherein 56 is used simultaneously or vary quickly in succession for the charging and measurement.

In an advantageous variant, R1 or R2 can be omitted.

In an advantageous variant, R1 or R2 can be omitted if Mode D is not used. Alternatively, multiple microcontrollers offer an R1 and/or R2 integrated in the controller.

In an advantageous variant, the current flow is measured repeatedly in cycles during the measuring time in order to calculate the influence of flickering light source (e.g. with mains frequency), which can take place, for instance, by means of averaging.

Mode Z is used in an advantageous variant for high brightness. The capacity is initially charged in this mode. At the beginning of the measuring time, 56 and 57 are switched to high-resistance such that C1 discharges via, e.g. T1. It is determined via 56 whether a specific discharge threshold is reached. If yes, C1 is recharged via 56 or 57. This process is repeated cyclically during the measuring time. The number of cycles and the overall time of the discharge are detected. The current circuit through the detector and thus the brightness can be determined by the number of cycles and the discharge required for this purpose.

With very low brightness, Mode A is used. In the process, the voltage at 56 is measured at the beginning of the measuring time and at the end of the measuring time. In order to increase precision, this can also take place repeatedly. The current flow through the detector element can be concluded based on the voltage difference.

Mode M is established between Mode A and Mode Z. In this mode, multiple discharge cycles are carried out, like in Mode Z. However, the start and end voltage are measured in the same manner as in Mode A. With a suitable computation, the current flow can be determined more precisely.

In an advantageous variant, the voltage is not measured at the beginning of the discharge. It can also be estimated from the boundary conditions of the discharge.

In a preferred variant, the end voltage is monitored by a comparator, which is typically integrated in a microcontroller.

The measurement of discharge times for measurement of current flow is a known method. However, the combination of operating modes explained here provides the advantage that all modes are modified such that they cover the same measuring time and average the measured signal over it. This is very important and advantageous for the device described here for the suppression of errors from flickering artificial light.

There are also special advantages due to the high dynamic range that arises from the combination of measuring methods of Mode D, Mode Z, Mode M and Mode A. The high dynamic range permits detection of both very short optical paths and long optical paths with the same measuring circuit. The circuit can also be applied to multiple detectors without major effort, such that a detector arrangement in the form of a matrix can be realised.

It is also advantageous that no information about the brightness to be expected is required at the beginning of the measurement. By comparison, methods working with the switchover of amplifiers have the disadvantage of having to initially measure in the most insensitive measuring range. Then, if the measured signal was low, a switch to a more sensitive range takes place and measurement takes place again. In the described detector arrangement in the form of a matrix, this would be a major disadvantage, because the measuring time for determining flickering light has fixed length and thus two or more measuring times are required. Therefore, the measurement becomes significantly slower and only a lower number of optical paths can be measured in the total available measuring time. The inventive design does not have this disadvantage. The brightness value to be measured does not need to be known at the beginning of the measurement. Measurements according to Mode D, Mode A, Mode Z and Mode M all occur simultaneously. The correct mode can be selected dynamically from the data accumulated during the measurement without having to restart the measurement.

Figure 17A:
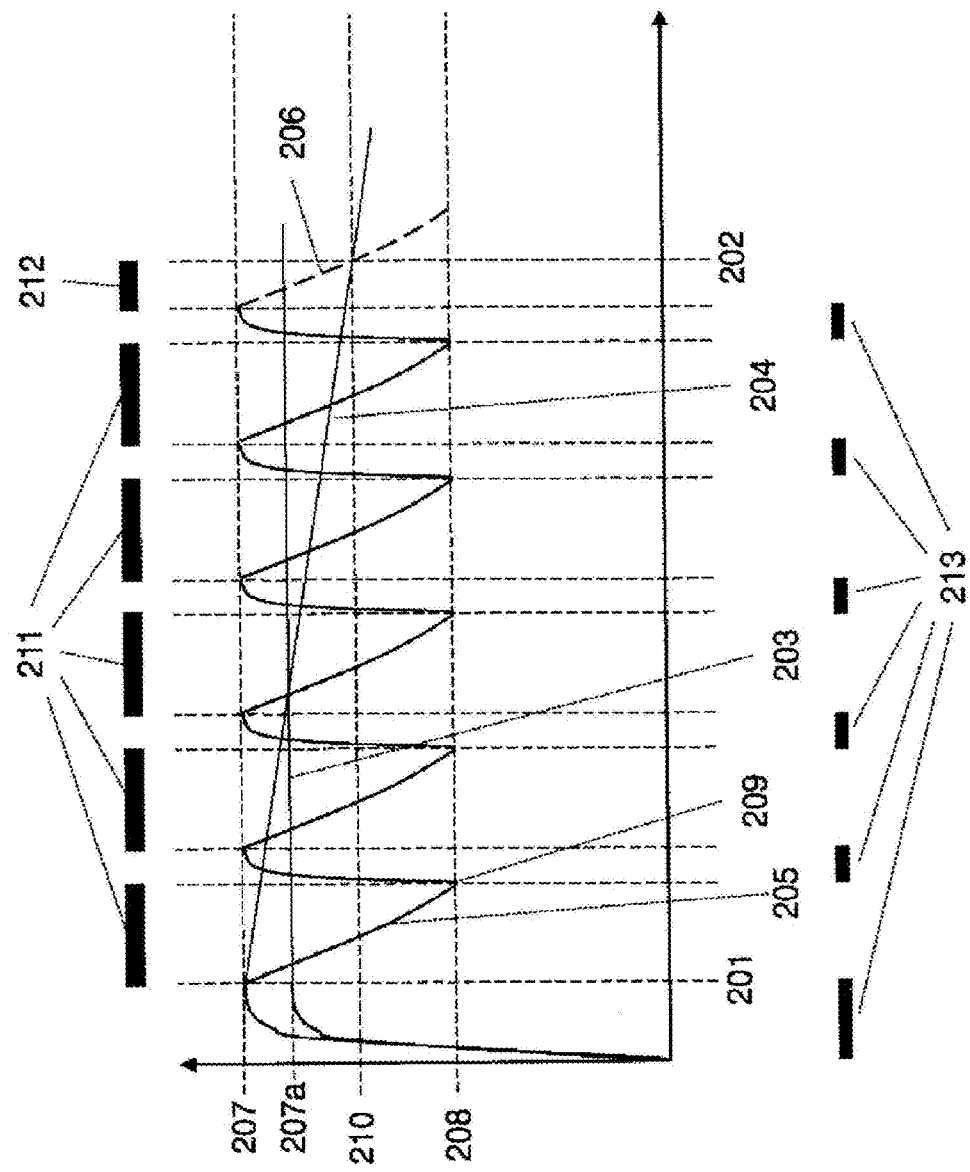
FIG. 17a shows a measurement of one optical path.

FIG. 17a Measurement of an Optical Path

FIG. 17a shows the process of the measurement of a light path. In an advantageous application, a light source is activated and the measurement shown in FIG. 17a is carried out for all detectors that do not share an input 56 (FIG. 17) simultaneously. Then the light source is deactivated and the next light source is activated and measurement takes place again. If all light sources have been measured, the detectors are switched via outputs 42, 43 (FIG. 17) and all light sources are measured again. The sequence can also be different.

Each individual measurement proceeds as shown in FIG. 17a. The capacity C1 is charged in an initial charging step 213. The voltage at 56 is determined with an AD converter (FIG. 17). If this is at a low level 207 a, Mode D is used. The voltage is measured cyclically during the time period of the beginning of measurement 201 to the end of measurement 202 and the results are averaged. Curve 203 shows the voltage progression with consistent brightness. Mode D is suitable for extremely bright situations.

If the voltage is high enough at time point 201, Mode A, Z or M, which are subject to the same process, is used instead of Mode D. The charge voltage 207 is stored. At the end of the measurement, the voltage 210 at 56 (FIG. 17) is measured again and stored.

The difference between these voltages is the discharge voltage for Mode A, which has taken place in the time between 201 and 202. If the threshold value 208 was never undercut during the measurement at 56 (FIG. 17), Mode A is present. The corresponding curve is plotted as 204. Low brightness values at the detector can be concluded directly from this voltage. If necessary, a linearisation is applied. Mode A is suitable for very dark situations.

Curve 205 shows the voltage progression appears in Mode Z and Mode M. The voltage at C1 drops until the undercutting of threshold 208 is determined at 56 (FIG. 17). The time span 211 necessary for this is recorded and charging is initiated, for instance via 56 or 57 (FIG. 17). After the charging is finished, a discharge is carried out again. In the process, the number of cycles is counted, the durations of discharge 211 are measured and the discharge voltage strokes from 207 to 208 are detected for the evaluation.

With a high number of cycles, the brightness at the detector is concluded from the number of cycles alone or, in an advantageous variant, from the number of cycles and the sum of discharge times 211. This is Mode Z. It is suitable for bright situations.

With a low number of cycles, e.g. in the range between 1 and 200 cycles, Mode M is used. In this mode the level of the last cycle is determined with measurement of the voltage 210 at the end of measurement 202 and establishing the difference from 207. The level of the last cycle is added to the sum of the levels of the previous cycles. This value is related to the sum of the discharge times 211 plus the discharge time 212. If necessary, a linearisation takes place before the formation of the sum. By these means, the brightness for medium-bright situations is determined very precisely.

Figure 18:
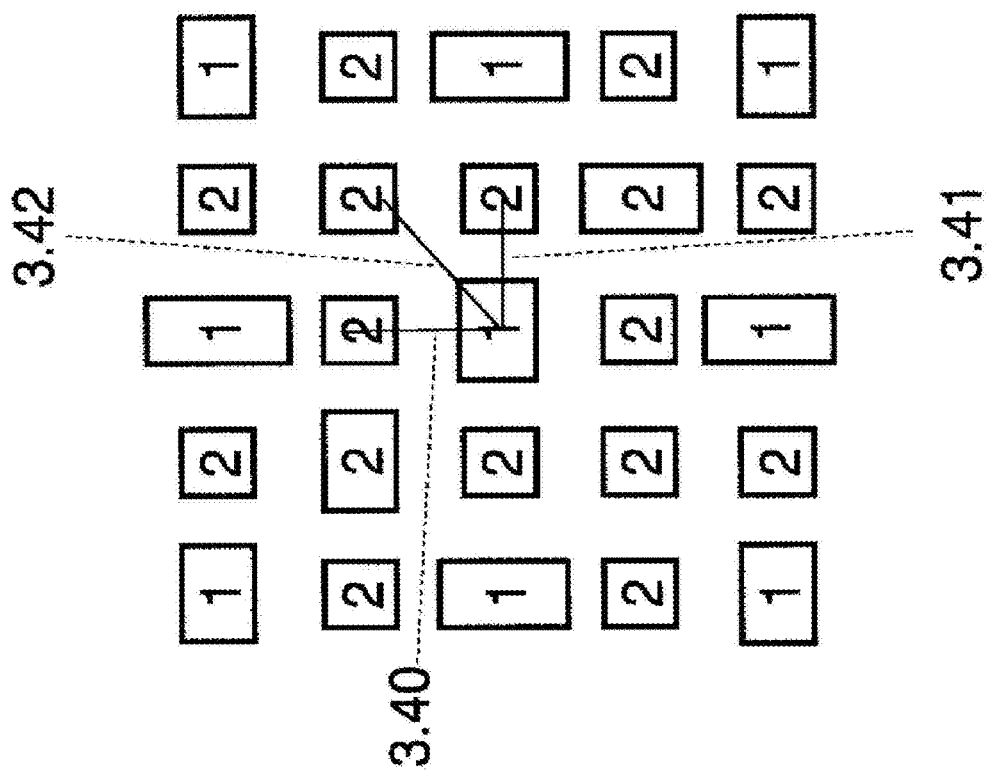
FIG. 18 shows an arrangement with a rectangular arrangement of the light barrier.

FIGS. 18,a,b,c,d,e Directional Characteristic Caused by a Rectangular Arrangement FIG. 18 shows an arrangement with a rectangular arrangement of the light barrier based on the example of optical emitter 1 in the centre of the device. The optical detectors 2 can be reached by the light via different optical paths 3.40, 3.41, 3.42 having a different directional characteristic.

Figure 18C:
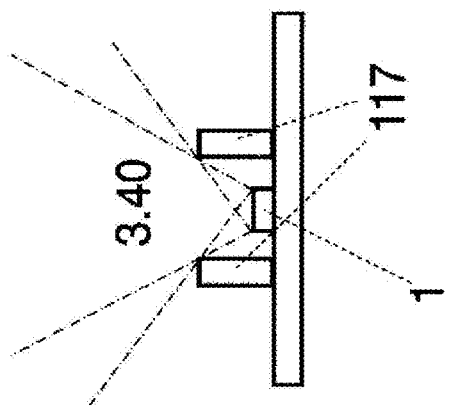
FIG. 18c shows a directional characteristic implemented by using a rectangular shape.
Figure 18B:
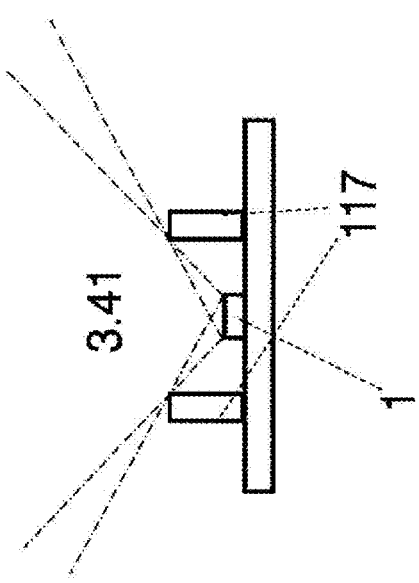
FIG. 18b shows a directional characteristic implemented by using a rectangular shape.

Optical path 3.41 is represented in FIG. 18b in a cross section along the optical path orientation shown in FIG. 18. The broken lines show the delimiting effect of the light barrier 117 on the exiting light and also the partial shade region.

Optical path 3.40 is represented in FIG. 18c in a cross-section along the optical path orientation shown in FIG. 18. The broken lines show the delimiting effect of the light barrier 117 on the exiting light and also the partial shade region.

Figure 18A:
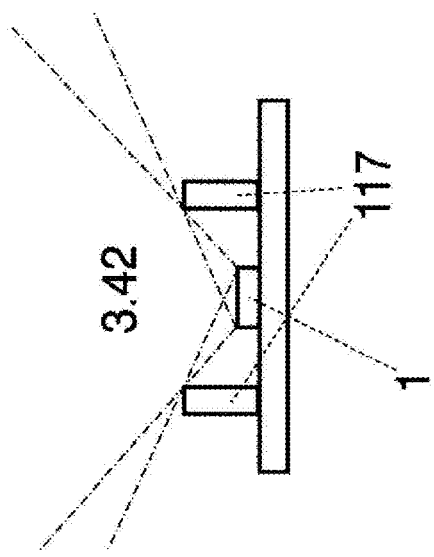
FIG. 18a shows a directional characteristic implemented by using a rectangular shape.

Optical path 3.42 is represented in FIG. 18a in a section along the optical path orientation shown in FIG. 18. The broken lines show the delimiting effect of the light barrier 117 on the exiting light and also the partial shade region.

In a comparison of FIGS. 18b and 18c, it can be seen that the light exit angle in FIG. 18c is lower and the transmission of light 3.40 into the sample is steeper. Therefore, there is a lower percentage of light available, which only passes through the tissue in the flat layers. This is achieved with a narrower arrangement of the side walls of the rectangular shape.

In a comparison of FIGS. 18b and 18a, it can be seen that the light exit angle 3.42 in FIG. 18a is wider than 3.41 and the transmission of light into the sample is booth steep and flat. Therefore, there is a higher percentage of light available, which only passes through the tissue in the flat layers. This is partly achieved with a wider arrangement of the side walls of the rectangular shape. This is also achieved because the section through the emitter chip along the diagonals produces a greater width of the light-emitting surface. The direction-dependent variation in the emission characteristic can also be achieved with an annular shape of the light barrier by using an emitter chip which has corners.

With a comparison of signals having different directional characteristics and with a comparison of signals having different path lengths, the absorption and dispersion share can be calculated in two ways and thus be more precisely determined, and it is also possible to draw conclusions about tissue, which shows deviating absorption and dispersion behaviour in the layers of tissue at different depths.

FIG. 18d shows the analysed volume region of optical path 3.42, which also includes portions of flat light. Line 3.42a, which is drawn through, symbolises a boundary of the space through which a significantly strong flow of photons passes. In fact, the likelihood of the presence of photons slowly decreasing outwards is more probable. The fixed boundary is only provided to illustrate the relationships more easily. The region near the lower arc of 3.42a is especially important in this connection. The photon density is also especially high there. The relevant differences from FIG. 18e are recognisable specifically in this region.

This figure should also demonstrate the fact that the delineated region, with a high probability of presence of photons, is based on the emitted photons, but based on only those photons that are emitted by the emitter and detected by the detector. These photons all take somewhat different paths. They pass through a volume region in the sample which mainly extends above the connecting line between the emitter and detector. However, a lateral deviation from this connecting line will always occur as well. The volume region through which radiation occurs is called an "optical path" and is shown as 3.42a in FIG. 18d and its edge is represented with a line drawn through. Again it shall be noted, that the region ends with a somewhat soft transition and thus has no fixed edge. Somewhat banana-shaped volume regions which have a higher density of photon presence often arise in the shorter path-length range from emitter to detector.

In FIG. 18e a directional characteristic having a narrower emission angle is shown. The lower arc 3.40a does not run as flatly as arc 3.42a from FIG. 18d identified by the broken line. The influence of the flat tissue layers on the measuring signal is less in 3.40a. With the comparison of both signals, the influence of the flat and the deeper layers are separable.

In order to prevent the mathematical methods used to separate the mentioned influences from amplifying measurement errors or noise, the method is combined with the use of multi redundant optical paths. An example of this is shown in a matrix shaped arrangement in FIG. 18.

In an advantageous arrangement, both emitters and optical detectors can achieve the necessary directional characteristic.

Preference is given to a version in which the production-based differences in the emission characteristic of the light source are optimised by filing the emitter cavities with a diffuse material that is permeable to light.

In an advantageous variant, the rectangular shape provides an especially space-saving arrangement that can accommodate an especially large number of light emitters and light detectors on a small surface.

In advantageous variant, the variation of the emission directional characteristic depending on the emission direction is not or is not only achieved with the shape of the light barrier, rather at least partially with the shape and position of the emitter or detector itself. Examples for this include the selection of a rectangular emitter or a non-horizontal arrangement of the emitter surface.

Figure 19A:
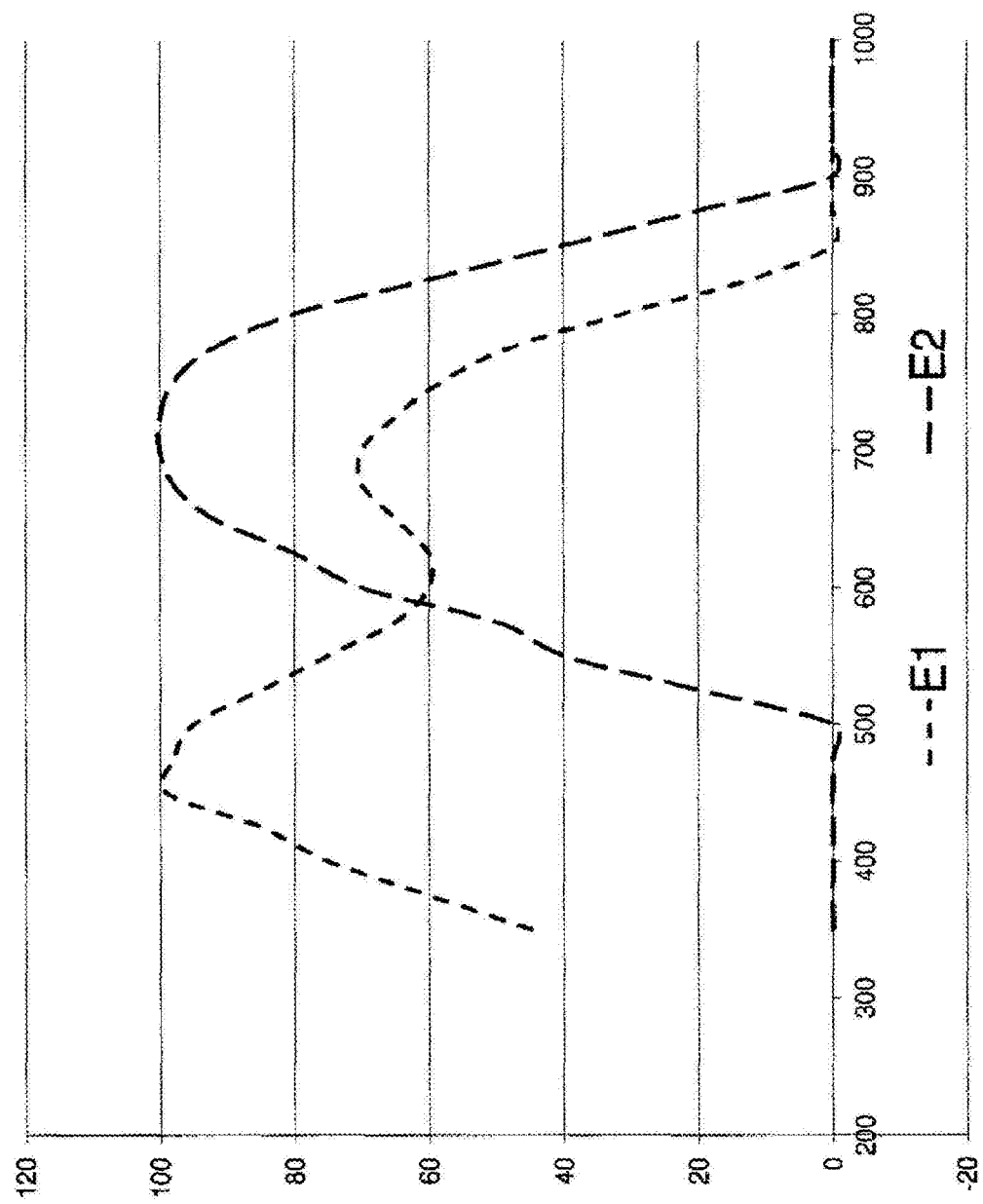
FIG. 19a shows an increase of spectral resolution by using combinations of different optical emitters with different optical detectors.

FIG. 19a,b,c,d Increase of Spectral Resolution with Combination of Different Optical Emitters with Different Optical Detectors In the present invention the spectral resolution of the arrangement is increased by purposefully combining different light emitters with different light detectors. This is shown in FIG. 19a to d.

Figure 19C:
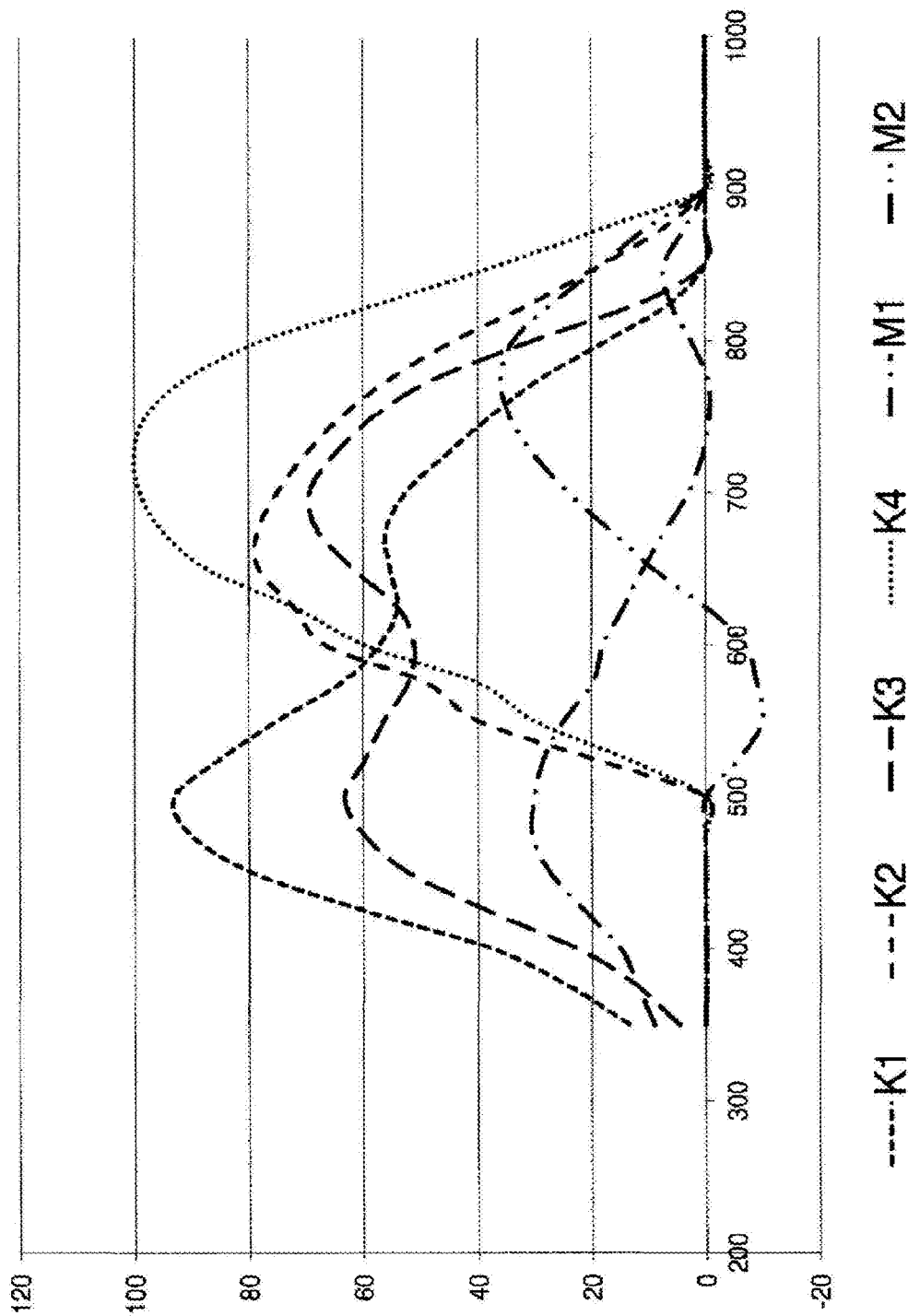
FIG. 19c shows an increase of spectral resolution by using combinations of different optical emitters with different optical detectors.
Figure 19D:
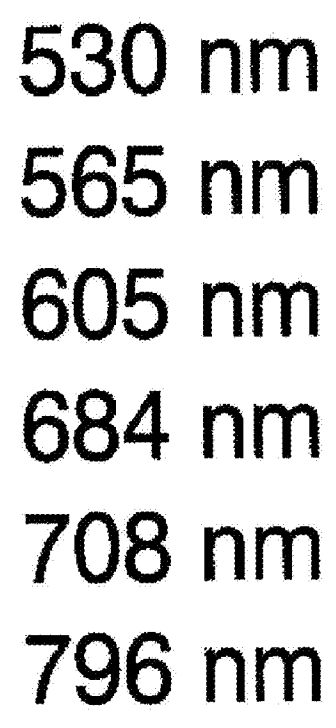

FIG. 19a shows the relative spectra of the two emitters E1 and E2. According to the invention, wide-band emitters are also purposefully used here. Wide-band emitters in an advantageous configuration are well-suited for detection of general properties of the sample that are not oriented towards a special substance. Narrow-band emitters are also used. In an advantageous variant, the narrow-band emitters are used for detection of special substances. FIG. 19b shows the relative spectra of the two detectors S1 and S3. It is recognisable that the spectrum from E2 matches detector S3 well and E1 matches S1 well. In a known solution variant, two different wavelengths would be measured, because E2 would be measured with S3 and E1 would be measured with S1. FIG. 19c shows an inventive optimisation of the arrangement. In addition to the indicated measuring paths K1:E1→S1 and K4:E2→S3, the paths K3:E1→S3 and K2→S1 are measured. The results are visualised in K1 to K4. The curves show the sensitivity of the measuring paths depending on the wavelength. With use of evaluation algorithms explained later in this document, M1 and M2 are also obtained as results of mathematical operations between measurement results from K1 to K4. FIG. 19d shows a table that lists the emphases of curves K1 to K4 and M1 to M2 sorted by wavelength. With the combination of the variation of wavelength characteristic for light emitters and light detectors, a recognisably finer wavelength resolution has been achieved.

Advantageous Spectral Configuration

In an advantageous configuration, at least 3 different spectral characteristics are realised with the light emitters.

In an advantageous configuration, at least 2 or 3 different spectral characteristics are realised with the light detectors.

In an advantageous configuration, a larger number of usable wavelength characteristics is yielded in a combination of light emitters and light detectors than there are emitters with different wavelength characteristics and detectors with different wavelength characteristics.

In an advantageous configuration, a larger number of usable wavelength characteristics than there are emitters with different wavelength characteristics and than there are detectors with different wavelength characteristics is yielded by using a combination of light emitters and light detectors.

In advantageous variant, the number of usable wavelength combinations increases by connecting the detectors to a measuring circuit with an especially high dynamic range.

In an advantageous configuration combinations of emitters and detector pairs arise, which, despite different spectral characteristics of the light emitters in combination with the light detectors, result in similar overall spectral characteristics like other pairings. These pairings are used in an advantageous variant in order to realise a better variation of optical path orientations and optical paths lengths, as well as different measuring locations in accordance with the other sections of this description.

Advantageous Geometric Arrangement

In advantageous arrangements the light sources emit different wavelengths.

The LED identified as LEDxx-yy below is the LED at the intersection point of the row signal yy is identified with the column signal xx from FIG. 11.

The arrangement shown in the example is symmetrical and regular, which, however is not a requirement. Advantageous arrangements can also be asymmetrical and irregular, because, for example, a larger number of optical path lengths can be achieved as a result.

If a wavelength is especially important, it can be applied to the positions LED32-22, LED34-22, LED32-24 and LED24-34, because a large quantity of short optical paths is yielded as a result. In an advantageous variant this or a comparable position is occupied by an LED with a wavelength at which the substance to be measured either reflects or absorbs. In an alternative advantageous variant this or a comparable position is occupied by an LED that permits an estimation of the general absorption and is not in a spectral range in which a substance to be measured absorbs or reflects.

In an advantageous arrangement, the emitters of the described wavelength are positioned such that the shortest distance of an emitter in this position to the detectors occurs at least two times. In an advantageous alternative the shortest distances differ by less than 25% in their length. Alternatively, this can be 50% or 80%. In an especially advantageous arrangement the optical paths of the light of this wavelength differ in their orientation.

This applies similarly for arrangements in which emitters and detectors are interchanged.

For certain wavelengths it is especially important to have especially short paths through the object to be measured. This is due, in part, to the fact that light of certain wavelengths is heavily absorbed in the skin, which is a frequent measuring object. This is also due to the fact that short path lengths measure primarily light portions that have not penetrated deep into the object to be measured. If a determination should be made for substances that are primarily in these layers close to the surface, characteristic wavelengths must be measured, if necessary, with short optical path lengths.

In advantageous variants, however, concentrations of deeper layers are also identified in the measuring object by removing the influence of the layers close to the surface. For this purpose this influence must first be measured by means of measurements with a short optical path length. As an alternative to this, optical paths that have penetrated to different depths of the tissue due to different emission characteristics are mathematically combined with each other.

The arrangement shown in the example has an especially short optical path length for LED31-22, for instance.

In an advantageous variant of the invention, emitters that emit in a wavelength range for which detection with a short optical path length is advantageous are arranged at positions having a short distance to the detector. In an especially advantageous variant, emitters and detectors are arranged immediately next to each other.

In an advantageous variant, LEDs with important wavelengths occupy more than one position adjacent to the detector. In the example, this could be LED31-22, LED33-24 and LED35-22.

In an alternative advantageous variant, LEDs of various wavelengths occupy the directly adjacent positions in order to be able to conduct measurements for many wavelengths with a short optical path. In the example, LED33-23 could emit 670 nm, LED31-21 660 nm, LED33-24 650 nm, LED33-21 640 nm, LED33-22 630 nm and LED33-25 620 nm.

In an advantageous arrangement, the emitters are arranged around the detectors such that the spatial arrangement in the surface allows multiple adjacent neighbours with short optical paths to a detector. In an advantageous variant, the optical paths differ in their direction and orientation in an advantageous variant by at least 85°, in an alternative variant by at least 40° and in another alternative variant by more than 20°, in a further alternative variant by more than 10° or 5° or by more than the deviation based on production tolerances of a line arrangement.

This applies similarly for arrangements in which emitters and detectors are interchanged. This text refers in part to an optical component that could be an emitter for light or a detector for light and its partner. The partner of an optical component is, with detectors, a component that can emit light and, with emitters, a component that can detect light. During the measurement, the light travels along the path between the component and its partner, wherein the part of light that finds this path is typically measured. A connecting line from a component to its partner is to be understood as the line from the averaged emission location of the light-emitting surface to the averaged detection location of the light-sensitive surface. The distance of an optical component to its partner should be considered the length of this line if the distance between the housings is not meant.

In an especially advantageous arrangement, the concepts are combined.

For example, an especially important wavelength is positioned at the positions LED31-22, LED33-22, LED35-22, LED31-24 LED33-24 and LED35-24, whereas the comparable positions LED31-23, LED33-25 and LED35-23 are occupied by a somewhat less important wavelength which is, however, still important enough that redundant measurement is desired. The also comparable positions LED31-25 LED33-23 and LED35-25 are occupied by 3 additional different wavelengths.

The number of optical path lengths for the respective wavelength can be adapted to the requirements of the measurement by using the two-dimensional arrangement.

According to the invention, an arrangement is used in which the optical paths arise as a combination of the positions of emitters and detectors that are arranged not just in a line or a recognisably close proximity of a line.

According to the invention, optical paths arise that are not parallel and have orientations that differ from each other by at least 3°, 10°, 25° or 40° in an advantageous manner.

According to the invention, the arrangement produces optical paths with which the number of equal-length optical paths of a wavelength differs from the number of equal-length optical paths of another wavelength. In this connection, equal-length should not be interpreted as only the exact equal length and should instead be interpreted such that it also covers acceptable differences in the scope of the measurement, which arise, for instance due to production imprecisions or the minimum technically feasible distance of components to be positioned next to each other.

In particular, equal-length should be interpreted if the differences in distances are less than 30% or 20% or 10% of the maximum optical path length.

In particular, more than 2 nearly equal-length optical paths of a wavelength arise in an advantageous variant.

In an advantageous variant, detectors and emitters are arranged such that the distribution of optical path lengths is different for the different wavelengths. The result is wavelengths with a spatial resolution of optical path lengths in the range of paths that are shorter than the maximum distance having a finer path length resolution than optical paths with other wavelengths, with "maximum distance" being defined as a distance that is so long that using it makes limited sense due to the long distance. In an advantageous variant, path length distances for one wavelength are finer by a factor of less than 0.9 or in a more advantageous way, by a factor of less than 0.8 or by a factor of less than 0.6, or by a factor of less than 0.3 than with other wavelengths.

In particular, in an advantageous arrangement, at least one optical path distance is yielded between two optical paths having the same wavelength that is less than 100% of the detectors size, emitter size or the distance of two components of these two categories. An especially advantageous arrangement yields 50% of the detector size or, in an even more advantageous arrangement, 20%, 10% or even 5%.

In an advantageous variant, optical path lengths can be achieved with the described arrangement that can differ by the following factors from the distances of detectors. In an advantageous variant the optical path length differences of one wave length are less than twice the detector distance, in an especially advantageous variant less than the detector distance and in an even more advantageous variant less than 55% of the detector distance.

In an advantageous variant there are many fine graduations in the optical path lengths for larger optical path lengths.

In a typical implementation of the invention the number of significantly different optical path lengths is greater than the number of detectors and greater than the number of emitters.

In a typical configuration of the invention the number of optical paths is the product of the number of emitters and number of detectors.

In an advantageous configuration, not all optical paths of a wavelength differ significantly in length.

In order to be able to better influence the penetration of the sample, multiple matrix-type sensor arrangements are used in an advantageous variant of the invention. An example of such an arrangement is explained in FIG. 16 and the corresponding figure description.

Emission Characteristic of the Emitters and Detection Characteristic of the Detectors To detect the inhomogeneity of a sample, particularly if it is biological tissue, the emission characteristic of the light into the sample and the detection characteristic of the measured light coming out of the sample play an important role. Since the light propagates in the sample in different optical paths depending on the irradiation angle region, the optical path variance can be influenced by the number of irradiation angle regions per light source. A higher variance provides better represents the inhomogeneity conditions of the sample.

It was determined in during examinations in a surprising way that a non-rotationally symmetric irradiation or deflection angle often results in a better consideration of the inhomogeneity of the sample and a higher precision in determining the concentration of analyte.

In an advantageous version, at least two different preferred angle regions of irradiation at each irradiation location for each light source and at least two different preferred angle regions for the detection angle at each detector for the detection of the light exiting the sample are realised.

In an additional advantageous version, the realisation of different preferred angle regions takes place with the purposeful design of a light barrier that impedes the crosstalk of the light from the emitter to the detector. As a component, the light barrier completely shields the emitters and detectors from each other after its application in an advantageous variant. In an advantageous variant, emitters and detectors each have their own cavity with a purposefully tailored geometry.

Preference is given to a version in which the light barrier has a geometry with corners and an even more advantageous version has a rectangular geometry. With a rectangular geometry, two vastly different preferred angle regions can be adjusted with an emission of photons in angles preferably from 5°-175° to the irradiation and detection surface in an advantageous variant. The packing density of the emitter and detector arrangement enclosed by the light barrier is higher with a rectangular configuration according to the invention than with a round geometry of the light barrier.

FIG. 18 shows an arrangement with a rectangular arrangement of the light barrier based on the example of optical emitter 1 in the centre of the device. Further explanation and advantageous configurations for this can be found in the figure description.

Design of the Light Barrier

Preference is given to a version in which the light tightness at the contact point of the light barrier and printed circuit board of the emitters and detectors is achieved with purposeful heating of the circuit board. A light barrier produced in plastic melts/softens in the region of the contact surface and thus closes a possible gap between the contact surface and light barrier. In an advantageous design, printed circuit board tracks that enable a heating of the appropriate position are arranged on the printed circuit board. An example of design is shown in FIG. 10 and explained in the corresponding figure description.

Preference is given to another solution in which the emitters and detectors are first completely cast with a material that is impermeable to light and then thin slits are made (e.g. using a fine saw blade), which penetrate into the casting material to the bottom of the emitter-detector plane. The slits are then cast with a material that is impermeable to light.

Description: FIG. 13 Description of a Device 1

FIGS. 13, 14 and 15 show examples of an advantageous configuration of the light barrier in a sectional view. Further explanations and advantageous configurations can be found in the figure description.

Spectral Analysis of the Sample

In order to detect the substance to be detected, light of one or multiple wavelengths that is absorbed or reflected by the substance is used. In some cases the substance is also excited with a wavelength and then the light of another wavelength is emitted, which is then detected. This can take place, for instance with luminescence and Raman scattering, which can also be used for detection.

Since a multitude of substances is normally present in the sample, the influence of substances having an optical effect in the region of the wavelengths that are relevant for the substance to be analysed is compensated for. For this purpose, additional wavelengths from which correction values can be determined are used for the measurement. These correction values can have a direct relationship with the concentration of one or multiple other substances, or they can be wavelengths that are located next to the wavelengths for detection of the substance and that they detect the optical characteristic of all substances in the sample near the wavelength to be analysed. The algorithmic processing is described in the chapter on the evaluation algorithm.

In the state of the art there are arrangements in which two or more wavelengths are measured. In the process, for instance, multiple light emitters of different wavelength are used. Detectors that are optimised for the wavelength of the light emitter are used for each sort of emitters.

In the present invention the spectral resolution of the arrangement is increased by purposefully combining different emitters with different detectors.

This is shown in FIG. 19a to d. The figure description includes information about the advantageous configuration and application processes, as well as example configurations.

In an advantageous configuration combinations of emitters and detector pairs arise, which, despite different spectral characteristics of the light emitters in combination with the light detectors, result in similar overall spectral characteristics like other pairings. These pairings are used in an advantageous variant in order to realise a better variation of optical path orientations and optical paths lengths, as well as different measuring locations in accordance with the other sections of this description.

Evaluation Circuit

In order to be able to use numerous emitter-detector pairs for better measuring precision and repeat accuracy, high dynamics of the detectors are required, because both a large number and a low number of photons are detectable and can be differentiated from the noise.

The invention results in high dynamics in an advantageous way such that a larger number of emitter-detector pairs for detection of inhomogeneity of the sample is available with the same number of emitters and detectors. A reproducible measuring result can thus be obtained with a lower number of components.

Advantageous Evaluation Circuit for the Detectors

In order to be able to connect the characteristically high number of optoelectronic components with low technical difficulty, various designs of the evaluation circuit are advantageous. Some examples of this are shown in FIG. 12. Different variants are shown in FIG. 12 and in its description. It is advantageous to use only one of these variants in an advantageous configuration. The figure description explains examples and advantageous variants.

In an advantageous variant, detectors that transmit data via a digital interface are used as components. In an advantageous variant this is a bus system, such as I2C or SPI. In an advantageous configuration this enables simpler wiring and higher packing density.

In an advantageous variant of the invention the measured light quantity is detected by the detectors, wherein capacities are charged and discharged. Advantageous configurations and processes and example implementations and processes are shown in FIG. 17 and explained in the figure description.

It is advantageous in the configuration described in FIG. 17 that no information about the brightness to be expected is required at the beginning of the measurement. By comparison, processes working with the switchover of amplifiers have the disadvantage of having to be initially measured in the most insensitive measuring range. Then a switch to a low signal in a more sensitive range takes place and measurement takes place again. In the described detector arrangement in the form of a matrix, this would be a major disadvantage, because the measuring time for determining flickering light has a fixed length and thus two or more measuring times are required. Therefore, the measurement becomes significantly slower and only a lower number of optical paths can be measured in the total available measuring time. The inventive design does not have this disadvantage. The brightness value to be measured does not need to be known at the beginning of the measurement. Measurements according to the modes explained in the figure description (Mode D, Mode A, Mode Z and Mode M) all occur simultaneously. The correct mode can be selected dynamically from the data accumulating during the measurement without having to restart the measurement. This is very advantageous, because with measurements on human skin the absorption varies heavily due to different skin types or different concentrations of analyte. Since the light attenuation through the skin with, for instance, skin type 5 is significantly greater than with skin type 1, the signal-noise ratio changes for the measurement. Depending on these conditions, measurement in accordance with the invention takes place in a mode that also enables exact determination of the analyte to be measured with a greater emitter-detector distance. Therefore, a variation of the exposure times for improvement of the signal-noise ratio is not necessary with the inventive configuration of the measuring circuit in an advantageous variant.

The described circuit variant can also be implemented in alternative variants in which, for instance, charging and discharging processes are exchanged.

In an alternatively advantageous variant, a current is initially amplified by the detector and converted from analogue to digital in an advantageous variant.

In an advantageous variant the brightness measurement is performed multiple times in order to detect and/or compensate for fluctuations as they occur, for instance, due to periodic or steady physiological changes. Changes to the measurement and environmental conditions can also be compensated for or purposefully utilised. An example is the undesired heating of the sensor during the measurement, the influence of which can be better compensated for with repeated measurement. The heating can also take place purposefully, for instance, in order shift the wavelength characteristic.

Process for More Precise Determination of Measurement Values with Use of Additional Information In an especially advantageous variant of the invention, compensation for errors of the device is achieved through detection of environmental influences with additional sensors. In particular, the following sensors can be used:

Temperature

Moisture of the sample on its surface, particularly the contact surface for the emitter-detector arrangement Moisture of the sample interior (e.g. via high-frequency or capacitive measurements)

Air gaps between sample and emitter-detector arrangement (e.g. via capacity measurement, application pressure measurement, triangulation)

Roughness of the sample surface (e.g. due to optical or capacitive sensors, e.g. finger print sensor)

Colour Abnormalities of the Sample Surface

Conductivity of the tissue of the user (various processes), pressure exerted with application of the arrangement on the sample, e.g. skin In an advantageous variant the information of these sensors and the optical measurement values of the device are used to estimate the measuring uncertainty or standard deviation. For this purpose, the measurement values of past measurements and their time difference can also be used. In particular, statistical information about measurement values and the distribution of the measurement values can also be used.

In an advantageous variant, the estimated measuring uncertainty or standard deviation is used in order to determine the number of measurements required to achieve a desired precision.

In an advantageous variant the result is shown to the end customer in discretised values. This prevents the customer from drawing incorrect conclusions, e.g. about their health status, based on measurement fluctuations. In the process measurement results that, for instance, represent a concentration are assigned to categories.

The last result of this user (how the user is differentiated from other users is explained below) is incorporated into the decision regarding the classification of the measurement result in a category in an advantageous way. Therefore, the probability of changes visible for the user over time that are due to measurement uncertainties can be reduced in an advantageous variant. In an advantageous variant, the visibility (or perception) of relevant changes of the measurement value for the user is not significantly delayed by this method.

In an advantageous variant, one or multiple additional measurements can be conducted if the measurement data or the history of measurement data or other data indicates that the decision regarding which result classification should be shown to the user is influenced too heavily by measurement uncertainties. In an advantageous variant, for instance, additional measurements are conducted if the measurement results are in the boundary region between two discrete output levels.

In an advantageous variant the indicated additional sensors can be used in order to provide advantageous environmental conditions for the measurement. For instance, temperature and moisture sensors can be used in order to provide advantageous conditions for the measurement using elements that can influence the parameters. For instance, the device or the surface of the optoelectronics can be heated in order to reduce/prevent a temperature drift due to contact with the sample. Moisture can, for instance, be brought to an advantageous range by using airflow that is blown through small openings in the surface of the emitter-detector arrangement. The distance of the sample to the emitter-detector arrangement can, for instance, be reduced by extracting the air between the surface of the optical electronics and sample and the sample is thereby practically aspirated. An unfavourable measurement location can be changed with a signal to the user to use a different measurement location or by showing the quality of the measuring location to the user.

Some of the known processes for improvement of the measuring situation are also applicable in an alternative variant without corresponding additional sensors.

Calibration measurements on the respective skin conditions of a user can take place by mechanically moving the device over the skin and permanently generating measurement results with multiple emitters and receivers in a matrix-like arrangement such that a 2 or 3-dimensional topography of measurement values over the desired measurement space arises. With a subsequent measurement in which the device does not necessarily have to be moved any more, the new measurement location can be incorporated into the topographical image such that, for instance, the earlier determined carotenoid value can be compared with the newly determined carotenoid value. Changes can thus be identified more precisely and earlier, because with an inhomogeneous distribution of a substance, such as the carotenoids, the corresponding local concentrations can be compared with each other. Since each subsequent measurement usually does not take place in the same measurement location, the actually measured change is not directly communicated to the user. It could be that the previous measurement has taken place in a location with lower or higher concentration and the change is only caused by the new measurement location. The output of the new measurement value could cause the user to make incorrect assessments. The output measurement value can, thus be calculated, for instance, with reference to earlier measurements as an arithmetic means such that no numerical change from earlier measurements arises for the user. With an additional indicator in the form of an arrow that indicates the rising, falling or consistent tendency, however, the actually identified change in an advantageous variant is represented.

The precision of the change determination can still be improved in that the 2 or 3-D topography incorporates, for instance, the carotenoid concentrations based on different depths of the skin. For instance, concentration gradients for carotenoids in the skin are known. If the concentration determination in individual skin layers is carried out using the known SRR method (f. U.S. Pat. No. 7,139,076 B1), it may be possible that changes are not identified in all skin layers. Therefore, the comparison can relate to specific skin layers having concentration level temporally or physiologically precedes a different position. Based on this knowledge, the user can derive further information that help him trace a consciously or unconsciously initiated change in a way of living (duration of sleep, nutrition and alcohol consumption) to a specific action. The resulting learning effect helps the user to act accordingly in the future, which can be advantageous, for instance, in the sense of prevention (reduction of the risk of future illness).

Tracing measured concentrations to specific behaviours can also be improved if information that the user provides in written answers in the form of a questionnaire is processed in addition to the pure skin measurements. This questionnaire can be evaluated as a 2-D or 3-D topography, wherein this topography is applied with local reference with the 2-D or 3-D measurement topography described above by means of, for instance, superimposing the two. In the process, peaks can meet valleys or peaks can meet peaks such that a specific relationship can be determined from this constellation.

Coupling

Preference is given to a design in which emitters are positioned around the perimeter on the edge of the emitter-detector distribution. The comparison of measurement values enables the checking of the correct coupling of the overall emitter-detector arrangement on the sample. With measurements on the inner surface of the hand, it can be determined whether a flat emitter-detector arrangement is applied all around in the same way based on the curvature of the ball of the thumb. Locally different coupling conditions sustainably influence the measurement result in specific applications.

It has been determined in a surprising way that by comparing threshold values for the received light of emitter-detector pairs in which the emitter is arranged in the edge region and for pairs having the same distance, in many applications it is possible to differentiate a complete coupling of the emitter-detector arrangement from an incomplete coupling. In an advantageous configuration of the invention, the coupling of the sample is measured and monitored. In an advantageous configuration this takes place by applying threshold values to the light measured on selected optical paths.

The checking of the coupling takes place at the beginning of the measuring procedure in an advantageous version. With incomplete coupling, the measurement is immediately interrupted in an advantageous variant, which would spare unnecessary measuring time. The user is prompted to repeat the measurement by outputting a message.

In an alternative variant, repeat measurement does not take place. The evaluation of the measurement can refrain from consideration of the relevant edge zone region such that only optical paths for which the coupling was correct are factored in.

If the incomplete application of the emitter-detector arrangement results in a regular light gap between the tissue surface and emitter-detector surface, which leads to a penetration of external light, preference is given to a version in which the determination is achieved by measurement of the brightness value with the emitters of the device switched off.

However, the checking of the coupling does not only apply to the incomplete application of the emitter-detector arrangement on the sample; it also applies to changed coupling conditions due to partial moisture or fatty formations on the skin surface, local soiling, pigment disturbances, injuries, scars, etc. Coupling problems become more recognisable with more comparisons of equal optical paths and they can be eliminated by disregarding the relevant partial measurements or by a purposefully repeated measurement. According to the invention, therefore, both the measurement accuracy and the repeat accuracy of the measurement are improved.

Preference is given to a design in which moisture sensors applied on the surface of the device, which is in contact with the sample for the measurement, are used to check the moisture conditions on the sample surface.

Temperature Drift of the Light Source

If LEDs are used as emitters, their optical spectrum shifts as the emitter heats up when the LED is activated. When measuring biological tissue, a shift takes place due to the body temperature with application of the device on the skin. As the temperature gradient becomes higher, the temperature drift also increases. With temperature control of the emitter-detector arrangement, the temperature gradient can be reduced. It was determined based on measurements that some additionally applied conductors used as a heating element were sufficient in order to increase the temperature on the plane of emitters and detectors at the start of the measurement such that it corresponded to the human body temperature for in vivo measurements. It could thus be determined in a surprising way that the repeat accuracy of the measurement is improved with this measure.

Process for Calculation of Physiological Parameters or Substance Concentrations

The process is used to determine substance concentrations, such as the carotenoid concentration in human skin or other samples. Alternatively, physiological parameters can also be determined, such as the degree to which the skin is protected from ageing or solar radiation.

In particular, substance concentrations at specific locations of the skin (on the skin surface) and in depth (vertically in relation to the surface) or relative to specific marker points on the skin can also be determined. Such marker points can be artificially applied points (visible or invisible markers applied on or in the skin) or natural markers. Example of natural markers are the layer boundaries between the epidermis and dermis or a vein running through the tissue.

In particular, the values to be determined can not only be determined with spatial resolution, but also as an average value.

An especially advantageous variant of a calculation system, is presented below. It is recognisable for a person skilled in the art that a multitude of possibilities of implementation of the calculation sequence or the supplementing or omission of calculation steps is possible without diverging from the basic approach of the process.

The calculation process uses data that originates from the described detectors. These are essentially brightness values as well as values of other sensors (such as temperature sensors and user input), that are used, for instance, as correction factors.

Step 1: Pre-Processing Correction

The normal pre-processing steps can be applied to the measurements and to virtual measurements that are explained below. These two types of values are identified hereinafter as YS0. Typical examples for pre-processing steps include compensation for dark values, offset correction or pulsed operation, the consideration of different amplification factors or a linearity correction. In particular, a correction based on known or estimated physical properties of the sample is also possible. These can be measured, tabulated or derived from physical models. In particular, different values, especially measurement values, can also be incorporated into the correction equations.

The obtained values should be identified in the following as YS1.

For simplification of the notation, the various YS1 values are summarised in the description below. Of course, YS1 of each measurement value that has been taken is meant such that YS1 is representative for the following values, e.g.:

YS1 brightness recorded by photodiode 1 when LED 1 illuminates

YS1 brightness recorded by photodiode 2 when LED 1 illuminates

YS1 brightness recorded by photodiode 1 when LED 2 illuminates

YS1 brightness recorded by photodiode 2 when LED 2 illuminates

YS1 brightness recorded by photodiode 10 when LED 20 illuminates

YS1 temperature of LED2

YS1 temperature of the skin

YS1 brightness recorded by photodiode 1 when LED 1 illuminates measured at time 1

YS1 brightness recorded by photodiode 1 when LED 1 illuminates measured at time 2 and so forth

Step 2: First Weighting

The information gathered from step 1 can be weighted; this is carried out most easily by multiplying with a constant.

Weighting can also involve a non-linear function. Weighting with polynomials is especially advantageous. Polynomials of the 4th degree of the form $YS2=K3*YS1^3+K2*YS1^2+K1*YS1+K0$ are especially advantageous.

Additional advantageous is weighting with exponential functions of the form:

$$YS2=K4*K5^{(YS1*K6)}$$

Logarithmic functions for similar applications purposes are also known from the literature:

$$YS2=K7*\text{LOG}(K8*YS1; \text{ in base } K9)$$

In an especially advantageous variant, a linear function defined section by section is used. Linear interpolation can take place between the stored support levels.

The functions can be selected with modelling of the problem. However, in many cases the selection of the function and the parameters are determined with the extraction of a quantity of measurement values from test specimens or phantoms for which the correct result is known (e.g. with a reference process). Then a computer iteratively tests which combinations of algorithms and constants are suitable for a good representation of the measured values based on the correct results.

This process also applies for the following steps in an advantageous variant.

The constants can assume different values for each measurement. The notation of K is shown in a simplified form here, wherein sub-indexes of K K . . . are omitted.

An important variant of the weighting is temporal filtering. In particular, measurement values can be beneficially weighted using low-pass filters. For this purpose, the time of the measurement and the history of output values YS1 are included in the calculation in an advantageous variant. The history of selected values is stored for this purpose in an advantageous variant. Additional typical variants include diffusion equations that can describe the diffusion of substances through the tissue and the resulting behaviour of concentrations over time. They are often described differently by variants of exponential functions, such as with differential equations.

Step 3: Compensation

The values obtained for YS2 from step 2 are now mathematically combined with each other so that disturbance variables or signals are omitted or emphasised.

Some new values YS3 are formed for this purpose.

The values YS3 are determined by means of summation in an advantageous variant:

$$YS3 = K101 * YS2_{Index1} + K102 * YS2_{Index2} + \ldots K_{XXX} * YS2_{Index\ N}$$

In an alternative advantageous variant the YS3 are determined by product formation:

$$YS3 = YS2_{Index1}{}^{K201} * YS2_{Index2[<]BEGINITALmK}{}^{202} * \ldots * YS2_{Index\ N}{}^{K_{XXX}}$$

In this process, it may often be the case that different YS2 calculations are used for the determining YS3 results. The YS2 are thus calculated with partially different processing functions and different constant values.

The YS3 are determined in an advantageous variant such that they represent specific properties of the sample to be studies with respect to specific locations or wavelengths.

An additional advantageous variant is the use of a neuronal network for determining YS3.

An additional advantageous variant is the determination of YS3 values with statistical processes. These are, for instance average determination or median calculation. However, clustering processes can also be applied to vectors from multiple YS2. An example is the described recognition and weighting of outliers based on known standard deviations. Kalman or Wiener filters are also examples.

An especially advantageous variant incorporates the geometric factors of the emitter detector arrangement into the process. This includes distances of locations of light transmission and light reception, as well as the expected optical paths of the photons passing through the sample. Since the volume through which the light passes depends on scattering and absorption and this can be parameters determined, implementing a dependency of the volumes on YS0 and YS3 is advantageous. It is often advantageous to calculate which volumes the light of an LED/light receiver combination have in common and which they do not have in common and determine the averaging factors therefrom.

Processes for classic image processing can also be applied.

In an especially advantageous variant, YS2, the comparable emitter-detector pairs belonging to a group are each summarised as at least one YS3. In an advantageous variant these YS3 are virtual measurement values, as explained in step 4. In an advantageous variant, these virtual measurement values are then summarised in an additional step 3 in order to determine the resulting concentration value therefrom.

Step 4: Obtaining Virtual Measurement Values

Some of the YS3 are now defined as virtual measurement values. Steps 1 to 4 can be executed again using these values.

This is an advantageous method because similar calculations can always serve as a basis for obtaining the calculation result. In particular, automatic determination of the calculation functions and the constants to be used in the calculation are made significantly easier as a result.

In many cases, multiple effects must be compensated for in order to obtain the end result.

For example, undesired effects of diverse blood circulation of the test specimen can be compensated for by carrying out steps 1-4 a first time.

By returning the results YS3 to additional YS0 values, measurement deviations based on varying surface coupling can be equalised by conducting steps 1 to 4 a second time.

Then the general tissue absorptions can be then separated from the absorption of an interesting substance (e.g. carotenoids) by conducting steps 1 to 4 a third time.

Finally, one or multiple concentration values of an interesting substance calculated in this manner can be allocated to a physiological value by performing steps 1 to 4 a fourth time. This can, for instance, be a recommendation for future behaviour, such as described in the following two examples.

Example 1: The Fitness Value of the Skin is X (Wherein X Originates from a Scale from 1 to 10)

Example 2: The Probability that Tomatoes Consumed During the Next Meal Will Promote the Health by a Specific Value is xxx %

The processing of life circumstances that have been input or detected in another manner as YS0 values is also particularly advantageous for such statements.

In order to be able to apply steps 1 to 4 repeatedly, it must be determined which YS3 values are output to the user and which are only used as intermediate variables.

In an advantageous variant, some of the processes and constants, as well as the number of YS3 that are used are specified by the person such that the known system (e.g. the human skin and the device that is used) is described. The other constants are determined by a computer, e.g. based on a measurement with the test specimen or phantoms in which correct values obtained per reference are present. The processes for this can be PLS (Parital Least Squares), main component analysis, genetic algorithms or systematic sampling.

In an advantageous variant, the system can also be trained to YS3 intermediate results that are obtained with a reference measurement. This can be, for instance, the scatter and absorption coefficients of skin that have been measured based on samples. As is known, these variables are important for measurements on human skin, such as the carotenoid measurement, and are thus a useful variable in order to define them as an intermediate variable and to train the recognition thereof separately before the actual output variable is trained. Therefore, processes and groups of constants can also be kept constant during the training process of the output value, whereas others are available for purposeful iterative modification.

In an advantageous variant the YS3 represent concentration values of a substance at a specific depth in the sample, especially a skin sample.

The described evaluation process offers decisive advantages for the described device. FIG. 10 shows an example configuration of a device. This comprises 100 light emitters and 40 light detectors. In addition, this is evaluated repeatedly for a measurement such that 20,000 measurement values are obtained. Manual creation of the evaluation algorithm for such a large number of measurement values is hardly possible without the use of a basic framework as described above. However, with the use of the algorithm framework described above, determination of the algorithm and constants with computer-assisted optimisation processes is possible.

The present invention is not limited to embodiments described herein; reference should be had to the appended claims.

The following is claimed:

1. A method for optical measurement of carotenoids or antioxidants in a sample of human or animal tissue or blood, the method comprising:
    positioning a contact surface in contact with the sample;
    emitting photons from a first optical emitter, through a first emission area of the contact surface, and into the sample;
    detecting at least a portion of the photons emitted from the first optical emitter, which traveled through the sample, through a first detection area of the contact surface, and to a first optical detector to produce a first measurement;
    detecting at least a portion of the photons emitted from the first optical emitter, which traveled through the sample, through a second detection area of the contract surface, and to a second optical detector to produce a second measurement;
    emitting photons from a second optical emitter, through a second emission area of the contact surface, and into the sample;
    detecting at least a portion of the photons emitted from the second optical emitter, which traveled through the sample, through the first detection area of the contact surface, and to the first optical detector to produce a third measurement;
    wherein the first emission area is spaced apart from the first detection area;
    wherein the first emission area is spaced apart from the second detection area;
    wherein the second emission area is spaced apart from the first detection area;
    wherein the second emission area is spaced apart from the second detection area; and
    determining a measurement of carotenoids or antioxidants in the sample based at least in part on the first measurement, the second measurement, and the third measurement.

2. The method of claim 1, comprising producing measurements for forty different emitter-detector pairs using a plurality of optical emitters and a plurality of optical detectors, wherein each of the plurality of optical emitters is part of multiple emitter-detector pairs, wherein each of the plurality of optical detectors is part of multiple emitter-detector pairs, and wherein the measurement of carotenoids or antioxidants in the sample is determined based at least in part on the measurements from the forty different emitter-detector pairs.

3. The method of claim 1, comprising:
    detecting at least a portion of the photons emitted from the second optical emitter, which traveled through the sample, through the second detection area of the contact surface, and to the second optical detector to produce a fourth measurement; and
    determining the measurement of carotenoids or antioxidants in the sample based at least in part on the first measurement, the second measurement, the third measurement, and the fourth measurement.

4. The method of claim 3, wherein:
    the first emission area is spaced apart from the first detection area by a first distance;
    the first emission area is spaced apart from the second detection area by a second distance;
    the second emission area is spaced apart from the first detection area by a third distance;
    the second emission area is spaced apart from the second detection area by a fourth distance; and
    the first distance and the fourth distance are approximately equal and the pair of the first optical emitter and the first optical detector have approximately the same wavelength characteristic as the pair of the second optical emitter and second optical detector, so that a difference between the first measurement and the fourth measurement is indicative of local variations of the sample along the path of the photons from the first emission area to the first detection area in comparison to the path of the photons from the second emission area to the second detection area.

5. The method of claim 4, wherein at least one of the second or third distance is different from the first distance, so that photons of at least one of the second and third measurement tend to travel at a different depth through the sample than the photons of the first or fourth measurements.

6. The method of claim 1, wherein:
    the first emission area is spaced apart from the first detection area by a first distance;
    the first emission area is spaced apart from the second detection area by a second distance;
    the second emission area is spaced apart from the first detection area by a third distance that is approximately equal to the first distance; and
    the first distance and the third distance are longer than the second distance, so that optical paths from the first and second optical emitters to the first optical detector tend to send photons deeper into the sample than the optical path from the first optical emitter to the second optical detector.

7. The method of claim 1, wherein:
    the first emission area is spaced apart from the first detection area by a first distance;
    the first emission area is spaced apart from the second detection area by a second distance that is approximately equal to the first distance;
    the second emission area is spaced apart from the first detection area by a third distance; and
    the first distance and the second distance are shorter than the third distance, so that optical paths from the first optical emitter to the first and second optical detectors tend to send photons less deep into the sample than optical paths from the second optical emitter to the first optical detector.

8. The method of claim 1, comprising:
    producing measurements for a first set of comparable emitter-detector pairs, wherein each of the comparable emitter-detector pairs of the first set has an optical emitter that is spaced apart from an optical detector by approximately the same first distance; and
    producing measurements for a second set of comparable emitter-detector pairs, wherein each of the comparable emitter-detector pairs of the second set has an optical emitter that is spaced apart from an optical detector by approximately the same second distance, which is different from the first distance;

wherein the measurement of carotenoids or antioxidants in the sample is determined based at least in part on the measurements for the first and second sets of comparable emitter-detector pairs.

9. The method of claim 8, wherein all the comparable emitter-detector pairs of the first set and the second set use approximately the same wavelength characteristic.

10. The method of claim 1, comprising:
producing measurements for a first set of at least two comparable emitter-detector pairs, wherein each of the comparable emitter-detector pairs of the first set has an optical emitter that is spaced apart from an optical detector by approximately the same first distance; and
producing measurements for a second set of at least two comparable emitter-detector pairs, wherein each of the comparable emitter-detector pairs of the second set has an optical emitter that is spaced apart from an optical detector by approximately the same second distance, which is different from the first distance;
producing measurements for a third set of at least two comparable emitter-detector pairs, wherein each of the comparable emitter-detector pairs of the third set has an optical emitter that is spaced apart from an optical detector by approximately the same third distance, which is different from the first and second distances,
wherein all emitter-detector pairs of the first set, the second set, and the third set have wavelength characteristics that are substantially equal;
wherein the measurement of carotenoids or antioxidants in the sample is determined based at least in part on the measurements for the first, second, and third sets of comparable emitter-detector pairs.

11. The method of claim 1, comprising determining light intensity at the first optical detector using at least two of the following modes:
using mode D:
producing a first current to charge or discharge a capacitive element, wherein current through the first optical detector produces a second current that counters the first current to limit the charging or discharging of the capacitive element;
measuring a voltage indicative of a voltage across the capacitive element, wherein the voltage across the capacitive element is indicative of current through the first optical detector; and
determining light intensity at the first optical detector based at least in part on the measured voltage;
using mode A:
producing a first current to perform one of charging or discharging a capacitive element to a first voltage;
enabling a second current through the first optical detector to perform the other of discharging or charging the capacitive element for a measurement time period;
measuring a second voltage indicative of the voltage across the capacitive element after the measurement time period;
determining light intensity at the first optical detector based at least in part on a difference between the first voltage and the second voltage;
using mode Z:
performing a plurality of charge-discharge cycles, wherein each of the plurality of charge-discharge cycles includes:
producing a first current to perform one of charging or discharging a capacitive element to a first voltage threshold; and
enabling a second current through the first optical detector to perform the other of discharging or charging the capacitive element to a second voltage threshold;
determining light intensity at the first optical detector based at least in part on a number of charge-discharge cycles performed during a measurement time period or based at least in part on a length of time to transition from the first voltage threshold to the second voltage threshold for one or more of the charge-discharge cycles;
using mode M:
performing a plurality of complete charge-discharge cycles, wherein each of the plurality of complete charge-discharge cycles includes:
producing a first current to perform one of charging or discharging a capacitive element to a first voltage threshold; and
enabling a second current through the first optical detector to perform the other of discharging or charging the capacitive element to a second voltage threshold;
performing a partial charge-discharge cycle by:
producing the first current to perform one of charging or discharging the capacitive element to the first voltage threshold; and
enabling a second current through the first optical detector to perform the other of discharging or charging the capacitive element to an intermediate voltage value between the first voltage threshold and the second voltage threshold; and
determining light intensity at the first optical detector based at least in part on a number of complete charge-discharge cycles performed during a measurement time period or based at least in part on a length of time to transition from the first voltage threshold to the second voltage threshold for one or more of the complete charge-discharge cycles, and wherein determining the light intensity at the first optical detector is also based at least in part on a difference between the first voltage threshold and the intermediate voltage value.

12. The method of claim 11, comprising determining light intensity at the at least one optical detector using at least three of Mode D, Mode A, Mode Z, and Mode M.

13. The method of claim 11, comprising:
determining a first light intensity of light that is received by the first optical detector from the first optical emitter using mode A; and
determining a second light intensity of light that is received by the first optical detector from the second optical emitter using one of mode M, mode Z, and mode D;
wherein a first distance between the first light emitter and the first optical detector is greater than a second distance between the second light emitter and the first optical detector.

14. The method of claim 11, comprising:
determining a first light intensity of light that is received by the first optical detector from the first optical emitter using one of mode A, mode M, and mode Z;
determining a second light intensity of light that is received by the first optical detector from the second optical emitter using mode D;

wherein a first distance between the first light emitter and the first optical detector is greater than a second distance between the second light emitter and the first optical detector.

15. The method of claim 11, comprising:
determining a first light intensity of light that is received by the first optical detector from the first optical emitter using a first mode that is one of mode A, mode M, mode Z, and mode D; and
determining a second light intensity of light that is received by the first optical detector from the second optical emitter using a second mode that is one of mode A, mode M, mode Z, and mode D;
wherein the second mode is different from the first mode.

16. The method of claim 1, comprising:
using the first optical detector to detect photons emitted by the first optical emitter using a first wavelength characteristic; and
using the first optical detector to detect photons emitted by the second optical emitter using a second wavelength characteristic;
wherein the second wavelength characteristic is different from the first wavelength characteristic.

17. The method of claim 1, wherein the first emission area for the first optical emitter overlaps with the second emission area for the second optical emitter.

18. The method of claim 17, wherein the first optical emitter and the second optical emitter have different wavelength characteristics.

19. A system for optical measurement of carotenoids or antioxidants in a sample of human or animal tissue or blood, the system comprising:
a first optical emitter configured to emit photons into the sample;
a second optical emitter configured to emit photons into the sample;
a first optical detector configured to receive photons that travel through the sample, wherein the first emitter and the first detector are spaced apart, so that photons emitted by the first optical emitter travel through the sample to be detected by the first optical detector;
a second optical detector configured to receive photons that travel through the sample; and
a controller configured to:
activate the first optical emitter to emit photons into the sample, and to activate the first optical detector and the second optical detector to detect resulting photons that exit the sample to produce a first light intensity measurement for the first optical detector and a second light intensity measurement for the second optical detector;
activate the second optical emitter to emit photons into the sample, and to activate the first optical detector and the second optical detector to detect resulting photons that exit the sample to produce a third light intensity measurement for the first optical detector and a fourth light intensity measurement for the second optical detector; and
a data processing system configured to determine a measurement of carotenoids or antioxidants in the sample based at least in part on the first light intensity measurement, the second light intensity measurement, the third light intensity measurement, and the fourth light intensity measurement.

20. The device of claim 19, wherein:
the first optical emitter is spaced apart from the first optical detector by a first distance;
the first optical emitter is spaced apart from the second optical detector by a second distance;
the second optical emitter is spaced apart from the first optical detector by a third distance;
the second optical emitter is spaced apart from the second optical detector by a fourth distance; and
the first distance and the third distance are different so that an optical path from the first optical emitter to the first optical detector tends to send photons to a different depth through the sample than an optical path from the second optical emitter to the first optical detector.

21. A system for optical measurement of carotenoids or antioxidants in a sample of human or animal tissue or blood, the system comprising:
a first optical emitter configured to emit photons into the sample;
a second optical emitter configured to emit photons into the sample;
a first optical detector configured to receive photons that travel through the sample, wherein the first emitter and the first detector are spaced apart, so that photons emitted by the first optical emitter travel through the sample to be detected by the first optical detector;
a second optical detector configured to receive photons that travel through the sample;
a controller configured to:
activate the first optical emitter to emit photons into the sample, and to use at least one of the first optical detector and the second optical detector to detect resulting photons that exit the sample to produce at least one light intensity measurement; and
activate the second optical emitter to emit photons into the sample, and to use at least one of the first optical detector and the second optical detector to detect resulting photons that exit the sample to produce at least one light intensity measurement;
a data processing system configured to determine a measurement of carotenoids or antioxidants in the sample based at least in part on the light intensity measurements;
additional optical emitters; and
additional optical detectors;
wherein the number of the optical emitters and the number of optical detectors are sufficiently high so that at least forty emitter-detector pairs are formed.

22. A system for optical measurement of carotenoids or antioxidants in a sample of human or animal tissue or blood, the system comprising:
a first optical emitter configured to emit photons into the sample;
a second optical emitter configured to emit photons into the sample;
a first optical detector configured to receive photons that travel through the sample, wherein the first emitter and the first detector are spaced apart, so that photons emitted by the first optical emitter travel through the sample to be detected by the first optical detector;
a second optical detector configured to receive photons that travel through the sample;
a controller configured to:
activate the first optical emitter to emit photons into the sample, and to use at least one of the first optical detector and the second optical detector to detect resulting photons that exit the sample to produce at least one light intensity measurement; and
activate the second optical emitter to emit photons into the sample, and to use at least one of the first optical detector and the second optical detector to detect resulting photons that exit the sample to produce at least one light intensity measurement; and a data processing system configured to determine a measurement of carotenoids or antioxidants in the sample based at least in part on the light intensity measurements;

wherein the first optical emitter is spaced apart from the first optical detector by a first distance;

wherein the first optical emitter is spaced apart from the second optical detector by a second distance;

wherein the second optical emitter is spaced apart from the first optical detector by a third distance;

wherein the second optical emitter is spaced apart from the second optical detector by a fourth distance; and wherein the second distance and the third distance are approximately equal so that light intensity measurements for light emitted by the first optical emitter and received by the second optical detector and for light emitted by the second optical emitter and received by the first optical detector have substantially similar geometric conditions.

23. A system for optical measurement of carotenoids or antioxidants in a sample of human or animal tissue or blood, the system comprising:

a first optical emitter configured to emit photons into the sample;

a second optical emitter configured to emit photons into the sample;

a first optical detector configured to receive photons that travel through the sample, wherein the first emitter and the first detector are spaced apart, so that photons emitted by the first optical emitter travel through the sample to be detected by the first optical detector;

a second optical detector configured to receive photons that travel through the sample;

a controller configured to:
activate the first optical emitter to emit photons into the sample, and to use at least one of the first optical detector and the second optical detector to detect resulting photons that exit the sample to produce at least one light intensity measurement; and activate the second optical emitter to emit photons into the sample, and to use at least one of the first optical detector and the second optical detector to detect resulting photons that exit the sample to produce at least one light intensity measurement; and a data processing system configured to determine a measurement of carotenoids or antioxidants in the sample based at least in part on the light intensity measurements;

wherein the first optical emitter is spaced apart from the first optical detector by a first distance;

wherein the first optical emitter is spaced apart from the second optical detector by a second distance;

wherein the second optical emitter is spaced apart from the first optical detector by a third distance;

wherein the second optical emitter is spaced apart from the second optical detector by a fourth distance; and wherein the first distance and the fourth distance are approximately equal so that an optical path from the first optical emitter to the first optical detector tends to send photons to substantially the same depth through the sample as an optical path from the second optical emitter to the second optical detector, to provide multiple measurements at different locations for substantially the same depth in the sample; and wherein the second distance is different from the first distance so that the optical path from the first optical emitter to the first optical detector tends to send photons to a different depth through the sample than an optical path from the first optical emitter to the second optical detector, to provide measurements for different depths in the sample.

24. A system for optical measurement of carotenoids or antioxidants in a sample of human or animal tissue or blood, the system comprising:

a first optical emitter configured to emit photons into the sample;

a second optical emitter configured to emit photons into the sample;

a first optical detector configured to receive photons that travel through the sample, wherein the first emitter and the first detector are spaced apart, so that photons emitted by the first optical emitter travel through the sample to be detected by the first optical detector;

a second optical detector configured to receive photons that travel through the sample;

a controller configured to:
activate the first optical emitter to emit photons into the sample, and to use at least one of the first optical detector and the second optical detector to detect resulting photons that exit the sample to produce at least one light intensity measurement; and activate the second optical emitter to emit photons into the sample, and to use at least one of the first optical detector and the second optical detector to detect resulting photons that exit the sample to produce at least one light intensity measurement; and a data processing system configured to determine a measurement of carotenoids or antioxidants in the sample based at least in part on the light intensity measurements;

wherein the first optical emitter is spaced apart from the first optical detector by a first distance;

wherein the first optical emitter is spaced apart from the second optical detector by a second distance;

wherein the second optical emitter is spaced apart from the first optical detector by a third distance that is approximately the same as the first distance;

wherein the second optical emitter is spaced apart from the second optical detector by a fourth distance; and wherein the first distance and the third distance are shorter than the fourth distance, so that optical paths from the first and second optical emitters to the first optical detector tend to send photons less deep into the sample than an optical path from the second optical emitter to the second optical detector.

25. A system for optical measurement of carotenoids or antioxidants in a sample of human or animal tissue or blood, the system comprising:

a first optical emitter configured to emit photons into the sample;

a second optical emitter configured to emit photons into the sample;

a first optical detector configured to receive photons that travel through the sample, wherein the first emitter and the first detector are spaced apart, so that photons emitted by the first optical emitter travel through the sample to be detected by the first optical detector;

a second optical detector configured to receive photons that travel through the sample;

a controller configured to:

activate the first optical emitter to emit photons into the sample, and to use at least one of the first optical detector and the second optical detector to detect resulting photons that exit the sample to produce at least one light intensity measurement; and activate the second optical emitter to emit photons into the sample, and to use at least one of the first optical detector and the second optical detector to detect resulting photons that exit the sample to produce at least one light intensity measurement; and a data processing system configured to determine a measurement of carotenoids or antioxidants in the sample based at least in part on the light intensity measurements;

wherein the first optical emitter is spaced apart from the first optical detector by a first distance;

wherein the first optical emitter is spaced apart from the second optical detector by a second distance that is approximately the same as the first distance;

wherein the second optical emitter is spaced apart from the first optical detector by a third distance;

wherein the second optical emitter is spaced apart from the second optical detector by a fourth distance; and wherein the first distance and the second distance are longer than the third distance, so that optical paths from the first optical emitter to the first and second optical detectors tend to send photons deeper into the sample than an optical path from the second optical emitter to the first optical detector.

26. A system for optical measurement of carotenoids or antioxidants in a sample of human or animal tissue or blood, the system comprising:

a first optical emitter configured to emit photons into the sample;

a second optical emitter configured to emit photons into the sample;

a first optical detector configured to receive photons that travel through the sample, wherein the first emitter and the first detector are spaced apart, so that photons emitted by the first optical emitter travel through the sample to be detected by the first optical detector;

a second optical detector configured to receive photons that travel through the sample;

a controller configured to:
  activate the first optical emitter to emit photons into the sample, and to use at least one of the first optical detector and the second optical detector to detect resulting photons that exit the sample to produce at least one light intensity measurement; and
  activate the second optical emitter to emit photons into the sample, and to use at least one of the first optical detector and the second optical detector to detect resulting photons that exit the sample to produce at least one light intensity measurement;

a data processing system configured to determine a measurement of carotenoids or antioxidants in the sample based at least in part on the light intensity measurements;

a capacitor that is electrically coupled to the first optical detector such that receipt of the photons by the first optical detector produces a discharge current through the first optical detector to discharge the capacitor; and circuitry configured to apply a charging current to charge the capacitor;

wherein the controller is configured to:
  apply the charging current to charge the capacitor during an initial charging action;
  measure a first voltage across the capacitor after the initial charging action;
  when the first voltage across the capacitor is below an upper threshold voltage, continue the charging current and measure the voltage across the capacitor to determine light intensity at the first optical detector for a first light intensity range;
  when the first voltage across the capacitor is above the upper threshold voltage, reduce or disable the charging current to enable the discharge current through the first optical detector to discharge the capacitor;
  monitor the voltage across the capacitor as the discharge current discharges the capacitor;
  when the voltage across the capacitor reaches a lower threshold voltage indicating an end of a first charge-discharge cycle, reapply the charging current and perform one or more additional charge-discharge cycles, and determine light intensity at the first optical detector for a second light intensity range based at least in part on a number of charge-discharge cycles performed during a measurement time period or based at least in part on a length of time for one or more discharge portions of the charge-discharge cycles, wherein the second light intensity range is lower than the first light intensity range; and
  when the measurement time ends before the voltage across the capacitor reaches the lower threshold voltage, measure a second voltage across the capacitor at the end of the measurement time, and determine light intensity at the first optical detector for a third light intensity range based at least in part on the second voltage, wherein the third light intensity range is lower than the second light intensity range.

27. A system for optical measurement of carotenoids or antioxidants in a sample of human or animal tissue or blood, the system comprising:

a first optical emitter configured to emit photons into the sample;

a second optical emitter configured to emit photons into the sample;

a first optical detector configured to receive photons that travel through the sample, wherein the first emitter and the first detector are spaced apart, so that photons emitted by the first optical emitter travel through the sample to be detected by the first optical detector;

a second optical detector configured to receive photons that travel through the sample;

a controller configured to:
  activate the first optical emitter to emit photons into the sample, and to use at least one of the first optical detector and the second optical detector to detect resulting photons that exit the sample to produce at least one light intensity measurement; and
  activate the second optical emitter to emit photons into the sample, and to use at least one of the first optical detector and the second optical detector to detect resulting photons that exit the sample to produce at least one light intensity measurement;

a data processing system configured to determine a measurement of carotenoids or antioxidants in the sample based at least in part on the light intensity measurements; and a capacitive element that is electrically coupled to the first or second optical detector such that receipt of the photons by the optical detector produces a current that charges or discharges the capacitive element;

wherein the controller is configured to:

measure a voltage indicative of a voltage across the capacitive element; and determine light intensity at the first or second optical detector based at least in part on the measured voltage that is indicative of the voltage across the capacitive element.

28. The device of claim 27, wherein the controller is configured to:
measure a first voltage indicative of a voltage across the capacitive element at a first time;
measure a second voltage indicative of a voltage across the capacitive element at a second time; and
determining the light intensity at the first or second optical detector based at least in part on a difference between the first voltage and the second voltage.

29. The device of claim 27, wherein the controller is configured to:
perform a plurality of charge cycles by:
charging the capacitive element;
discharging the capacitive element;
monitoring the voltage across the capacitive element to determine when a voltage threshold is reached to end the charge cycle;
determine the light intensity at the first or second optical detector based at least in part on either:
a) a number of charge cycles performed in a measurement time period; or
b) an amount of time charging or discharging the capacitive element with the current produced by detection of the photons for one or more of the charge cycles.

30. The device of claim 29, wherein the controller is configured to:
measure an end voltage indicative of a voltage across the capacitive element at an end of the measurement time period, wherein the light intensity is determined based at least in part on the end voltage.

31. A device for optical measurement of carotenoids or antioxidants in a sample of human or animal tissue or blood, the device comprising:
a contact surface configured to contact the sample;
an optical emitter configured to emit light through a first area of the contact surface and into the sample;
an optical detector configured to receive light from the sample through a second area of the contact surface, wherein the first area of the contact surface and the second area of the contact surface do not overlap;
a plurality of emitter-detector pairs, wherein each of the plurality of emitter-detector pairs includes one optical emitter and one optical detector;
wherein at least some of the plurality of emitter-detector pairs have different distances between the corresponding optical emitters and optical detectors so that the portion of emitted light that is detected by the optical detector tends to travel through the sample at different depths for the emitter-detector pairs with different distances;
wherein a set of the emitter-detector pairs contains at least three emitter-detector pairs with mutually different distances and with approximately the same wavelength characteristic, and wherein additional emitter-detector pairs use a different wavelength characteristic; and
a controller configured to:
activate the optical emitter and the optical detector to produce a light intensity measurement.

32. The device of claim 31, wherein one or more of the plurality of emitter-detector pairs uses a first wavelength characteristic, wherein one or more of the plurality of emitter-detector pairs uses a second wavelength characteristic that is different from the first wavelength characteristic, and wherein one or more of the plurality of emitter-detector pairs uses a third wavelength characteristic that is different from the first and second wavelength characteristics.

33. The device of claim 32, wherein a first set with multiple of the plurality of emitter-detector pairs use approximately the same first wavelength characteristics, wherein a second set with multiple of the plurality of emitter-detector pairs use approximately the same second wavelength characteristics, and wherein a third set with multiple of the plurality of emitter-detector pairs use approximately the same third wavelength characteristics.

34. The device of claim 33, wherein the first set of the emitter-detector pairs contains at least three emitter-detector pairs with mutually different distances between the respective optical emitters and optical detectors, wherein the second set of the emitter-detector pairs contains at least three emitter-detector pairs with mutually different distances between the respective optical emitters and optical detectors, wherein the third set of the emitter-detector pairs contains at least three emitter-detector pairs with mutually different distances between the respective optical emitters and optical detectors.

35. The device of claim 34, wherein the optical detectors have a dynamic range of at least 1:100.

36. The device of claim 31,
wherein a set of at least two of the plurality of emitter-detector pairs have approximately the same distances between the corresponding optical emitters and optical detectors and use approximately the same wavelength characteristics.

37. The device of claim 31, wherein the optical emitter and the optical detector are semiconductor elements.

38. The device of claim 37, wherein the optical emitter and the optical detector semiconductor elements are configured to be less than 1.5 mm from the sample when the device is in a measuring position.

39. The device of claim 37, wherein the optical emitter and the optical detector semiconductor elements are configured to be no further than 6 mm from the sample when the device is in a measuring position.

40. A device for optical measurement of carotenoids or antioxidants in a sample of human or animal tissue or blood, the device comprising:
a contact surface configured to contact the sample;
an optical emitter configured to emit light through a first area of the contact surface and into the sample;
an optical detector configured to receive light from the sample through a second area of the contact surface, wherein the first area of the contact surface and the second area of the contact surface do not overlap;
a plurality of emitter-detector pairs, wherein each of the plurality of emitter-detector pairs includes one optical emitter and one optical detector, wherein:
at least some of the plurality of emitter-detector pairs have different distances between the corresponding optical emitters and optical detectors so that the portion of emitted light that is detected by the optical detector tends to travel through the sample at different depths for the emitter-detector pairs with different distances;
a first set of the emitter-detector pairs contains at least two emitter-detector pairs with a similar first wavelength characteristic and with mutually different distances between the respective optical emitters and optical detectors;

a second set of the emitter-detector pairs contains at least two emitter-detector pairs with a wavelength characteristic which is similar to the first wavelength characteristic and with mutually different distances between the respective optical emitters and optical detectors, wherein no emitter-detector pair of the first set is contained in the second set, and a third set of the emitter-detector pairs contains at least two emitter-detector pairs with a similar second wavelength characteristic and with mutually different distances between the respective optical emitters and optical detectors, and a fourth set of the emitter-detector pairs contains at least two emitter-detector pairs with a wavelength characteristic which is similar to the second wavelength characteristic and with mutually different distances between the respective optical emitters and optical detectors, wherein no emitter detector pair of the third set is contained in the fourth set; and a controller configured to:
activate the optical emitter and the optical detector to produce a light intensity measurement.

41. A device for optical measurement of carotenoids or antioxidants in a sample of human or animal tissue or blood, the device comprising:

a contact surface configured to contact the sample;
an optical emitter configured to emit light through a first area of the contact surface and into the sample;
an optical detector configured to receive light from the sample through a second area of the contact surface, wherein the first area of the contact surface and the second area of the contact surface do not overlap;
a plurality of emitter-detector pairs, wherein each of the plurality of emitter-detector pairs includes one optical emitter and one optical detector;
wherein a first set with multiple of the plurality of emitter-detector pairs use approximately the same first wavelength characteristics, wherein the first set includes at least two emitter-detector pairs with approximately the same first distances between the corresponding optical emitters and optical detectors, at least two emitter-detector pairs with approximately the same second distances between the corresponding optical emitters and optical detectors, which are different from the first distances, and at least two emitter-detector pairs with approximately the same third distances between the corresponding optical emitters and optical detectors, which are different from the first and second distances;
wherein a second set with multiple of the plurality of emitter-detector pairs use approximately the same second wavelength characteristics that are different from the first wavelength characteristics, wherein the second set includes at least two emitter-detector pairs with approximately the same fourth distances between the corresponding optical emitters and optical detectors, at least two emitter-detector pairs with approximately the same fifth distances between the corresponding optical emitters and optical detectors, which are different from the fourth distances, and at least two emitter-detector pairs with approximately the same sixth distances between the corresponding optical emitters and optical detectors, which are different from the fourth and fifth distances; and wherein a third set with multiple of the plurality of emitter-detector pairs use approximately the same third wavelength characteristics that are different from the first and second wavelength characteristics, wherein the third set includes at least two emitter-detector pairs with approximately the same seventh distances between the corresponding optical emitters and optical detectors, at least two emitter-detector pairs with approximately the same eighth distances between the corresponding optical emitters and optical detectors, which are different from the seventh distances, and at least two emitter-detector pairs with approximately the same ninth distances between the corresponding optical emitters and optical detectors, which are different from the seventh and eighth distances; and wherein the plurality of emitter-detector pairs are arranged in an area small enough to fit on the ball of the thumb of a human hand; and a controller configured to:
activate the optical emitter and the optical detector to produce a light intensity measurement.

42. A device for optical measurement of carotenoids or antioxidants in a sample of human or animal tissue or blood, the device comprising:

a contact surface configured to contact the sample;
an optical emitter configured to emit light through a first area of the contact surface and into the sample;
an optical detector configured to receive light from the sample through a second area of the contact surface, wherein the first area of the contact surface and the second area of the contact surface do not overlap;
a plurality of emitter-detector pairs, wherein each of the plurality of emitter-detector pairs includes one optical emitter and one optical detector;
wherein a first set with multiple of the plurality of emitter-detector pairs use approximately the same first wavelength characteristics, wherein the first set includes at least three emitter-detector pairs with approximately the same first distances between the corresponding optical emitters and optical detectors, at least three emitter-detector pairs with approximately the same second distances between the corresponding optical emitters and optical detectors, which are different from the first distances, and at least three emitter-detector pairs with approximately the same third distances between the corresponding optical emitters and optical detectors, which are different from the first and second distances;
wherein a second set with multiple of the plurality of emitter-detector pairs use approximately the same second wavelength characteristics that are different from the first wavelength characteristics, wherein the second set includes at least three emitter-detector pairs with approximately the same fourth distances between the corresponding optical emitters and optical detectors, at least three emitter-detector pairs with approximately the same fifth distances between the corresponding optical emitters and optical detectors, which are different from the fourth distances, and at least three emitter-detector pairs with approximately the same sixth distances between the corresponding optical emitters and optical detectors, which are different from the fourth and fifth distances;
wherein a third set with multiple of the plurality of emitter-detector pairs use approximately the same third wavelength characteristics that are different from the first and second wavelength characteristics, wherein the third set includes at least three emitter-detector pairs with approximately the same seventh distances between the corresponding optical emitters and optical detectors, at least three emitter-detector pairs with approximately the same eighth distances between the corresponding optical emitters and optical detectors, which are different from the seventh distances, and at least three emitter-detector pairs with approximately the same ninth distances between the corresponding optical emitters and optical detectors, which are different from the seventh and eighth distances;

wherein a fourth set with multiple of the plurality of emitter-detector pairs use approximately the same fourth wavelength characteristics that are different from the first, second, and third wavelength characteristics, wherein the fourth set includes at least three emitter-detector pairs with approximately the same tenth distances between the corresponding optical emitters and optical detectors, at least three emitter-detector pairs with approximately the same eleventh distances between the corresponding optical emitters and optical detectors, which are different from the tenth distances, and at least three emitter-detector pairs with approximately the same twelfth distances between the corresponding optical emitters and optical detectors, which are different from the tenth and eleventh distances; and wherein the plurality of emitter-detector pairs are arranged in an area small enough to fit on the ball of the thumb of a human hand; and a controller configured to:
  activate the optical emitter and the optical detector to produce a light intensity measurement.

43. A device for optical measurement of carotenoids or antioxidants in a sample of human or animal tissue or blood, the device comprising:

a contact surface configured to contact the sample;

an optical emitter configured to emit light through a first area of the contact surface and into the sample;

an optical detector configured to receive light from the sample through a second area of the contact surface, wherein the first area of the contact surface and the second area of the contact surface do not overlap;

at least two optical emitters that have different wavelength characteristics;

at least two optical detectors that have different wavelength characteristics;
  wherein the bandwidths of the wavelength characteristics of the optical emitters and/or the optical detectors are wide enough so that by combination of different optical emitters with different optical detectors a number of different wavelength characteristic can be created, wherein the number of different wavelength characteristics is higher than the number of emitters of different wavelength characteristics and higher than the number of optical detectors of different wavelength characteristics; and a controller configured to:

activate the optical emitter and the optical detector to produce a light intensity measurement.

* * * * *